US012662460B2

(12) United States Patent
Byrd et al.

(10) Patent No.: US 12,662,460 B2
(45) Date of Patent: Jun. 23, 2026

(54) COMPOSITIONS FOR USE FOR THE INHIBITION OF DIHYDROOROTATE DEHYDROGENASE

(71) Applicants: OHIO STATE INNOVATION FOUNDATION, Columbus, OH (US); HENDRIX COLLEGE, Conway, AK (US)

(72) Inventors: John C. Byrd, Columbus, OH (US); Chad E. Bennett, Columbus, OH (US); Sandip Madhukar Vibhute, Columbus, OH (US); Thomas E. Goodwin, Conway, AK (US); Erin Hertlein, Columbus, OH (US); Ola A. Elgamal, Columbus, OH (US); Tyler A. Wilson, Columbus, OH (US)

(73) Assignees: Ohio State Innovation Foundation, Columbus, OH (US); Hendrix College, Conway, AK (US)

( * ) Notice: Subject to any disclaimer, the term of this patent is extended or adjusted under 35 U.S.C. 154(b) by 958 days.

(21) Appl. No.: 17/789,182

(22) PCT Filed: Dec. 22, 2020

(86) PCT No.: PCT/US2020/066682

§ 371 (c)(1),
(2) Date: Jun. 25, 2022

(87) PCT Pub. No.: WO2021/133831

PCT Pub. Date: Jul. 1, 2021

(65) Prior Publication Data

US 2023/0109418 A1 Apr. 6, 2023

Related U.S. Application Data

(60) Provisional application No. 62/953,705, filed on Dec. 26, 2019.

(51) Int. Cl.
*C07D 401/04* (2006.01)
*A61P 35/00* (2006.01)

(52) U.S. Cl.
CPC ............ *C07D 401/04* (2013.01); *A61P 35/00* (2018.01)

(58) Field of Classification Search
CPC ............................... C07D 401/04; A61P 35/00
See application file for complete search history.

(56) References Cited

U.S. PATENT DOCUMENTS 2,888,346 A 5/1959 Tulagin
2011/0263620 A1* 10/2011 Hsieh ...................... A61P 31/12 546/159

OTHER PUBLICATIONS

CAplus Registry Number: RN 854868-00-1. [Database Registry Chemical Abstracts Service, Columbus, Ohio, Accession No. RN 854868-00-1, Entered STN: Jul. 13, 2005] (Year: 2005).*
Madak, J., et al, Design, Synthesis, and Biological Evaluation of 4-Quinoline Carboxylic Acids as Inhibitors of Dihydroorotate Dehydrogenase. Journal of Medicinal Chemistry 2018 61 (12), 5162-5186 (Year: 2018).*
Madak Joseph T. et al: "Design, Synthesis, and Biological Evaluation of 4-Quinoline Carboxylic Acids as Inhibitors of Dihydroorotate Dehydrogenase", Journal of Medicinal Chemistry, vol. 61, No. 12, May 4, 2018 (May 4, 2018), pp. 5162-5186, XP055790577, ISSN: 0022-2623, DOI: 10.1021 /acs.jmedchem.7b01862 Retrieved from the Internet: URL:https://pubs.acs.org/doi/pdf/10.1021/acs.jmedchem.7b01862.
Marianne Lucas-Hourani et al: "Original 2-(3-Alkoxy-1 H-pyrazol-1-yl)azines Inhibitors of Human Dihydroorotate Dehydrogenase (DHODH)", Journal of Medicinal Chemistry, vol. 58, No. 14, Jun. 30, 2015 (Jun. 30, 2015), pp. 5579-5598, XP0557 40284, ISSN: 0022-2623, DOI: 10.1021 /acs.jmedchem.5b00606.
Buu-Hoi N.P. et al: "Orientation in Friedel-Crafts Acylations of 3-Chloro-2-methoxybiphenyl", Journal of Organic Chemistry, vol. 24, Jan. 1, 1959 (Jan. 1, 1959), pp. 39-41, XP055790606,.

* cited by examiner

*Primary Examiner* — Adam C Milligan
*Assistant Examiner* — Ernesto Valle
(74) *Attorney, Agent, or Firm* — Maynard Nexsen PC; John P. Zimmer

(57) ABSTRACT

Disclosed herein are compounds, 6-substituted-2-(phenyl-heteroaryl)quinoline-4-carboxylic acid analogs, that are inhibitors of dihydroorotate dehydrogenase (DHODH). The disclosed compounds can be used in the treatment of a variety of disorders and diseases in which inhibition of DHODH can be clinically useful, including cancer, such as a hematological cancer, including acute myeloid leukemia (AML); graft-versus-host-diseases; autoimmune disorders; and disorders associated with T-cell proliferation. This abstract is intended as a scanning tool for purposes of searching in the particular art and is not intended to be limiting of the present disclosure.

20 Claims, 1 Drawing Sheet

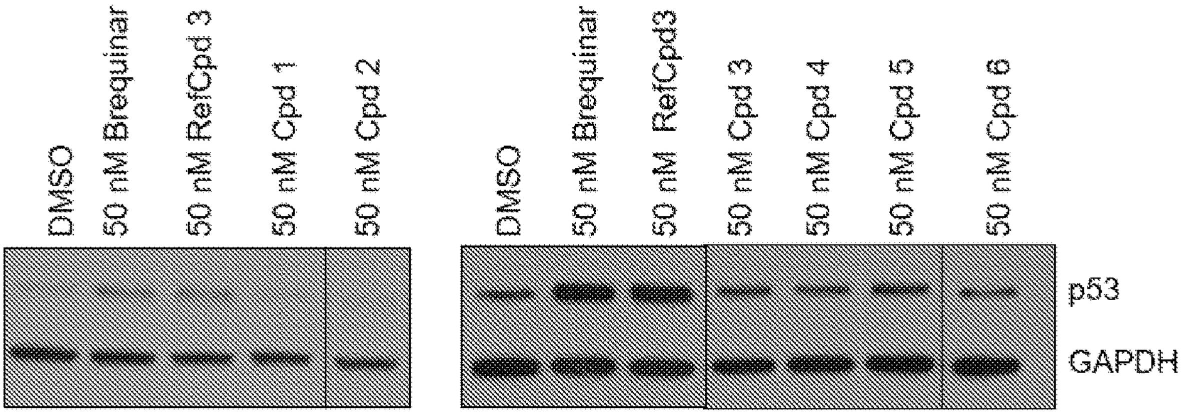
*Lines in the blots indicate where data from additional compounds has been removed from the figure. Individual compounds are always compared to Brequinar and RefRefCpd3 samples on the same blot.

COMPOSITIONS FOR USE FOR THE INHIBITION OF DIHYDROOROTATE DEHYDROGENASE

CROSS-REFERENCE TO RELATED APPLICATIONS

This Application is the 35 U.S.C. § 371 national stage application of PCT Application No. PCT/US2020/066682, filed Dec. 22, 2020, where the PCT claims priority to, and the benefit of U.S. Provisional Application No. 62/953,705, filed on Dec. 26, 2019, both of which are herein incorporated by reference in their entireties.

BACKGROUND

Proliferating cells require a supply of nucleotides for replication of DNA and transcription of genes to RNA, as well as for a variety of other metabolic processes. Cells can supply such nucleotides by de novo nucleotide synthesis pathways. An important step in the de novo synthesis pathway of pyrimidine nucleotides is the oxidation of dihydroorotate to form orotate. That reaction is catalyzed by dihydroorotate dehydrogenase (DHODH) and that step is one of the rate-limiting steps in the pyrimidine nucleotide synthesis pathway. DHODH has a sub-cellular location in the mitochondrial membrane and uses cytochrome C in the electron transport chain as an electron acceptor for the oxidation of dihydroorotate to orotate.

Under normal circumstances the intracellular pool of pyrimidine nucleotides can be replenished by a salvage pathway in which pyrimidine nucleotides are recycled. Although this DHODH-independent mechanism is sufficient for resting lymphocytes, 'activated' and proliferating lymphocytes need to substantially increase the available pyrimidine and so become dependent on de novo pyrimidine synthesis. Since orotate is a necessary intermediate in pyrimidine nucleotide synthesis, and since pyrimidine nucleotides are required for DNA replication, gene expression, and carbohydrate metabolism, inhibition of the DHODH enzyme can inhibit cell growth.

Moreover, rapidly proliferating cells require pyrimidines not only for cellular growth, but also for protein glycosylation, membrane lipid biosynthesis and strand break repair (e.g., see Fairbanks, et al., J. Biol. Chem. 270:29682-29689 (1995)). Under such conditions, in order to meet the increased demand, substantial quantities of pyrimidine nucleotides must be produced in rapidly proliferating cells. Accordingly, DHODH inhibitors are attractive candidates for treating proliferative disorders (e.g., see Liu, S., et al., Structure 8:25-31 (2000)), and various studies have shown that DHODH inhibitors can stop the proliferation of tumor cells in some circumstances (e.g., see Loffier, Eur. J. Biochem. 107:207-215 (1980)).

Other circumstances in which DHODH inhibitors have been identified as candidates for the clinical control of rapid cell division include activated immune cells, diseased skin cells, cancers, and infectious agents. Examples of DHODH inhibitors used or being developed for proliferative disorders include brequinar, leflunomide, and teriflunomide. Inhibitors of DHODH have further been disclosed for the treatment or prevention of autoimmune diseases, immune and inflammatory diseases, angioplastic-related disorders, viral, bacterial, and protozoic diseases.

Although DHODH is an attractive target for therapeutic intervention for a variety of clinical conditions, including cancer, there remain significant issues with currently described compounds. For example, many of these compounds, including brequinar, suffer from being associated with poor bioavailability, due in part to the poor aqueous solubility and GI uptake. Accordingly, currently described DHODH inhibitors can have limited pharmaceutical efficacy due to such bioavailability issues.

Despite advances in research directed towards effective and therapeutically useful DHODH inhibitors, there remain a scarcity of compounds that are both efficacious and have the appropriate bioavailability properties. These needs and other needs are satisfied by the present disclosure.

SUMMARY

In accordance with the purpose(s) of the disclosure, as embodied and broadly described herein, the disclosure, in one aspect, relates to compounds that are inhibitors of dihydroorotate dehydrogenase (DHODH), and the disclosed compounds have improved pharmacokinetic properties making them extremely useful for therapeutic intervention in a variety of disorders and diseases in which inhibition of DHODH can be clinically useful, e.g., cancer. In various aspects, the disclosed compounds are 6-substituted-2-(phenylheteroaryl)quinoline-4-carboxylic acid analogs. In further aspects, the disclosed compounds can be used in methods of treating a cancer, such as a hematological cancer, including acute myeloid leukemia (AML), graft-versus-host-diseases, and disorders associated with T-cell proliferation. In some aspects, the disclosed compounds can demonstrate flip-flop kinetics when administered orally, i.e., pharmacokinetics in which the rate of absorption, rather than the rate of elimination, dominates the pharmacokinetics. Moreover, the disclosed compounds can demonstrate a sustained pharmacokinetic profile instead of an immediate release profile.

Disclosed are compounds having a formula represented by a structure:

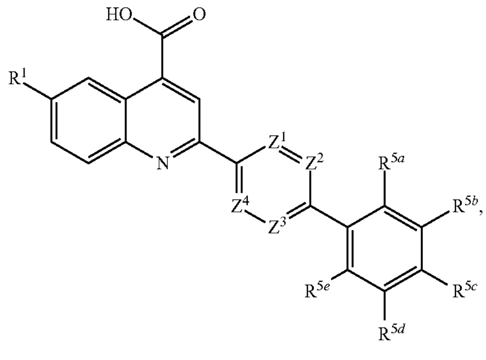

wherein each of $Z^1$, $Z^2$, $Z^3$, and $Z^4$ is independently selected from CH and N; wherein $R^1$ is selected from hydrogen, halogen, —$SF_5$, —CN, —$N_3$, —OH, —$NH_2$, —$CF_3$, and —$CF_2CF_3$; wherein one of $R^{5a}$, $R^{5b}$, $R^{5c}$, $R^{5d}$, and $R^{5e}$ is selected from a group having formula represented by a structure: —$R^{20}$, —$R^{30}$-$A^1$-$R^{40}$, -$A^1$-$R^{40}$, -$A^1$-$R^{30}$-$A^2$-$R^{40}$, or -$A^1$-$R^{30}$-$A^2$-$R^{31}$-$A^3$-$R^{40}$; wherein $A^1$ is selected from —O— and —$NR^{50}$—; wherein $R^{50}$ is selected from hydrogen, —C1-C10 alkyl, —C1-C10 aminoalkyl, and —C1-C10 hydroxyalkyl; wherein $A^2$ is selected from —O— and —$NR^{60}$—; wherein $R^{60}$ is selected from hydrogen, —C1-C10 alkyl, —C1-C10 aminoalkyl, and —C1-C10 hydroxyalkyl; wherein $A^3$ is selected from —O— and —$NR^{70}$—;

wherein $R^{70}$ is selected from hydrogen, —C1-C10 alkyl, —C1-C10 aminoalkyl, and —C1-C10 hydroxyalkyl; wherein $R^{20}$ is selected from halogen, —C1-C10 alkyl, —C1-C10 haloalkyl, —C1-C10 hydroxyalkyl, —C1-C10 alkylamino, and —C1-C10 alkoxy; wherein each of $R^{30}$ and $R^{31}$ is independently selected from —C1-C10 alkanediyl, —C1-C10 haloalkanediyl, —C1-C10 aminoalkanediyl, and —C1-C10 hydroxyalkanediyl; and wherein $R^0$ is selected from —C1-C10 alkyl, —C1-C10 haloalkyl, —C1-C10 aminoalkyl, —C1-C10 hydroxyalkyl, and $—(CH_2)_nAr^1$; wherein n is an integer selected from 1, 2, and 3; and wherein $Ar^1$ is a phenyl group substituted with 0, 1, 2, 3, 4, or 5 groups independently selected from halogen, $—SF_5$, —CN, $—N_3$, —OH, $—NH_2$, —C1-C4 alkyl, —C1-C4 alkoxy, —C1-C4 haloalkyl, —C1-C4 aminoalkyl, —C1-C4 alkylamino, —C1-C4 haloalkylamino, —C1-C4 hydroxyalkyl, —C1-C4 halohydroxyalkyl, cycloalkyl, and heterocycloalkyl; and wherein four of $R^{5a}$, $R^{5b}$, $R^{5c}$, $R^{5d}$, and $R^{5e}$ are independently selected from hydrogen, halogen, $—SF_5$, —CN, $—N_3$, —OH, $—NH_2$, $—CF_3$, and $—CF_2CF_3$; or a pharmaceutically acceptable salt thereof.

Also disclosed are pharmaceutical compositions comprising a therapeutically effective amount of a disclosed compound, or a pharmaceutically acceptable salt thereof, and a pharmaceutically acceptable carrier.

Also disclosed are methods for the treatment of a disease or disorder in a mammal comprising the step of administering to the mammal a therapeutically effective amount of at least one disclosed compound, or a pharmaceutically acceptable salt thereof, or a disclosed pharmaceutical composition.

Also disclosed are methods for the treatment of a cancer in a mammal comprising the step of administering to the mammal a therapeutically effective amount of at least one disclosed compound, or a pharmaceutically acceptable salt thereof, or a disclosed pharmaceutical composition.

Also disclosed are methods for the treatment of a graft-versus-host disease in a mammal comprising the step of administering to the mammal a therapeutically effective amount of at least one disclosed compound, or a pharmaceutically acceptable salt thereof, or a disclosed pharmaceutical composition.

Also disclosed are methods for the treatment of a disease or disorder associated with T-cell proliferation in a mammal comprising the step of administering to the mammal a therapeutically effective amount of at least one disclosed compound, or a pharmaceutically acceptable salt thereof, or a disclosed pharmaceutical composition.

Also disclosed are kits comprising a therapeutically effective amount of at least one disclosed compound, or a pharmaceutically acceptable salt thereof, or a disclosed pharmaceutical composition; and: (a) at least one agent known to treat a cancer, a host-versus-graft-disease, and/or a disorder associated with T-cell proliferation; and (b) instructions for treating a cancer, a host-versus-graft-disease, and/or a disorder associated with T-cell proliferation.

Also disclosed are methods for manufacturing a medicament comprising combining at least one disclosed compound or at least one disclosed product with a pharmaceutically acceptable carrier or diluent.

Also disclosed are uses of a disclosed compound or a disclosed product in the manufacture of a medicament for the treatment of a disease or disorder in a mammal such as a cancer, a disorder associated with T-cell proliferation, or a graft-versus-host-disease.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

FIG. 1 shows representative data for the effect of representative disclosed compounds on the expression of p53 in an AML cell-line as determined by immunobot analysis.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims.

The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a unimolecular nanoparticle," "a nanocluster," or "a biomimetic vesicle," including, but not limited to, two or more such unimolecular nanoparticles, nanoclusters, or biomimetic vesicles, including combinations of unimolecular nanoparticles, nanoclusters, or biomimetic vesicles, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, "dihydroorotate dehydrogenase" and "DHODH" can be used interchangeably, and refer to an enzyme encoded by a gene in humans with a cytogenetic location of 16q22.2 and a molecular location of base pairs 72,008,744 to 72,025,417 on chromosome 16 (*Homo sapiens* Annotation Release 109, GRCh38.p12). The gene structure in humans comprises 9 exons. DHODH has an EC classification of 1.3.1.1; an intracellular location within the mitochondria; and catalyzes the fourth enzymatic step in de novo pyrimidine biosynthesis. DHODH has also been referred to as DHOdehase; dihydroorotate dehydrogenase, mitochondrial; dihydroorotate dehydrogenase, mitochondrial precursor; dihydroorotate oxidase; human complement of yeast URA1; POADS; PYRD_HUMAN; and URA1.

The terms "inhibits", "inhibiting", or "inhibitor" of DHODH, as used herein, refer to inhibition of the enzyme DHODH, unless otherwise specified.

As used herein, "$IC_{50}$," is intended to refer to the concentration of a substance (e.g., a compound or a drug) that is required for 50% inhibition of a biological process, enzymatic reaction, or component of a biological or enzymatic process. For example, $IC_{50}$ refers to the half maximal (50%) inhibitory concentration (IC) of a substance as determined in a suitable assay. For example, an $IC_{50}$ for DHODH activity can be determined in an in vitro enzymatic assay using the methods described herein. Alternatively, an activity can be determined in a cell-based assay, including measurement of an activity or function associated with inhibition of the target process or enzyme. That is, DHODH activity can be indirectly determined in a cell-based assay of cell proliferation. It is believed that DHODH inhibition can lead to growth arrest or inhibition in suitable cell types. DHODH activity can be determined in a suitable cell, such as a primary AML cell or a AML cell-line, using an assay for cell-proliferation, such as an MTS assay as described herein, or a cell-colony forming assay as described herein. Suitable cell lines are described herein below.

As used herein, the term "immune" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

As used herein, "brequinar" and "BQR," which can be used interchangeably, refer to the compound having a structure represented by the following formula:

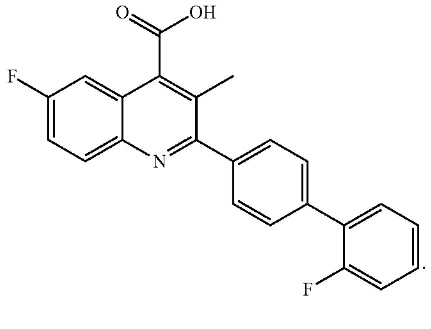 [SMILES: Cc1c(-c2ccc(-c3ccccc3F)cc2)nc2ccc(F)cc2c1C(=O)O]

Brequinar can also be referred to by the IUPAC chemical name, or 6-fluoro-2-(2'-fluoro-1,1'-biphenyl-4-yl)-3-methyl-4-quinolinecarboxylic acid. Common salt forms are brequinar potassium and brequinar sodium (also referred to herein as BQR Na), which are the alkali metal salts of the conjugate base of the carboxylic acid. Brequinar is sometimes referred as DuP-785 or NSC-368390.

As used herein, "graft-versus-host-disease," "graft versus host disease," and GVHD can be used interchangeably, and refer to clinical complications following an allogeneic tissue transplant. It is commonly associated with stem cell or bone marrow transplant but the term also applies to other forms of tissue graft. Immune cells (white blood cells) in the tissue (the graft) recognize the recipient (the host) as "foreign". The transplanted immune cells then attack the hosts body cells. GVHD can also occur after a blood transfusion if the blood products used have not been irradiated or treated with an approved pathogen reduction system.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like.

Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Waals forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof. It is understood that a vertebrate can be mammal, a fish, a bird, a reptile, or an amphibian. Thus, the subject of the herein disclosed methods can be a human, non-human primate, horse, pig, rabbit, dog, sheep, goat, cow, cat, guinea pig or rodent The term does not denote a particular age or sex.

Moreover, adult and newborn subjects, as well as fetuses, whether male or female, are intended to be covered. A patient refers to a subject afflicted with a clinical condition, disease or disorder. The term "patient" includes human and veterinary subjects.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a cancer, a disorder or disease associated with T-cell proliferation, or a graft-versus-host-disease. The effect can be therapeutic in terms of a partial or complete cure of a disease, condition, symptom or adverse effect attributed to the disease, disorder, or condition. The term "treatment" as used herein can include any treatment of a cancer, a disorder or disease associated with T-cell proliferation, or a graft-versus-host-disease in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the disclosure (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

In the present disclosure, it is understood that in some cases, an effective amount or dose of a disclosed compound is the amount of the composition that is capable of inhibiting DHODH to provide a clinically meaningful decrease in the signs, symptoms, or causes of a disease, or any other desired alteration of a biological system, as a result of inhibiting DHODH. For example, an "effective amount" for therapeutic uses. In some aspects, an appropriate "effective" amount in any individual case is determined using techniques, such as a dose escalation study.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

It is understood, that unless otherwise specified, temperatures referred to herein are based on atmospheric pressure (i.e. one atmosphere).

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, the term "substituted" is contemplated to include all permissible substituents of organic compounds.

In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. Similarly, "$Ar^1$," "$Ar^2$," "$Ar^3$," and "$Ar^4$" are used herein as generic symbols to represent various specific aryl substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

As used herein "aminoalkyl" refers to a straight or branched chain alkyl group in which at least one hydrogen is replaced with an amino group, generally 1-3 amino groups. Non-limiting examples of aminoalkyl groups include $—CH_2NH_2$, $—(CH_2)_2NH_2$, $—CHCH_3NH_2$, $—(CH_2)_2CHCH_3NH_2$, $—(CH_2)_2CHNH_2CH_2CH_3$, $—CHCH_3(CH_2)_2NH_2$, and the like.

As used herein "alkylamino" refers to an amino group having at least one hydrogen replaced with an alkyl group. Thus, alkylamino refers to the group $—NR^aR^b$, wherein $R^a$ and $R^b$ are independently selected form H and alkyl, provided at least one of $R^a$ or $R^b$ is an alkyl. Non-limiting examples of alkylamino groups include $—NHCH_3$, $—NHCH_2CH_3$, $—NH(CH_2)_2CH_3$, $—N(CH_3)_2$, $—N(CH_3)CH_2CH_3$, $—N(CH_3)(CH_2)_2CH_3$, and the like.

As used herein "hydroxyalkyl" refers to a straight or branched chain alkyl group in which at least one hydrogen is replaced with an hydroxy group, generally 1-3 hydroxy groups. Non-limiting examples of hydroxyalkyl groups include $—CH_2OH$, $—(CH_2)_2OH$, $—CHCH_3OH$, $—(CH_2)_2CHCH_3OH$, $—(CH_2)_2CHOHCH_2CH_3$, $—CHCH_3(CH_2)_2OH$, and the like.

The term "alkanediyl", as used herein, unless otherwise indicated, means bivalent straight and branched chained saturated hydrocarbon radicals having carbon atoms. For example, "C1-C6 alkanediyl" would refer to bivalent straight and branched chained saturated hydrocarbon radicals having 1 to 6 carbon atoms, such as, for example, methylene, 1,2-ethanediyl ($—CH_2CH_2—$), propanediyl or 1,3-propanediyl ($—(CH_2)_3—$), butanediyl or 1,4-butanediyl ($—(CH_2)_4—$), pentanediyl or 1,5-pentanediyl ($—(CH_2)_5—$), hexanediyl or 1,6-hexanediyl ($—(CH_2)_6—$) and the branched isomers thereof (e.g., isopropanediyl ($—CHCH_3CH_2—$)). Alkanediyl groups can be further substituted, e.g., aminoalkanediyl or hydroxyalkanediyl.

As used herein, "aminoalkanediyl" refers to a straight or branched chain alkanediyl group in which at least one hydrogen is replaced with an amino group, generally 1-3 amino groups. Non-limiting examples of aminoalkanediyl groups include $—CH_2NH—$, $—(CH_2)_2NH—$, $—CHCH_3NH—$, $—(CH_2)_2CHCH_3NH—$, $—(CH_2)_2CHNH_2(CH_2)_2—$, $—CH_2CHNH_2(CH_2)_2—$, $—CH_2NH(CH_2)_2—$, $—(CH_2)_2NH(CH_2)_2—$, $—CHCH_3(CH_2)_2NH—$, and the like.

As used herein, "hydroxyalkanediyl" refers to a straight or branched chain alkanediyl group in which at least one hydrogen is replaced with a hydroxy group, generally 1-3 hydroxy groups. Non-limiting examples of hydroxyalkanediyl groups include $—CHOH—$, $—CH_2CHOH—$, $—CCH_3OH—$, $—(CH_2)_2CCH_3OH—$, $—(CH_2)_2CHOH$ $(CH_2)_2$—, —$CH_2CHOH(CH_2)_2$—, —$CHOH(CH_2)_2$—, —$CH_2CHOH(CH_2)_2$—, —$CHCH_3CH_2CHOH$—, and the like.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or -$OA^1$-$(OA^2)_a$-$OA^3$, where "a" is an integer of from 1 to 200 and $A^1$, $A^2$, and $A^3$ are alkyl and/or cycloalkyl groups.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyrdazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "heterocycle" as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocycyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "carboxylic acid" as used herein is represented by the formula —C(O)OH.

The terms "halo," "halogen" or "halide," as used herein can be used interchangeably and refer to F, Cl, Br, or I.

The term "hydroxyl" or "hydroxy" as used herein is represented by the formula —OH.

The term "nitro" as used herein is represented by the formula —$NO_2$.

The term "nitrile" or "cyano" as used herein is represented by the formula —CN.

"$R^1$," "$R^2$," "$R^3$," . . . "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

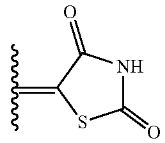 [SMILES: *=C1SC(=O)NC1=O]

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present disclosure unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfonyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the disclosure includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present disclosure includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the disclosure include isotopes of hydrogen, carbon, nitrogen, oxygen, sulfur, fluorine and chlorine, such as $^{2}H$, $^{3}H$, $^{13}C$, $^{14}C$, $^{15}N$, $^{18}O$, $^{17}O$, $^{35}S$, $^{18}F$, and $^{38}Cl$, respectively. Compounds further comprise prodrugs thereof and pharmaceutically acceptable salts of said compounds or of said prodrugs which contain the aforementioned isotopes and/or other isotopes of other atoms are within the scope of this disclosure. Certain isotopically-labeled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present disclosure and prodrugs thereof can generally be prepared by carrying out the procedures below, by substituting a readily available isotopically labeled reagent for a non-isotopically labeled reagent.

The compounds described in the disclosure can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the disclosure to form solvates and hydrates. Unless stated to the contrary, the disclosure includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the disclosure can be present in different polymorphic forms, with it being possible for particular modifications to be metastable. Unless stated to the contrary, the disclosure includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific embodiment or combination of embodiments of the methods of the disclosure.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Described herein are compounds that can inhibit dihydroorotate dehydrogenase (DHODH), and have therapeutic or clinical utility for a disease or disorder that can be treated by inhibition of DHODH. Also described herein are methods of synthesizing the disclosed compounds. Also described herein are methods of administering the disclosed compounds to a subject in need thereof. In some aspects, the subject can have a disease or disorder associated with DHODH activity, such as a cancer, a disorder or disease associated with T-cell proliferation, or a graft-versus-host-disease. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Compounds.

In various aspects, the disclosed compounds are 6-substituted-2-(phenylheteroaryl)quinoline-4-carboxylic acid analogs useful as inhibitors of dihydroxyorotate dehydrogenase, which have use as therapeutic agents in a variety of clinical conditions such as cancer, graft-versus-host disease, and disorders associated with T-cell proliferation.

Disclosed are compounds having a formula represented by a structure:

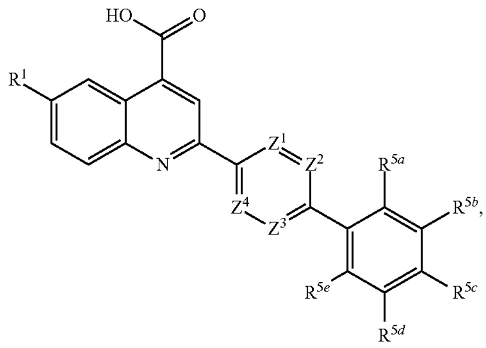

wherein each of $Z^1$, $Z^2$, $Z^3$, and $Z^4$ is independently selected from CH and N; wherein $R^1$ is selected from hydrogen, halogen, —$SF_5$, —CN, —$N_3$, —OH, —$NH_2$, —$CF_3$, and —$CF_2CF_3$; wherein one of $R^{5a}$, $R^{5b}$, $R^{5c}$, $R^{5d}$, and $R^{5e}$ is selected from a group having formula represented by a structure: —$R^{20}$, —$R^{30}$-$A^1$-$R^{40}$, -$A^1$-$R^{40}$, -$A^{1\prime}$-R-$A^2$-$R^{40}$, or -$A^1$-$R^{30}$-$A^2$-$R^{31}$-$A^3$-$R^{40}$; wherein $A^1$ is selected from —O— and —$NR^{50}$—; wherein $R^{50}$ is selected from hydrogen, —C1-C10 alkyl, —C1-C10 aminoalkyl, and —C1-C10 hydroxyalkyl; wherein $A^2$ is selected from —O— and —$NR^{60}$—; wherein $R^{60}$ is selected from hydrogen, —C1-C10 alkyl, —C1-C10 aminoalkyl, and —C1-C10 hydroxyalkyl; wherein $A^3$ is selected from —O— and —$NR^{70}$—; wherein $R^{70}$ is selected from hydrogen, —C1-C10 alkyl, —C1-C10 aminoalkyl, and —C1-C10 hydroxyalkyl; wherein $R^{20}$ is selected from halogen, —C1-C10 alkyl, —C1-C10 haloalkyl, —C1-C10 hydroxyalkyl, —C1-C10 alkylamino, and —C1-C10 alkoxy; wherein each of $R^{30}$ and $R^{31}$ is independently selected from —C1-C10 alkanediyl, —C1-C10 haloalkanediyl, —C1-C10 aminoalkanediyl, and —C1-C10 hydroxyalkanediyl; and wherein $R^{40}$ is selected from —C1-C10 alkyl, —C1-C10 haloalkyl, —C1-C10 aminoalkyl, —C1-C10 hydroxyalkyl, and —$(CH_2)_n Ar^1$; wherein n is an integer selected from 1, 2, and 3; and wherein $Ar^1$ is a phenyl group substituted with 0, 1, 2, 3, 4, or 5 groups independently selected from halogen, —$SF_5$, —CN, —$N_3$, —OH, —$NH_2$, —C1-C4 alkyl, —C1-C4 alkoxy, —C1-C4 haloalkyl, —C1-C4 aminoalkyl, —C1-C4 alkylamino, —C1-C4 haloalkylamino, —C1-C4 hydroxyalkyl, —C1-C4 halohydroxyalkyl, cycloalkyl, and heterocycloalkyl; and wherein four of $R^{5a}$, $R^{5b}$, $R^{5c}$, $R^{5d}$, and $R^{5e}$ are independently selected from hydrogen, halogen, —$SF_5$, —CN, —$N_3$, —OH, —$NH_2$, —$CF_3$, and —$CF_2CF_3$; or a pharmaceutically acceptable salt thereof.

In various aspects, a disclosed compound can be present as a compound having a structure as given by the following:

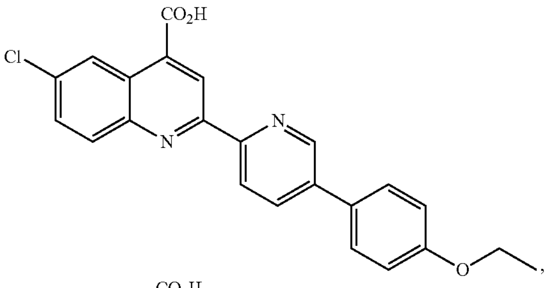

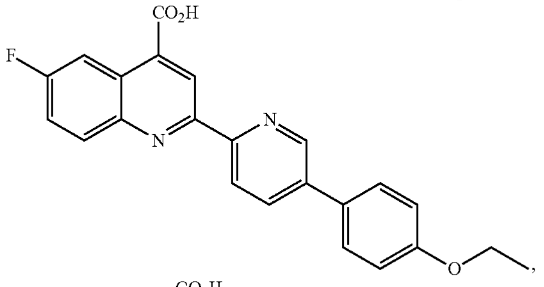

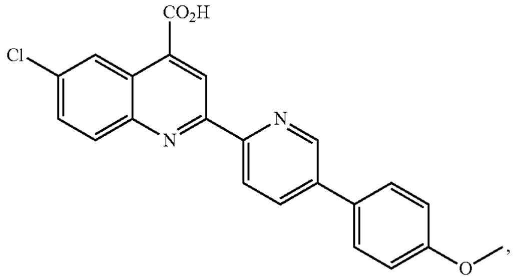

-continued

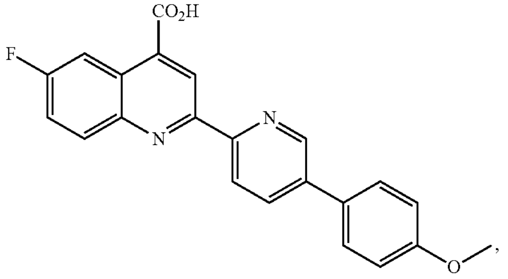

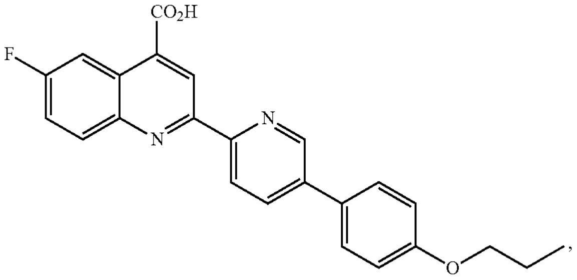

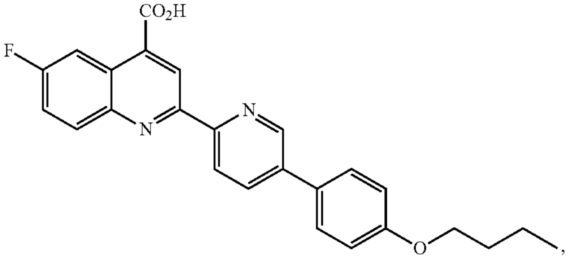

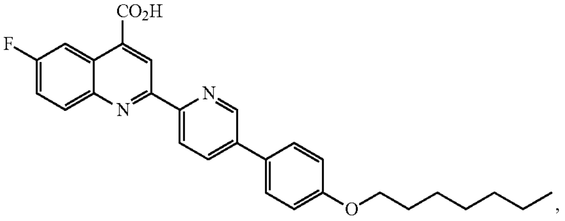

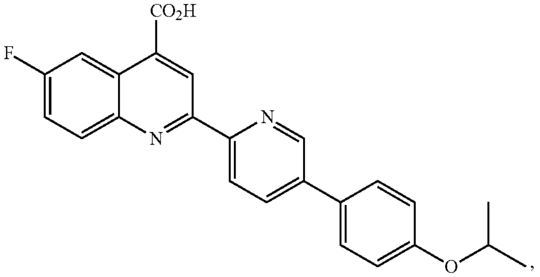

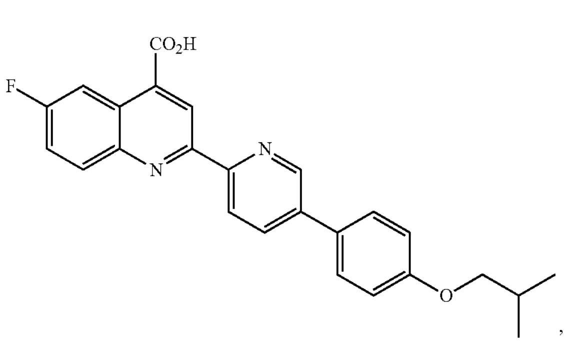

-continued
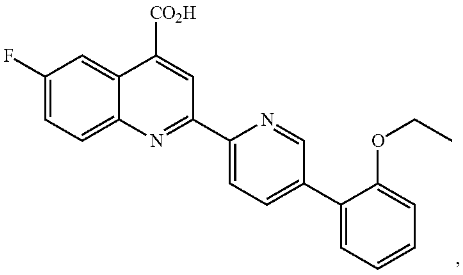
,
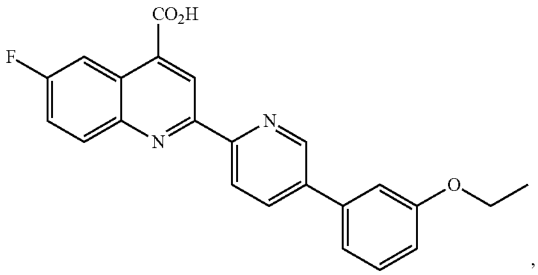
,
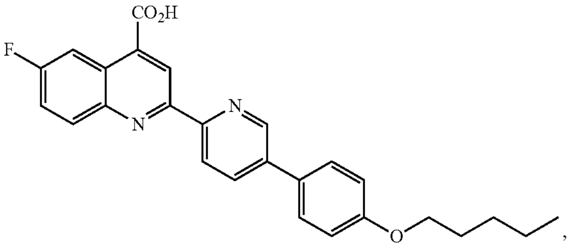
,
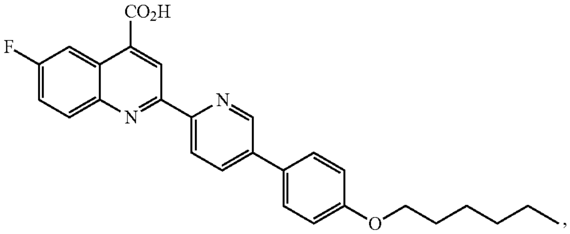
,
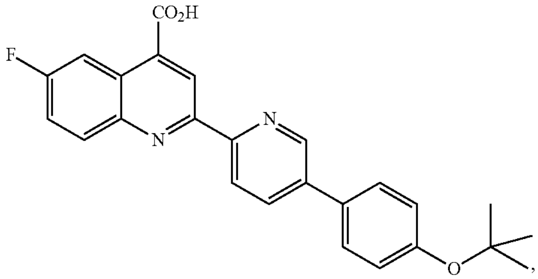
,
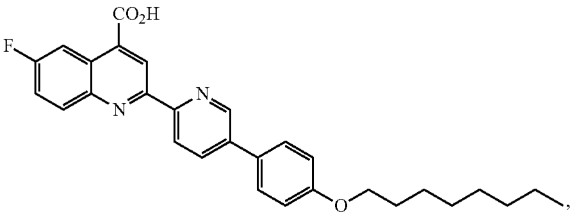
,
-continued
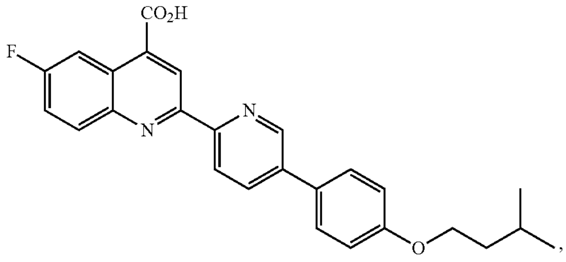
,
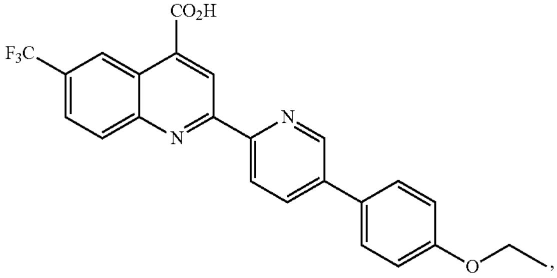
,
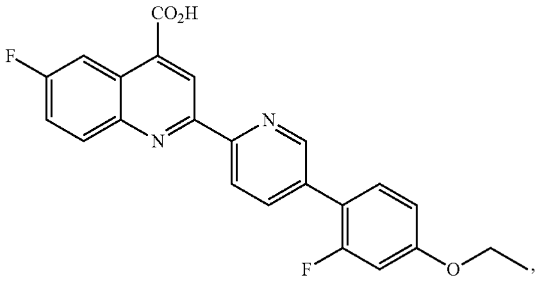
,
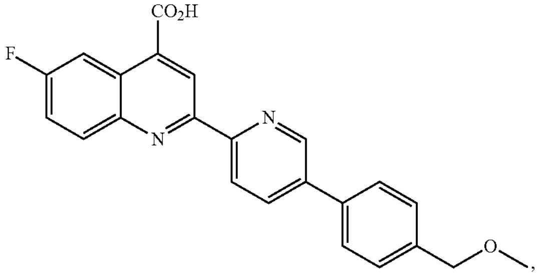
,
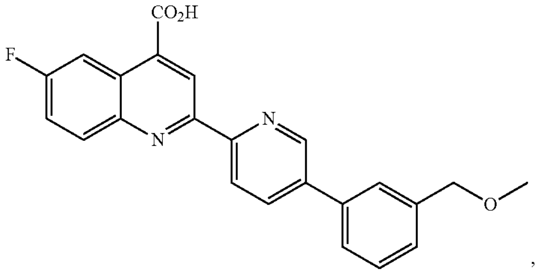
,
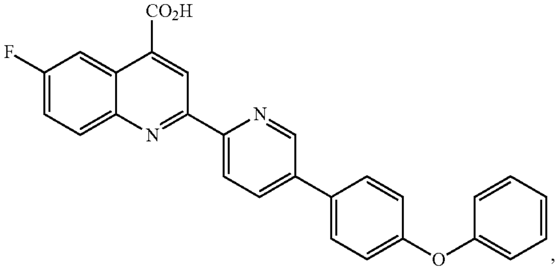
, -continued
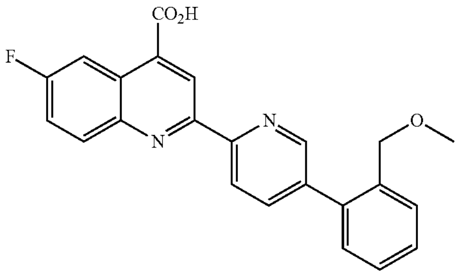
,
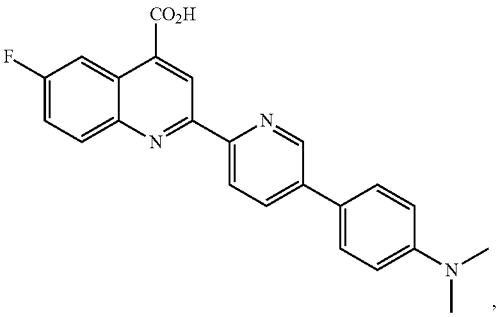
,
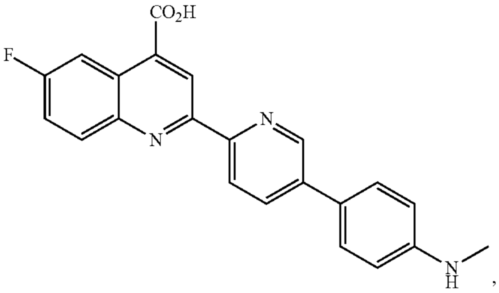
,
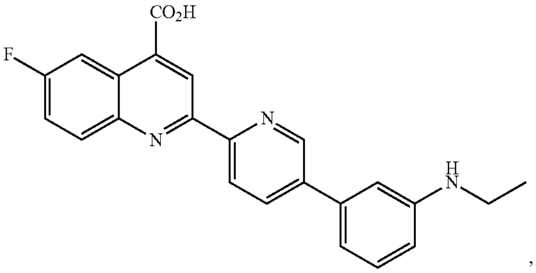
,
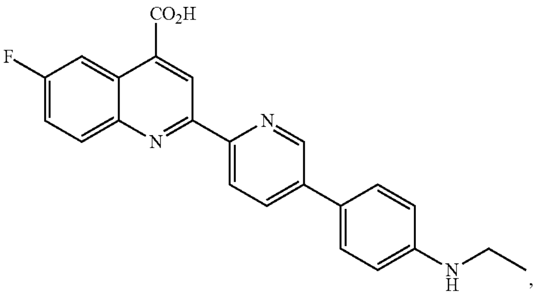
,
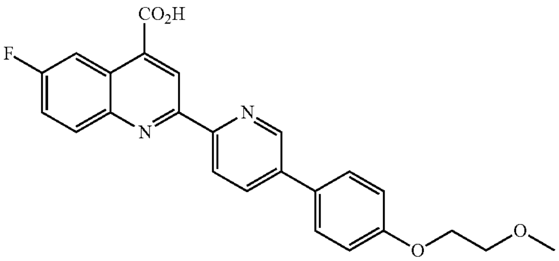
,
-continued
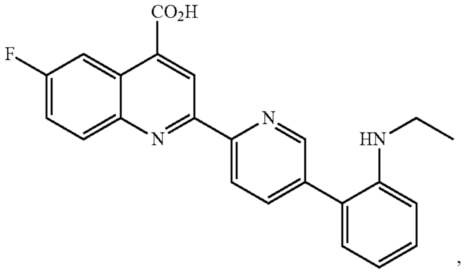
,
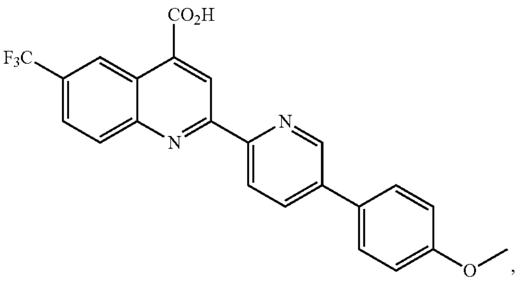
,
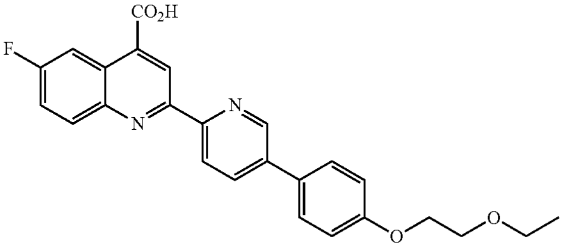
,
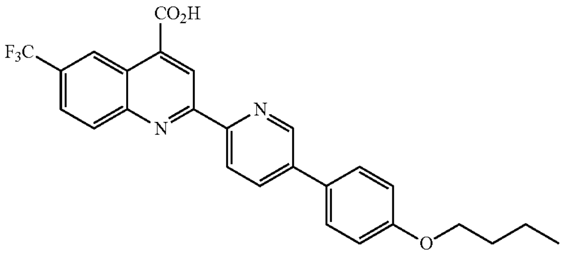
,
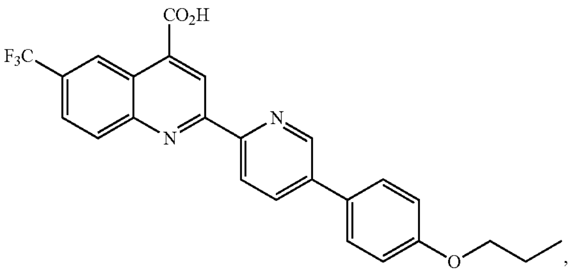
,
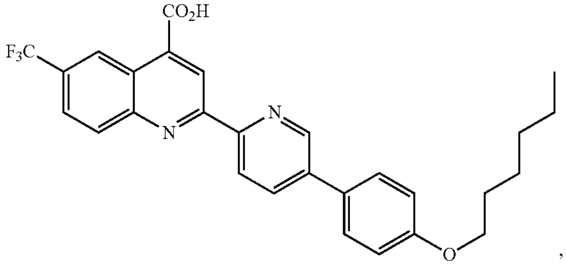
, -continued
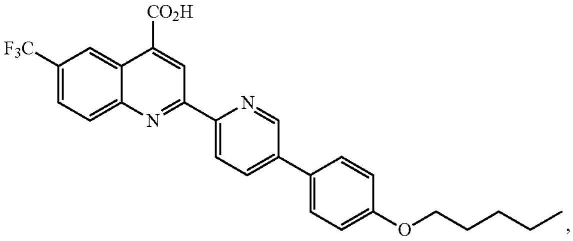,
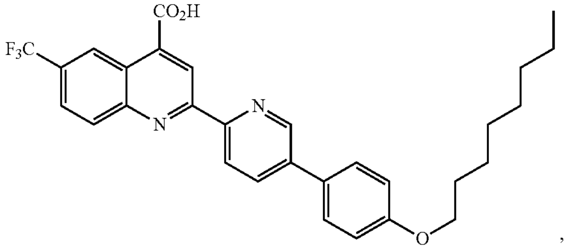,
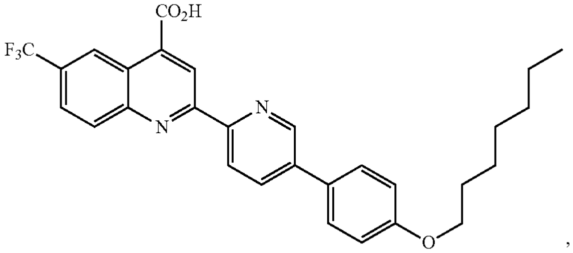,
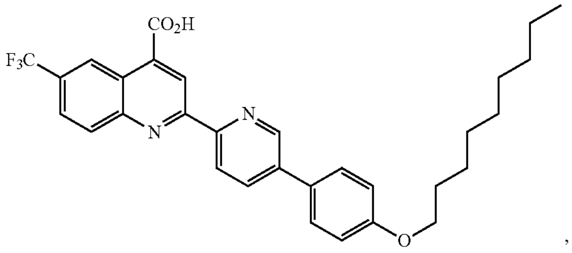,
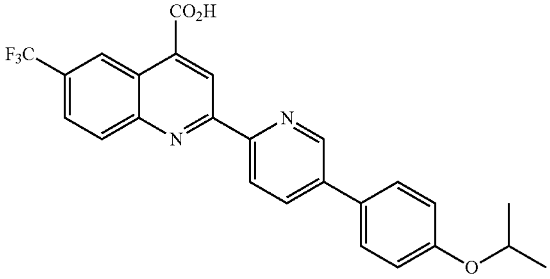,
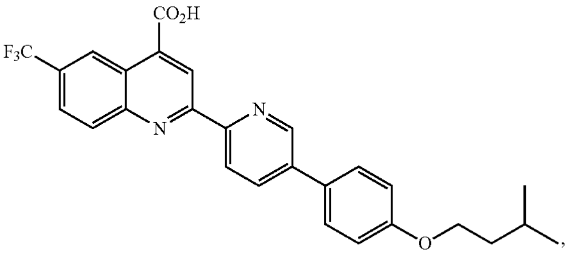,
-continued
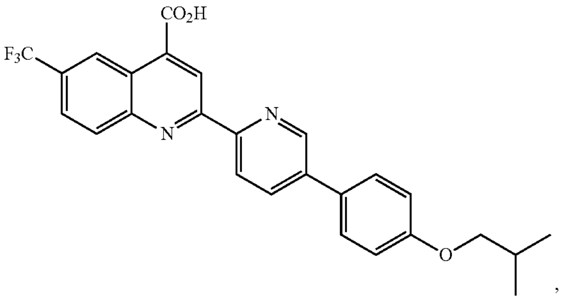,
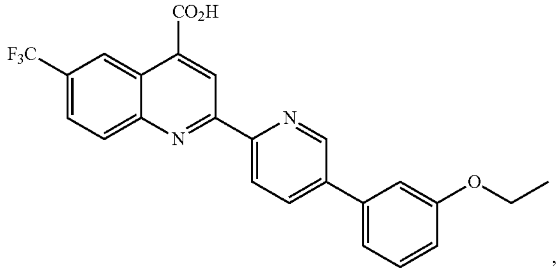,
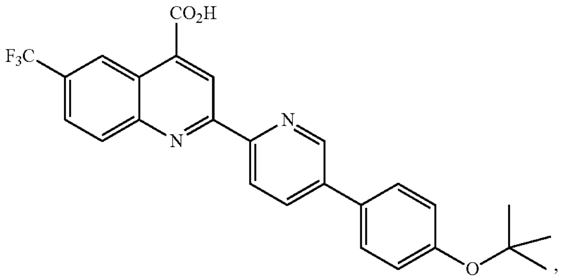,
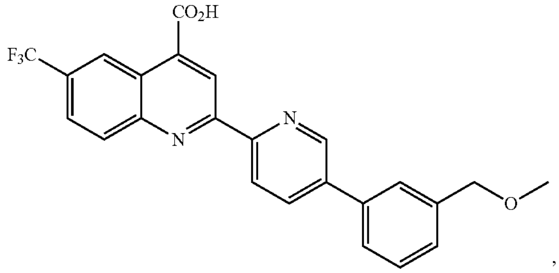,
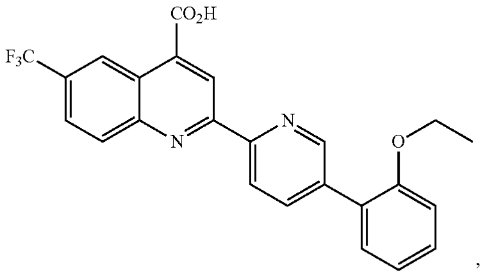,
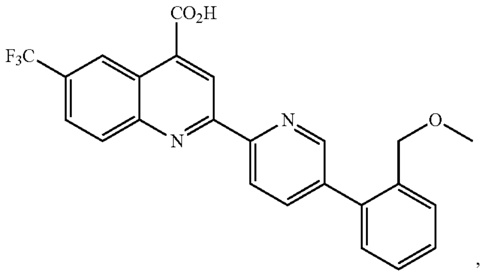, -continued
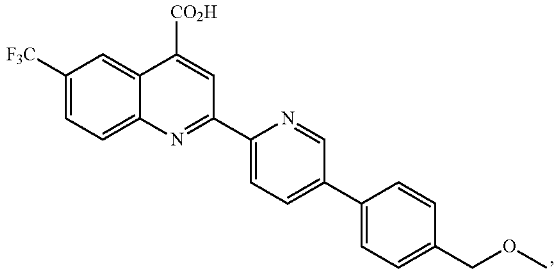
,
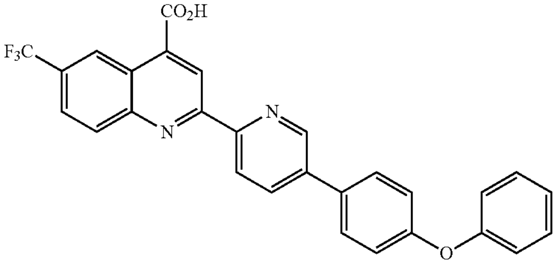
,
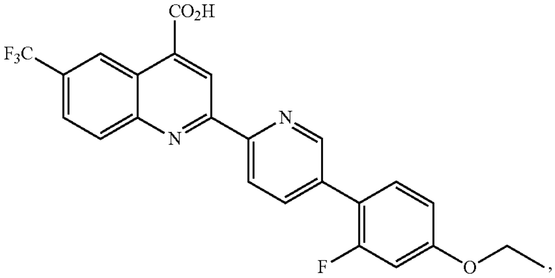
,
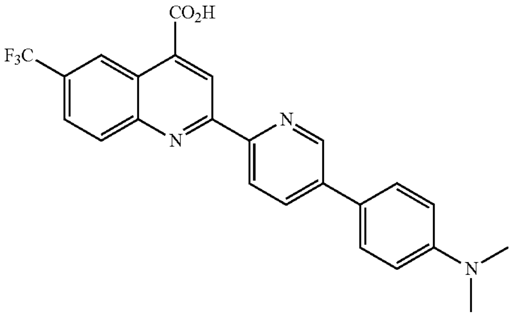
,
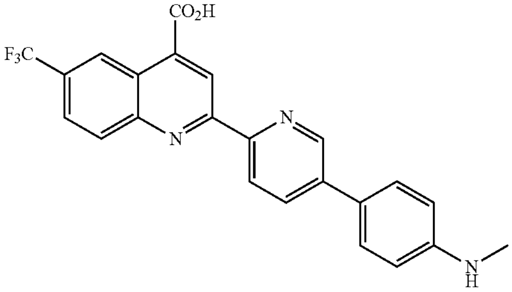
,
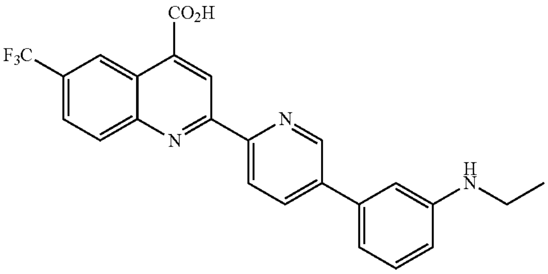
,
-continued
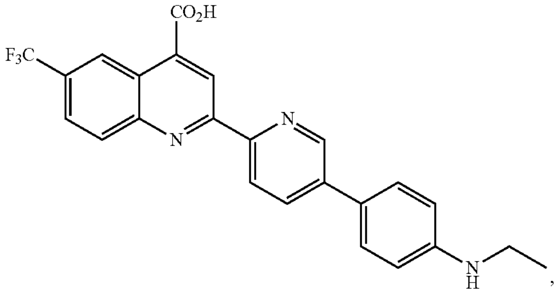
,
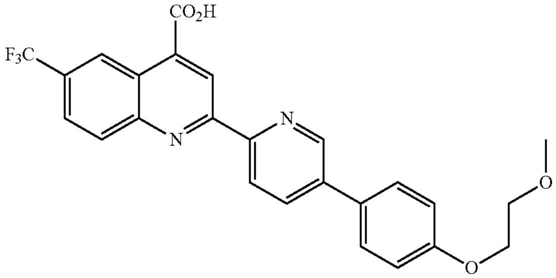
,
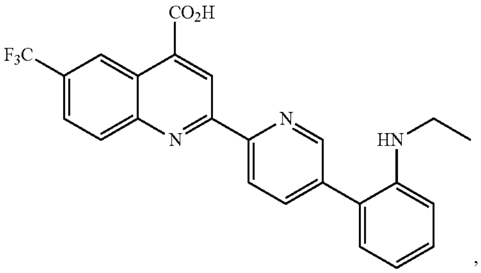
,
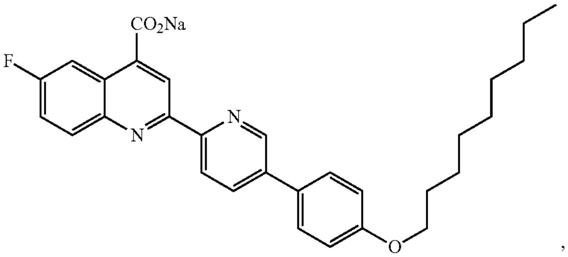
,
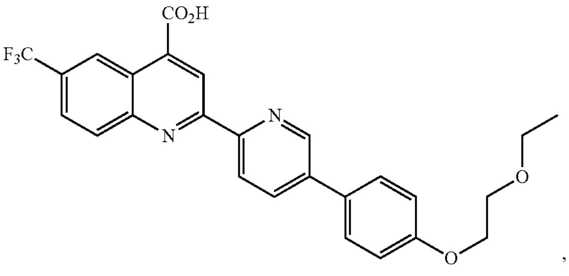
,
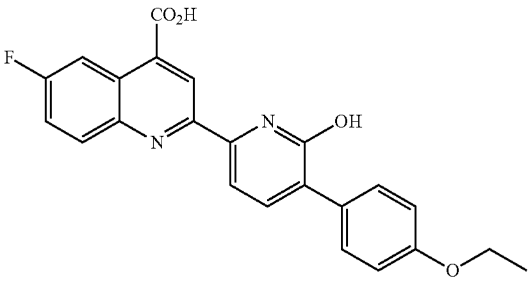
, -continued

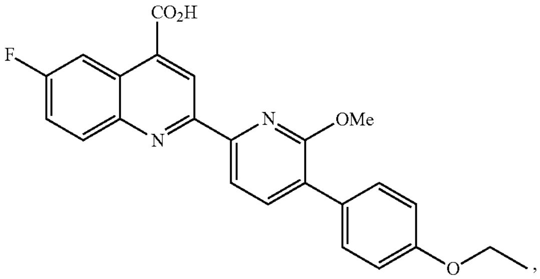
,

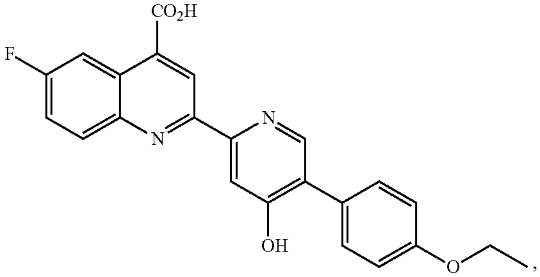
,

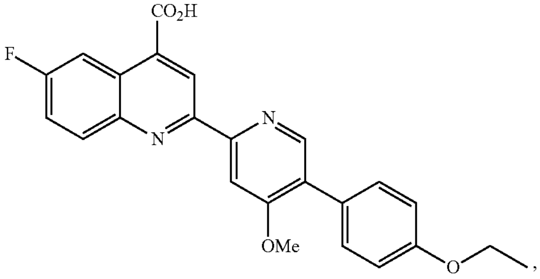
,

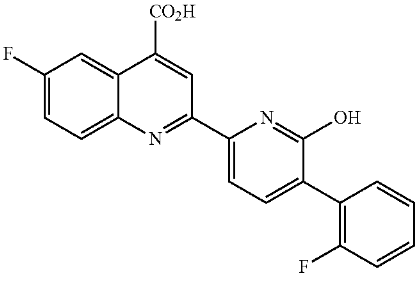
,

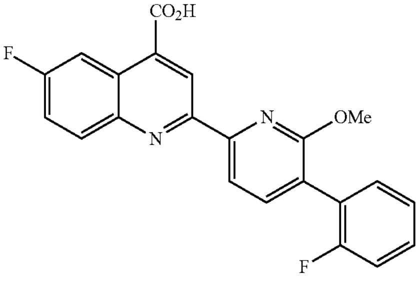
,

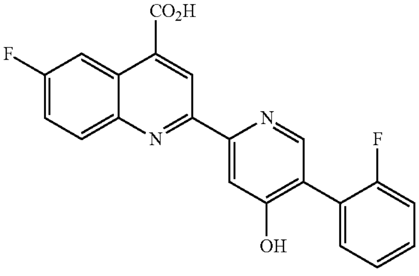
,

-continued

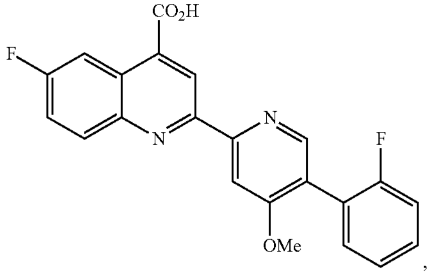
,

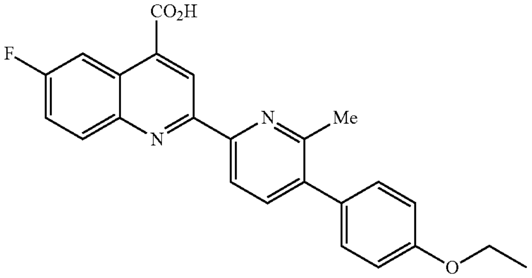
,

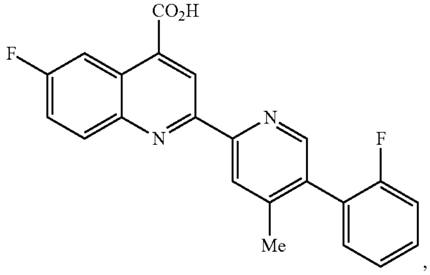
, or a subgroup thereof.

In various aspects, it is contemplated herein that the disclosed compounds further comprise their biosteric equivalents. The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience; New York, 1970, 64-80; (ii) Burger, A.; "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", *Perspect. Drug Discovery Des.* 1998, 9/10/11, 213-224; (v) Koyanagi T, Haga T, "Bioisosterism in agrochemicals", *ACS Symp. Ser.* 1995, 584, 15-24; (vi) Kubinyi H, "Molecular similarities. Part 1. Chemical structure and biological activity", *Pharm. UnsererZeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J, "Bioisosteric approach in the design of new dopaminergic/serotonergic ligands", *Cur. Med. Chem.* 1998, 5, 493-512 (x) Thornber C W, "Isosterism and molecular modification in drug design", *Chem. Soc. Rev.* 1979, 8, 563-80.

In further aspects, bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere.

The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

In various aspects, it is contemplated herein that the disclosed compounds further comprise their isotopically-labelled or isotopically-substituted variants, i.e., compounds identical to those described, but for the fact that one or more atoms are replaced by an atom having an atomic mass or mass number different from the atomic mass or mass number typically found in nature. Examples of isotopes that can be incorporated into compounds of the disclosure include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively.

Compounds further comprise prodrugs thereof, and pharmaceutically acceptable salts of said compounds or of said prodrugs which contain the aforementioned isotopes and/or other isotopes of other atoms are within the scope of this disclosure. Certain isotopically-labelled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present disclosure and prodrugs thereof can generally be prepared by carrying out the procedures below, by substituting a readily available isotopically labelled reagent for a non-isotopically labelled reagent.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

In various aspects, the disclosed compounds can be in the form of a co-crystal. The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Preferred co-crystals include p-toluenesulfonic acid and benzenesulfonic acid.

The term "pharmaceutically acceptable co-crystal" means one that is compatible with the other ingredients of the formulation and not deleterious to the recipient thereof.

In a further aspect, the disclosed compounds can be isolated as solvates and, in particular, as hydrates of a disclosed compound, which can be obtained, for example, by crystallization from a solvent or from aqueous solution. In this connection, one, two, three or any arbitrary number of solvate or water molecules can combine with the compounds according to the disclosure to form solvates and hydrates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulfuric acid and phosphoric acid and such organic acids as oxalic acid, maleic acid, succinic acid and citric acid. In a further aspect, salts further include, but are not limited, to the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e., 1,1'-methylene-bis-(2-hydroxy-3-naphthoate)) salts. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The disclosed compounds can be conveniently utilized as a component of a degrader molecule. Accordingly, in various aspects, a disclosed compound can be used as a ligand, a linker, or an adjoining chemical structure within a proteolysis targeting complex or targeted protein degrader complex. For example, Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Bondeson and Crews, Annu Rev Pharmacol Toxicol. 2017 Jan. 6; 57: 107-123; Lai et al. Angew Chem Int Ed Engl. 2016 Jan. 11; 55(2): 807-810; and PCT Appl. No. PCT/US2018/061573).

In a further aspect, the disclosed compounds can further comprise linkage to a PROteolysis-TArgeting Chimera (PROTAC), thereby providing interaction with the intracellular ubiquitin-proteasome system to selectively degrade target protein. For example, in some instances, any one or more compounds can be utilized to form a composition, chimera, fusion, or complex having a protein degrading function. Some exemplary complexes can include a proteolysis-targeting chimaera (PROTAC) or a degronimid. As understood by a skilled artisan, such a complex is capable of uniting or combining cellular processes related to protein degradation to a specific target protein, wherein the cellular machinery and the target protein are complexed by a ligand, a linker, or an adjoining chemical structure.

Methods of Making the Compounds.

In one aspect, the present disclosure relates to methods of making compounds useful as inhibitors of dihydroorotate dehydrogenase (DHODH), which can be useful in the treatment of clinical conditions, diseases, and disorders associated with DHODH dysfunction and other diseases in which DHODH is involved. In one aspect, the disclosure relates to the disclosed synthetic manipulations. In a further aspect, the disclosed compounds comprise the products of the synthetic methods described herein. In a further aspect, the disclosed compounds comprise a compound produced by a synthetic method described herein. In a still further aspect, the disclosure comprises a pharmaceutical composition comprising a therapeutically effective amount of the product of the disclosed methods and a pharmaceutically acceptable carrier. In a still further aspect, the disclosure comprises a method for manufacturing a medicament comprising combining at least one compound of any of disclosed compounds or at least one product of the disclosed methods with a pharmaceutically acceptable carrier or diluent.

The compounds of this disclosure can be prepared by employing reactions as shown in the disclosed schemes, in addition to other standard manipulations that are known in the literature, exemplified in the experimental sections or clear to one skilled in the art. The following examples are provided so that the disclosure might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the disclosure. It is understood that a disclosed method can be used to provide the disclosed compounds. It is also understood that the products of the disclosed methods can be employed in the disclosed compositions, kits, and uses.

In one aspect, substituted 6-substituted-2-(phenylheteroaryl)quinoline-4-carboxylic acid analogs of the present disclosure can be prepared generically by the synthetic scheme as shown below.

Step 1(Suzuki-Miyaura Reaction).

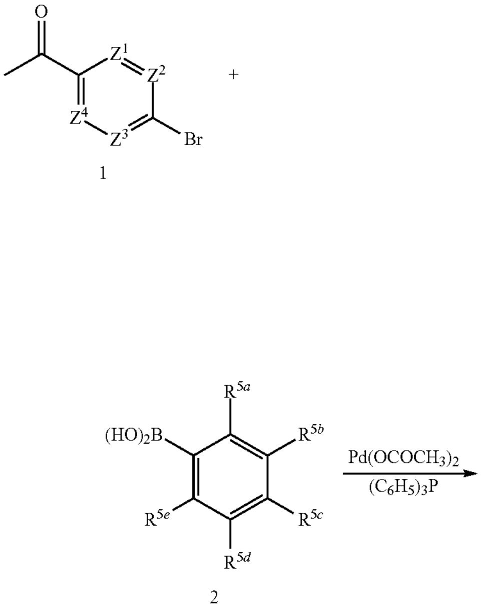

-continued

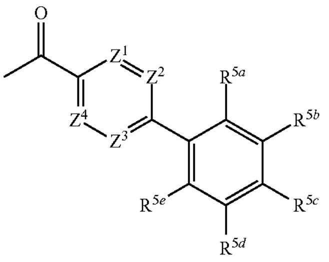

3

Step 2 (Pfitzinger Reaction).

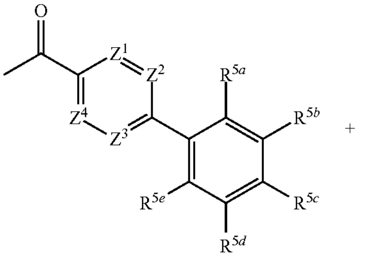

3

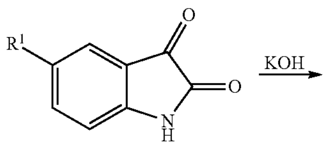

4

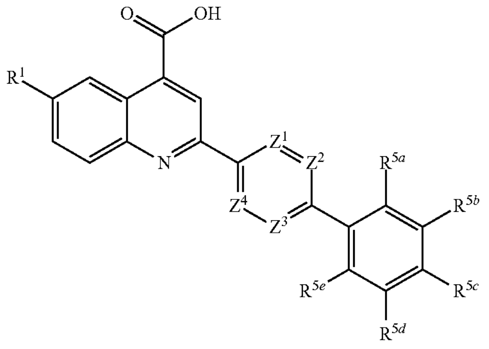

5

Compounds are represented in generic form, with substituents as noted in compound descriptions elsewhere herein. A more specific example is set forth below.

Step 1 (Suzuki-Miyaura Reaction)

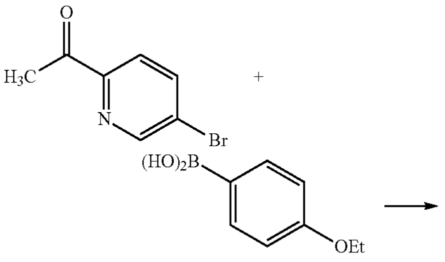

-continued

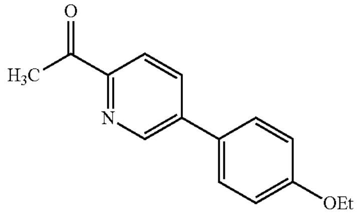

Step 2 (Pfitzinger Reaction)

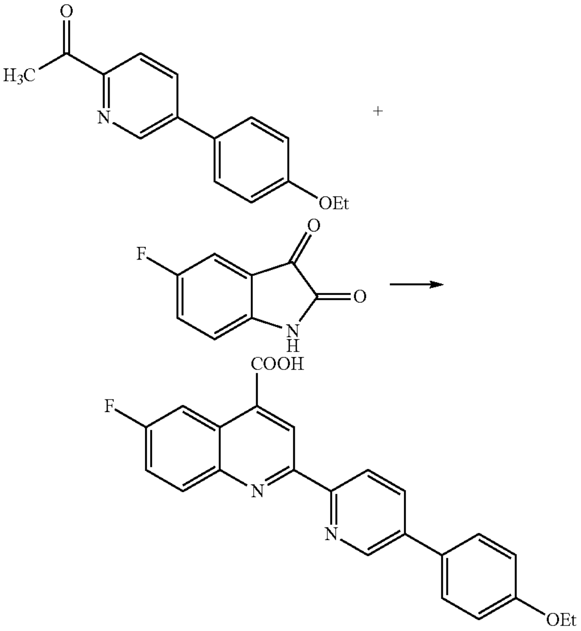

In one aspect, compounds of the present disclosure, e.g. compounds of Formula 5 can be prepared in a two-step reaction as shown above. Briefly, the synthesis of compound of Formula 5 begins in Step 1 with reaction of compounds of Formulas 1 and 2 to yield compounds of Formula 3. Compounds of Formula 1, i.e., 4-halosubstituted heteroaryl ethanone analogs, e.g., 1-(5-bromopyridin-2-yl)ethan-1-one, and Formula 2, i.e., appropriately substituted phenylboronic acids, e.g., 4-ethoxyphenylboronic acid, can be obtained from commercial sources or can be readily prepared by one skilled in the art according to methods described in the literature. For example, both 1-(5-bromopyridin-2-yl)ethan-1-one and 4-ethoxyphenylboronic acid are available commercially. The reaction of reaction of compounds of Formulas 1 and 2 is typically carried at a molar ratio of Formula 1 compound to Formula 2 compound of about 25:1 to about 1:1 out in a suitable solvent, e.g., 1-propanol, in the presence of palladium acetate and triphenylphosphine, at a suitable temperature, e.g. about 75° C. to about 200° C., for a suitable period of time, e.g. about 10 minutes to about 2 hours, in order to ensure that the reaction is complete. The reaction is then cooled to a suitable temperature, e.g., room temperature, and then can be further cooled, e.g., to about 0° C. to obtain suitable crystals, which can collected by filtration. Other suitable methods of isolating the product will be apparent to one skilled in the art.

In Step 2, the compound of Formula 3, isolated from Step 1, is reacted with compounds of Formula 4 to yield the desired disclosed compound of Formula 5 as shown above. Briefly, a mixture of the appropriate isatin, i.e., a compound of Formula 4, e.g., 5-fluoroisatin (5-fluoroindoline-2,3-dione), and a suitable base, e.g., aqueous potassium hydroxide solution (33%), are stirred and heated gently. To this solution, the slurry of a compound of Formula 3, e.g., 1-(5-(4-ethoxyphenyl)pyridin-2-yl)ethan-1-one, in an amount of about equimolar to the compound of Formula 4, and a suitable solvent is used to prepare the slurry, e.g., ethanol. The reaction mixture is then heated to a suitable temperature, e.g., reflux or about 70° C. to about 200° C., for a suitable period of time, e.g., about 10 minutes to about 3 hours, in order to ensure that the reaction is complete. The reaction is then cooled to a suitable temperature, e.g., room temperature, and then can be further cooled, e.g., to about 0° C. to obtain suitable crystals, which can collected by filtration. Other suitable methods of isolating the product will be apparent to one skilled in the art. The product may also be further purified if residual solvent is present, e.g., as described herein below in the Examples.

Pharmaceutical Compositions.

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_3O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer, glutaminic acid/glutamic acid ester copolymer carboxymethylethylcellulose glycerol monooctanoate; cellulose acetate succinate; polyarginine; and the like.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and dibutylsebacate, dibutylsuccinate, dibutyltartrate; diethylene glycol dipropionate; ethyleneglycol diacetate, dibutyrate, dipropionate; tributyl phosphate, tributyrin; polyethylene glycol sorbitan monooleate (polysorbates such as Polysorbate 50); sorbitan monooleate; and the like.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 mole ethylene oxide per 1 mole glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylenediaminetetracetic acid, nitrilotriacetic acid, diethylenetriaminepentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present disclosure may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present disclosure include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present disclosure therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present disclosure include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the disclosure formulated in a pharmaceutically acceptable carrier may also be prepared, placed in an appropriate container, and labeled for treatment of an indicated condition.

Another patch system configuration which can be used by the present disclosure is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present disclosure is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require of inhibition dihydroorotate dehydrogenase activity an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for modulating dihydroorotate dehydrogenase activity (e.g., treatment of one or more disorders, such as a cancer or a graft-versus-host-disease, that can be treated via inhibition of dihydroorotate dehydrogenase dysfunction activity) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and a therapeutic agent that can be used to treat autoimmune diseases, immune and inflammatory diseases, destructive bone disorders, malignant neoplastic diseases, angiogenic-related disorders, viral diseases, and infectious diseases. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

Methods of Using the Compounds.

In a further aspect, the present disclosure provides methods of treatment comprising administration of a therapeutically effective amount of a disclosed compound or pharmaceutical composition as disclosed herein above to a subject in need thereof. In particular, the disclosed compounds and disclosed pharmaceutical compositions can be used in methods of treating a disease or disorder that are associated with increased, aberrant, or dysfunctional levels of dihydroorotate dehydrogenase (DHODH) activity in a cell, tissue, or organism. That is, the disclosed compounds and disclosed pharmaceutical compositions can be used to inhibit DHODH activity in a cell, tissue or organism to provide a clinical or therapeutic benefit to a subject which has been determined to or been diagnosed to have with increased, aberrant, or dysfunctional levels of dihydroorotate dehydrogenase (DHODH) activity.

In some aspects of the disclosed methods, the subject has been diagnosed with a need for treatment prior to the administering step. In some aspects of the disclosed method, the subject has been diagnosed with a disorder treatable by inhibition of DHODH and/or a need for inhibition of DHODH prior to the administering step. In some aspects of the disclosed method, the subject has been diagnosed with a cancer, a disorder associated with T-cell proliferation, or a may be at risk for graft-versus-host disease or organ rejection following transplantation prior to the administering step. In some aspects of the disclosed methods, the subject has been identified with a need for treatment prior to the administering step.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

DHODH is an enzyme that catalyzes the fourth step in the de novo biosynthesis of pyrimidine. It converts dihydroorotate (DHO) to orotate (ORO). Human DHODH is a ubiquitous flavine mononucleotide (FMN) moiety flavoprotein. In a mammalian cell, DHODH is anchored at the inner mitochondrial leaflet and catalyzes the conversion of DHO to ORO, which represents the rate limiting step in the de novo pyrimidine biosynthesis. Kinetic studies indicate a sequential ping-pong mechanism for the conversion of DHO to ORO (e.g., see Knecht et al., Chem. Biol. Interact. 2000, 124, 61-76). The first half-reaction comprises the reduction of DHO to ORO. Electrons are transferred to the FMN which becomes oxidized to dihydroflavin mononucleotide (FMNH2). After dissociation of ORO from the enzyme, FMNH2 is regenerated by a ubiquinone molecule, which is recruited from the inner mitochondrial membrane. Kinetic and structural studies revealed two distinct binding sites for DHO/ORO and ubiquinone, respectively.

Human DHODH is composed of two domains, a large C-terminal domain (Met78-Arg396) and a smaller N-terminal domain (Met30-Leu68), connected by an extended loop. The large C-terminal domain can be best described as an $\alpha/\beta$-barrel fold with a central barrel of eight parallel $\beta$ strands surrounded by eight a helices. The redox site, formed by the substrate binding pocket and the site that binds the cofactor FMN, is located on this large C-terminal domain. The small N-terminal domain, on the other hand, consists of two a helices (labeled $\alpha 1$ and $\alpha 2$), both connected by a short loop. This small N-terminal domain harbors the binding site for the cofactor ubiquinone. The helices $\alpha 1$ and $\alpha 2$ span a slot of about 10×20 Å2 in the so-called hydrophobic patch, with the short $\alpha 1$-$\alpha 2$ loop at the narrow end of that slot. The slot forms the entrance to a tunnel that ends at the FMN cavity nearby the $\alpha 1$-$\alpha 2$ loop. This tunnel narrows toward the proximal redox site and ends with several charged or polar side chains (Gln47, Tyr356, Thr360, and Arg136). Structural clues, as discussed above, along with kinetic studies suggest that ubiquinone, which can easily diffuse into the mitochondrial inner membrane, uses this tunnel to approach the FMN cofactor for the redox reaction (e.g., see Baumgartner et al., J. Med. Chem. 2006, 49, 1239-1247).

In an organism, DHODH catalyzes the synthesis of pyrimidines, which are necessary for cell growth. An inhibition of DHODH inhibits the growth of (pathologically) fast proliferating cells, whereas cells which grow at normal speed may obtain their required pyrimidine bases from the normal metabolic cycle. The most important types of cells for the immune response, the lymphocytes, use exclusively the synthesis of pyrimidines for their growth and react particularly sensitively to DHODH inhibition.

DHODH inhibition results in decreased cellular levels of ribonucleotide uridine monophosphate (rUMP), thus arresting proliferating cells in the GI phase of the cell cycle. The inhibition of de novo pyrimidine nucleotide synthesis is of great interest in view of the observations that lymphocytes seem not to be able to undergo clonal expansion when this pathway is blocked. Substances that inhibit the growth of lymphocytes are important medicaments for the treatment of auto-immune diseases.

During homeostatic proliferation, the salvage pathway which is independent of DHODH seems sufficient for the cellular supply with pyrimidine bases. Only, cells with a high turnover and particularly T and B lymphocytes need the de novo pathway to proliferate. In these cells, DHODH inhibition stops the cell cycle progression suppressing DNA synthesis and consequently cell proliferation.

Therefore, inhibitors of DHODH show beneficial immunosuppressant and antiproliferative effects in human diseases characterized by abnormal and uncontrollable cell proliferation causing chronic inflammation and tissue destruction. The human enzyme dihydroorotate dehydrogenase (DHODH) represents a well-characterized target for small molecular weight Disease Modifying Antirheumatic Drugs (DMARDs).

Accordingly, in various aspects, the present disclosure pertains to methods of treating a variety of diseases or disorders, including, but not limited to, autoimmune diseases, immune and inflammatory diseases, destructive bone disorders, cancers and malignant neoplastic diseases, angiogenic-related disorders, viral diseases, and infectious diseases.

In a further aspect, the present disclosure pertains to a methods for treating an immunological disorder, inflammatory disorder, cancer or other proliferative disease via inhibition of DHODH by administering to a subject in need of such treatment an effective amount of at least one disclosed compound or at least one disclosed pharmaceutical composition.

In a further aspect, the present disclosure pertains to method for treating an immunological disorder, inflammatory disorder, cancer or other proliferative disease via inhibition of DHODH by administering to a patient in need of such treatment an effective amount of at least one disclosed compound or at least one disclosed pharmaceutical composition in combination (simultaneously or sequentially) with at least one other anti-inflammatory, immunomodulator or anti-cancer agent.

In various aspects, an autoimmune disorder or disease that can be treated by the disclosed compounds or disclosed pharmaceutical compositions include, but are not limited, one selected from lupus, rheumatoid arthritis, ankylosing spondylitis, glomerulonephritis, minimal change disease, ulcerative colitis, crohns disease, addison's disease, adult Still's disease, alopecia areata, autoimmune hepatitis, autoimmune angioedema, Bechet's disease, pemphigoid and variants, celiac disease, chronic inflammatory demyelinating polyneuropathy, churg-Straus syndrome, Crest syndrome, dermatomyositis, neuromyelitis optica, discoid lupus, fibromyalgia, giant cell arteritis, giant cell myocarditis, Goodpasteur's disease, evan's syndrome, autoimmune hemolytic anemia, immune thrombocytopenia, Henoch-Schonlein purpura, IgA nephropathy, IgG4 related sclerosing disease, juvenile arthritis, juvenile diabetes, Kawasaki disease, Leukocytoclastic vasculitis, mixed connective disease, multiple sclerosis, multifocal motor neuropathy, myasthenia gravis, autoimmune neutropenia, optic neuritis, peripheral neuropathy, POEMS syndrome, polymyositis, primary biliary cirrhosis, non-alcoholic hepatosteotosis and associated cirrhosis, psoriasis, scleroderma, sarcoidosis, temporal arteritis, vasculitis, and uveitis.

In a further aspect, autoimmune diseases that can be treated by the disclosed compounds or disclosed pharmaceutical compositions include, but are not limited, to rheumatoid arthritis, psoriatic arthritis, systemic lupus erythematosus, multiple sclerosis, psoriasis, ankylosing spondilytis, Wegener's granulomatosis, polyarticular juvenile idiopathic arthritis, inflammatory bowel disease such as ulcerative colitis and Crohn's disease, Reiter's syndrome, fibromyalgia and type-1 diabetes.

Immune and inflammatory diseases that can be treated by the disclosed compounds or disclosed pharmaceutical compositions include, but are not limited, to asthma, COPD, respiratory distress syndrome, acute or chronic pancreatitis, graft versus-host disease, chronic sarcoidosis, transplant rejection, contact dermatitis, atopic dermatitis allergic rhinitis, allergic conjunctivitis, Behçet's syndrome, inflammatory eye conditions such as conjunctivitis and uveitis.

In various aspects, the present disclosure pertains to methods for treating organ rejection diseases or ameliorating and/or preventing organ rejection diseases in patients predisposed to organ rejection by administering to a patient in need of such treatment an effective amount of at least one disclosed compound or disclosed pharmaceutical composition. In a further aspect, the patient has received an organ transplant or is diagnosed as requiring an organ transplant. In a still further aspect, the organ transplant can include, but is not limited to, a transplanted organ of the kidney, liver, skin, heart, pancreas, lung, or combinations thereof.

In various aspects, the present disclosure pertains to methods for treating EBV viral lymphoproliferation in the setting of tumor immunosuppression. In a further aspect, the method of treating EBV viral lymphoproliferation can be to provide both continued organ transplantation preservation and also treatment of the underlying EBV lymphoproliferation.

Destructive bone disorders that can be treated by the disclosed compounds or disclosed pharmaceutical compositions include, but are not limited, to osteoporosis, osteoarthritis and multiple myeloma-related bone disorder.

Cancers and malignant neoplastic that can be treated by the disclosed compounds or disclosed pharmaceutical compositions include, but are not limited, to prostate, ovarian and brain cancer. Carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Angiogenesis-related disorders that can be treated by the disclosed compounds or disclosed pharmaceutical compositions include, but are not limited, to hemangiomas, ocular neovascularization, macular degeneration or diabetic retinopathy.

Viral diseases that can be treated by the disclosed compounds or disclosed pharmaceutical compositions include, but are not limited, to HIV infection, hepatitis and cytomegalovirus infection.

Infectious diseases that can be treated by the disclosed compounds or disclosed pharmaceutical compositions include, but are not limited, to sepsis, septic shock, endotoxic shock, Gram negative sepsis, toxic shock syndrome, Shigellosis and other protozoal infestations such as malaria.

In further aspects, the disclosed compounds or disclosed pharmaceutical compositions can act as modulators of apoptosis, and accordingly, can be useful in the treatment of cancer (including but not limited to those types mentioned herein above), viral infections (including but not limited to herpes virus, poxyirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

In further aspects, the disclosed compounds or disclosed pharmaceutical compositions can act to modulate the level of cellular RNA and DNA synthesis. Accordingly, the disclosed compounds and disclosed pharmaceutical compositions can be used in the treatment of viral infections (including but not limited to HIV, human papilloma virus, herpesvirus, poxyirus, Epstein-Barr virus, Sindbis virus and adenovirus).

In further aspects, the disclosed compounds or disclosed pharmaceutical compositions can be used in the chemoprevention of cancer. Chemoprevention is understood to be a clinical intervention to inhibit the development of invasive cancer by either blocking the initiating mutagenic event or by blocking the progression of pre-malignant cells that have already suffered an insult or inhibiting tumor relapse. Accordingly, the disclosed compounds and disclosed pharmaceutical compositions can be used in inhibiting tumor angiogenesis and metastasis.

In further aspects, the disclosed compounds and disclosed pharmaceutical compositions can also be combined with other active compounds in the treatment of diseases wherein the inhibition of DHODH is known to show beneficial effect.

In various aspects, the diseases, conditions or disorders that can benefit from inhibition of DHODH include, but are not limited to, an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, hepatic diseases or disorders, renal diseases or disorders.

In a further aspect, the disclosed compounds and disclosed pharmaceutical compositions can be used as immunosuppressants to prevent transplant graft rejections, allogeneic or xenogeneic transplantation rejection (organ, bone marrow, stem cells, other cells and tissues), and graft-versus-host disease. In other embodiments, transplant graft rejections result from tissue or organ transplants. In further embodiments, graft-versus-host disease results from bone marrow or stem cell transplantation.

In a further aspect, the disclosed compounds and disclosed pharmaceutical compositions can be used in the treatment of a variety of inflammatory diseases including, but not limited to, inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, corneal transplant rejection, lupus erythematosus, systemic lupus erythematosus, proliferative lupus nephritis, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma and Sjogren's syndrome.

In a further aspect, the disclosed compounds and disclosed pharmaceutical compositions can be used in the treatment of a variety of diseases including Felty's syndrome, Wegener's granulomatosis, Crohn's disease, sarcoidosis, Still's disease, pemphigoid, Takayasu arteritis, systemic sclerosis, relapsing polychondritis, refractory IgA nephropathy, SAPHO2 syndrome (SAS), cytomegalovirus infection including rhinitis or cyst, psoriasis, IGG4 disease, and multiple myeloma.

In a further aspect, the disclosed compounds and disclosed pharmaceutical compositions can be used in combination (administered together or sequentially) with known anti-cancer treatments such as radiation therapy or with cytostatic or cytotoxic or anticancer agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; BTK inhibitors, SYK inhibitors, ITK inhibitors, PI3-kinase inhibitors, FLT3 inhibitors, EGF inhibitors; PAK inhibitors, VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well. These agents can be used in combination with differentiation agents such as ATRA, EZH2 inhibitors, DNMT inhibitors, corticosteroids, IDH1 inhibitors, IDH2 inhibitors, and Vitamin C. These agents can be used in combination with small molecules that enhance DNA damage killing in cancer cells including PARP inhibitors, MDM2 inhibitors, NAMPT inhibitors, and HSP90 inhibitors. These agents can be used in combination with antibodies that target cell surface molecules on immune or cancer cells including but not limited to CD33, CD37, CD19, CD20, CD3, CD123, CD70, BAFFR, CD4, CD8, CD56, and CD38. These agents can be used in combination with antibodies or peptides which neutralize cytokines including, but not limited to IL1Beta, IL6, IL10, IL21, TNFA, TNFB, and IFN. These agents can be used in combination with cellular CAR-T cells to diminish cellular proliferation in the setting of significant cytokine release syndrome and neurotoxicity. These agents can be used to diminish T-cell proliferation, cytokine production, and neurotoxicity in combination with bi-specific antibodies or peptide molecules that target in a dual manner T-cells and immune/tumor cell antigens such as, but not limited to CD19, CD20 CD33, CD123, CD38, and CD37. These agents can be used to diminish T-cell proliferation and tissue damage caused by immune check point inhibitor antibodies to targets such as, but not limited to PD1, PDL1, CTLA4, and LAG3.

In a further aspect, diseases, disorders or conditions that can be treated or prevented using the disclosed compounds and disclosed pharmaceutical compositions are capable of inhibiting DHODH, and accordingly, useful in the treatment of diseases, conditions or disorders involving inflammation and/or that are related to the immune system. These diseases include, but are not limited, to asthma, chronic obstructive pulmonary disease, rheumatoid arthritis, inflammatory bowel disease, glomerulonephritis, neuroinflammatory diseases such as multiple sclerosis, and disorders of the immune system.

In a further aspect, the disclosed compounds and disclosed pharmaceutical compositions can be used for treating immune and immune-related disorders, including, for example, chronic immune diseases/disorders, acute immune diseases/disorders, autoimmune and immunodeficiency diseases/disorders, diseases/disorders involving inflammation, organ transplant graft rejections and graft-versus-host disease and altered (e.g., hyperactive) immune responses. In a still further aspect, other exemplary immune disorders that can be treated using the disclosed compounds and disclosed pharmaceutical compositions include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Chronic graft-versus-host disease (cGVHD) is a primary cause of nonrelapse mortality after allogeneic hematopoietic stem cell transplantation (HSCT) (Baird K, Pavletic S Z. Curr Opin Hematol. 2006; 13(6):426-435; Lee S J, Vogelsang G, Flowers M E. Biol Blood Marrow Transplant. 2003; 9(4):215-233; Pidala J, et al. Blood. 2011; 117(17):4651-4657; and Arai S, et al. Blood. 2011; 118(15):4242-4249). Drug therapy for cGVHD has been predominantly limited to steroids and calcineurin inhibitors, which are incompletely effective and associated with infections as well as long-term risks of toxicity (Holler, E. Best Pract Res Clin Haematol. 2007; 20(2):281-294). The disclosed compounds can be used for the treatment of cGVHD.

Kits.

In various aspects, the present disclosure pertains to kits comprising a therapeutically effective amount of at least one disclosed compound, a disclosed product of the methods of making a disclosed compound, or a pharmaceutically acceptable salt thereof, or a disclosed pharmaceutical composition; and: at least one agent known to treat a cancer, a host-versus-graft-disease, and/or a disorder associated with T-cell proliferation; and instructions for treating a cancer, a host-versus-graft-disease, and/or a disorder associated with T-cell proliferation.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present disclosure also features such kits further containing instructions for use.

In a further aspect, the present disclosure also provides a pharmaceutical pack or kit comprising one or more containers filled with one or more of the ingredients of the pharmaceutical compositions of the disclosure. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

Research Tools.

The disclosed compounds and pharmaceutical compositions have activity as inhibitors of DHODH activity or inhibitors of cell proliferation. As such, the disclosed compounds are also useful as research tools. Accordingly, one aspect of the present disclosure relates to a method of using a compound of the disclosure as a research tool, the method comprising conducting a biological assay using a compound of the disclosure. Compounds of the disclosure can also be used to evaluate new chemical compounds. Thus another aspect of the disclosure relates to a method of evaluating a test compound in a biological assay, comprising: (a) conducting a biological assay with a test compound to provide a first assay value; (b) conducting the biological assay with a compound of the disclosure to provide a second assay value; wherein step (a) is conducted either before, after or concurrently with step (b); and (c) comparing the first assay value from step (a) with the second assay value from step (b). Exemplary biological assays include an in vitro DHODH enzymatic assay or in a cell culture-based assay measuring cell proliferation. Methods suitable for carrying out such assays are described herein. Still another aspect of the disclosure relates to a method of studying a biological system, e.g., a model animal for a clinical condition, or biological sample comprising a DHODH protein, the method comprising: (a) contacting the biological system or sample with a compound of the disclosure; and (b) determining the effects caused by the compound on the biological system or sample.

Aspects.

The following listing of exemplary aspects supports and is supported by the disclosure provided herein.

Aspect 1. A compound having a formula represented by a structure:

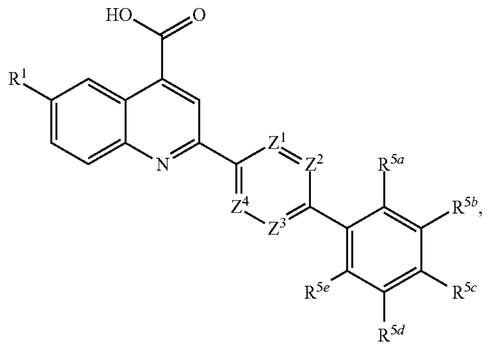

wherein each of $Z^1$, $Z^2$, $Z^3$, and $Z^4$ is independently selected from CH and N; wherein $R^1$ is selected from hydrogen, halogen, —$SF_5$, —CN, —$N_3$, —OH, —$NH_2$, —$CF_3$, and —$CF_2CF_3$; wherein one of $R^{5a}$, $R^{5b}$, $R^{5c}$, $R^{5d}$, and $R^{5e}$ is selected from a group having formula represented by a structure: —$R^{20}$, —$R^{30}$-$A^1$-$R^{40}$, -A-$R^{40}$, -$A^1$-$R^3$-$A^2$-$R^{40}$, or -$A^1$-$R^{30}$-$A^2$-$R^{31}$-$A^3$-$R^{40}$; wherein $A^1$ is selected from —O— and —$NR^{50}$—; wherein $R^{50}$ is selected from hydrogen, —C1-C10 alkyl, —C1-C10 aminoalkyl, and —C1-C10 hydroxyalkyl; wherein $A^2$ is selected from —O— and —$NR^{60}$—; wherein $R^{80}$ is selected from hydrogen, —C1-C10 alkyl, —C1-C10 aminoalkyl, and —C1-C10 hydroxyalkyl; wherein $A^3$ is selected from —O— and —$NR^{70}$—; wherein $R^{70}$ is selected from hydrogen, —C1-C10 alkyl, —C1-C10 aminoalkyl, and —C1-C10 hydroxyalkyl; wherein $R^{20}$ is selected from halogen, —C1-C10 alkyl, —C1-C10 haloalkyl, —C1-C10 hydroxyalkyl, —C1-C10 alkylamino, and —C1-C10 alkoxy; wherein each of $R^{30}$ and $R^{31}$ is independently selected from —C1-C10 alkanediyl, —C1-C10 haloalkanediyl, —C1-C10 aminoalkanediyl, and —C1-C10 hydroxyalkanediyl; and wherein $R^{40}$ is selected from —C1-C10 alkyl, —C1-C10 haloalkyl, —C1-C10 aminoalkyl, —C1-C10 hydroxyalkyl, and —$(CH_2)_n$$AR^1$; wherein n is an integer selected from 1, 2, and 3; and wherein $AR^1$ is a phenyl group substituted with 0, 1, 2, 3, 4, or 5 groups independently selected from halogen, —$SF_5$, —CN, —$N_3$, —OH, —$NH_2$, —C1-C4 alkyl, —C1-C4 alkoxy, —C1-C4 haloalkyl, —C1-C4 aminoalkyl, —C1-C4 alkylamino, —C1-C4 haloalkylamino, —C1-C4 hydroxyalkyl, —C1-C4 halohydroxyalkyl, cycloalkyl, and heterocycloalkyl; and wherein four of $R^{5a}$, $R^{5b}$, $R^{5c}$, $R^{5d}$, and $R^{5e}$ are independently selected from hydrogen, halogen, —$SF_5$, —CN, —$N_3$, —OH, —$NH_2$, —$CF_3$, and —$CF_2CF_3$; or a pharmaceutically acceptable salt thereof.

Aspect 2. The compound of Aspect 1, wherein $R^1$ is selected from halogen, —$SF_5$, —$CF_3$, and —$CF_2CF_3$.

Aspect 3. The compound of Aspect 2, wherein $R^1$ is halogen.

Aspect 4. The compound of Aspect 3, wherein $R^1$ is F or Cl.

Aspect 5. The compound of Aspect 3, wherein $R^1$ is F.

Aspect 6. The compound of Aspect 2, wherein $R^1$ is selected from —$SF_5$, —$CF_3$, and —$CF_2CF_3$.

Aspect 7. The compound of Aspect 2, wherein $R^1$ is —$SF_5$.

Aspect 8. The compound of any one of Aspect 1-Aspect 7, wherein $R^{5c}$ is halogen, C1-C7 haloalkyl, or —O(C1-C7 haloalkyl).

Aspect 9. The compound of Aspect 8, wherein $R^{5c}$ is halogen.

Aspect 10. The compound of Aspect 9, wherein $R^{5c}$ is F.

Aspect 11. The compound of Aspect 8, wherein $R^{5c}$ is —$OCF_3$, —$OCH_2CF_3$, or —$OCF_2CF_3$.

Aspect 12. The compound of any one of Aspect 1-Aspect 7, wherein $R^{50}$ is —OH, —O(C1-C7 alkyl), —C1-C7 hydroxyalkyl, —O—(C1-C7 hydroxyalkyl), —$CH_2$O(C1-C7 alkyl), or —$(CH_2)_2$O(C1-C7 alkyl).

Aspect 13. —O(C1-C7 alkyl), —(C1-C7 alkanediyl)-OH, —O(C1-C7 alkanediyl)-OH, —$CH_2$O(C1-C7 alkyl), or —$(CH_2)_2$O(C1-C7 alkyl).

Aspect 14. The compound of Aspect 13, wherein $R^{5c}$ is —$OCH_3$, —$OCH_2CH_3$, —$O(CH_2)_2CH_3$, —$OCH(CH_3)_2$, —$O(CH_2)_3CH_3$, —$OCH_2CH(CH_3)_2$, —$OCH(CH_2CH_3)(CH_3)$, —$CH_2OH$, —$(CH_2)_2OH$, —$(CH_2)_{30}H$, —$(CH_2)_{40}H$, —$CH_2OCH_3$, —$CH_2OCH_2CH_3$, —$CH_2O(CH_2)_2CH_3$, —$CH_2OCH(CH_3)_2$, —$CH_2OCH(CH_2CH_3)_2(CH_3)$, —$(CH_2)_2OCH_3$, —$(CH_2)_2OCH_2CH_3$, —$(CH_2)_2O(CH_2)_2CH_3$, —$(CH_2)_{20}CH(CH_3)_2$, or —$(CH_2)_{20}CH(CH_2CH_3)_2(CH_3)$.

Aspect 15. The compound of Aspect 13, wherein $R^{5c}$ is —$OCH_3$, —$OCH_2CH_3$, —$O(CH_2)_2CH_3$, —$OCH(CH_3)_2$, —$CH_2OH$, —$(CH_2)_2OH$, —$(CH_2)_{30}H$, —$CH_2OCH_3$, —$CH_2OCH_2CH_3$, —$CH_2O(CH_2)_2CH_3$, —$CH_2OCH(CH_3)_2$, —$CH_2OCH(CH_2CH_3)_2(CH_3)$, —$(CH_2)_2OCH_3$, —$(CH_2)_2OCH_2CH_3$, —$(CH_2)_2O(CH_2)_2CH_3$, —$(CH_2)_{20}CH(CH_3)_2$, or —$(CH_2)_{20}CH(CH_2CH_3)_2(CH_3)$.

Aspect 16. The compound of Aspect 13, wherein $R^{5c}$ is —$OCH_3$, —$OCH_2CH_3$, —$O(CH_2)_2CH_3$, —$OCH(CH_3)_2$, —$CH_2OH$, —$(CH_2)_2OH$, —$(CH_2)_{30}H$, —$CH_2OCH_3$, —$CH_2OCH_2CH_3$, —$(CH_2)_2OCH_3$, or —$(CH_2)_2OCH_2CH_3$.

Aspect 17. The compound of Aspect 13, wherein $R^{5c}$ is —$OCH_3$, —$OCH_2CH_3$, —$CH_2OH$, —$(CH_2)_2OH$, —$CH_2OCH_3$, or —$CH_2OCH_2CH_3$.

Aspect 18. The compound of Aspect 13, wherein $R^{5c}$ is —$OCH_3$ or —$OCH_2CH_3$.

Aspect 19. The compound of any one of Aspect 12-Aspect 18, wherein each of $R^{5a}$, $R^{5b}$, $R^{5d}$, and $R^{5e}$ is hydrogen.

Aspect 20. The compound of any one of Aspect 1-Aspect 7, wherein $R^{5a}$ is selected from a group having formula represented by a structure: —$R^{20}$, —$R^{30}$-$A^1$-$R^{40}$, -$A^1$-$R^{40}$, -$A^1$-$R^{30}$-$A^2$-$R^{40}$, or -A-$R^{30}$-$A^2$-$R^{31}$-$A^3$-$R^{41}$; and wherein each of $R^{5b}$, $R^{5c}$, $R^{5d}$, and $R^{5e}$ is independently selected from hydrogen, halogen, —$SF_5$, —CN, —$N_3$, —OH, —$NH_2$, —$CF_3$, and —$CF_2CF_3$.

Aspect 21. The compound of Aspect 20, wherein $R^{5a}$ is $R^{20}$.

Aspect 22. The compound of any one of Aspect 20 or Aspect 21, wherein $R^{20}$ is selected from —C2-C7 alkylamino and —C2-C7 alkoxy.

Aspect 23. The compound of any one of Aspect 20 or Aspect 21, wherein $R^{20}$ is halogen.

Aspect 24. The compound of any one of Aspect 1-Aspect 23, wherein each of $R^{5b}$, $R^{5c}$, $R^{5d}$, and $R^{5e}$ is selected from halogen and hydrogen.

Aspect 25. The compound of Aspect 24, wherein each of $R^{5b}$, $R^{5c}$, $R^{5d}$, and $R^{5e}$ is hydrogen.

Aspect 26. The compound of any one of Aspect 1-Aspect 7, wherein $R^{5b}$ is selected from a group having formula represented by a structure: —$R^{20}$, —$R^{30}$-$A^1$-$R^{40}$, -$A^1$-$R^{40}$, -$A^1$-$R^{30}$-$A^2$-$R^{40}$, or -$A^1$-$R^{30}$-$A^2$-$R^{31}$-$A^3$-$R^{41}$; and wherein each of $R^{5a}$, $R^{5c}$, $R^{5d}$, and $R^{5e}$ is independently selected from hydrogen, halogen, —$SF_5$, —CN, —$N_3$, —OH, —$NH_2$, —$CF_3$, and —$CF_2CF_3$.

Aspect 27. The compound of Aspect 26, wherein $R^{5b}$ is $R^{20}$.

Aspect 28. The compound of Aspect 26 or Aspect 27, wherein $R^{20}$ is selected from —C2-C7 alkylamino and —C2-C7 alkoxy.

Aspect 29. The compound of Aspect 26 or Aspect 27, wherein $R^{20}$ is halogen.

Aspect 30. The compound of any one of Aspect 26-Aspect 29, wherein each of $R^{5a}$, $R^{5c}$, $R^{5d}$, and $R^{5e}$ is selected from halogen and hydrogen.

Aspect 31. The compound of Aspect 30, wherein each of $R^{5a}$, $R^{5c}$, $R^{5d}$, and $R^{5e}$ is hydrogen.

Aspect 32. The compound of any one of Aspect 1-Aspect 7, wherein $R^{5c}$ is selected from a group having formula represented by a structure: —$R^{20}$, —$R^{30}$-$A^1$-$R^{40}$, -$A^1$-$R^{40}$, -$A^1$-$R^{30}$-$A^2$-$R^{40}$, or -$A^1$-$R^{30}$-$A^2$-$R^{31}$-$A^3$-$R^{41}$; and wherein each of $R^{5a}$, $R^{5c}$, $R^{5d}$, and $R^{5e}$ is independently selected from hydrogen, halogen, —$SF_5$, —CN, —$N_3$, —OH, —$NH_2$, —$CF_3$, and —$CF_2CF_3$.

Aspect 33. The compound of Aspect 32, wherein $R^{5c}$ is $R^{20}$.

Aspect 34. The compound of Aspect 32 or Aspect 33, wherein $R^{20}$ is selected from —C2-C7 alkylamino and —C2-C7 alkoxy.

Aspect 35. The compound of Aspect 32 or Aspect 33, wherein $R^{20}$ is halogen.

Aspect 36. The compound of anyone of Aspect 32-Aspect 35, wherein each of $R^{5a}$, $R^{5b}$, $R^{5d}$, and $R^{5e}$ is selected from halogen and hydrogen.

Aspect 37. The compound of Aspect 36, wherein each of $R^{5a}$, $R^{5b}$, $R^{5d}$, and $R^{5e}$ is hydrogen.

The compound of Aspect 1, having a structure represented by a formula:

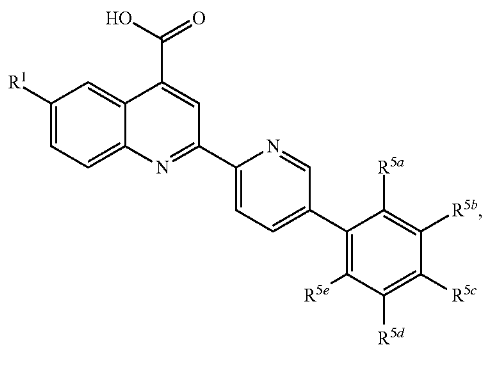

-continued
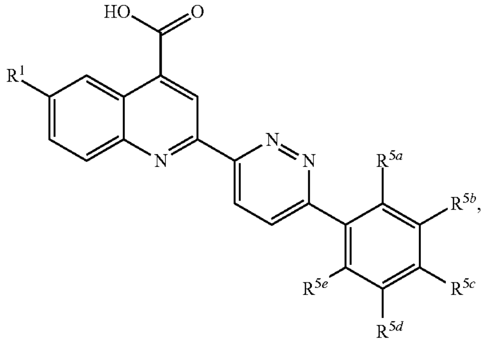
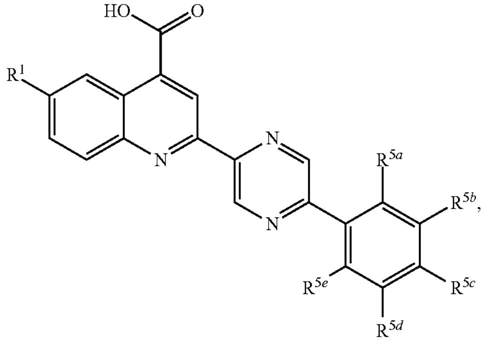
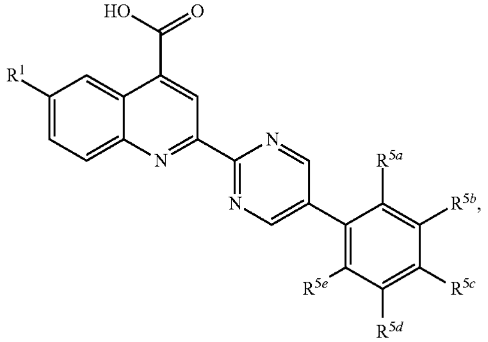
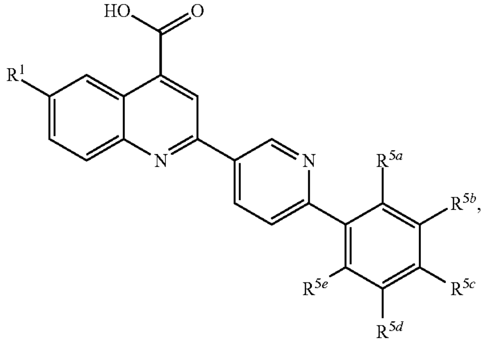
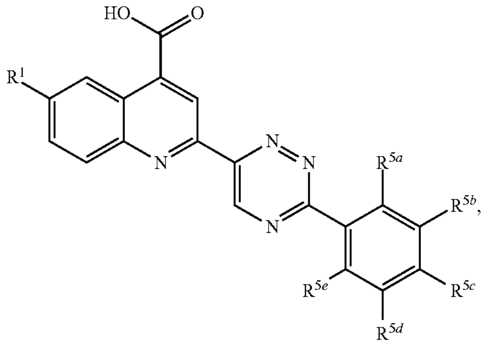
-continued
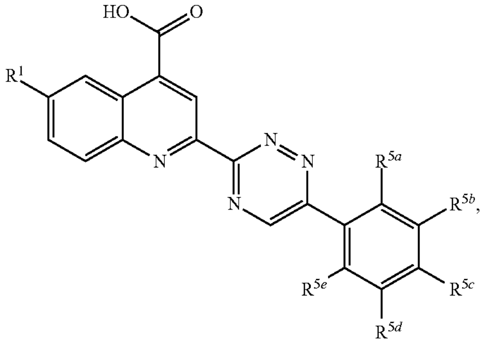
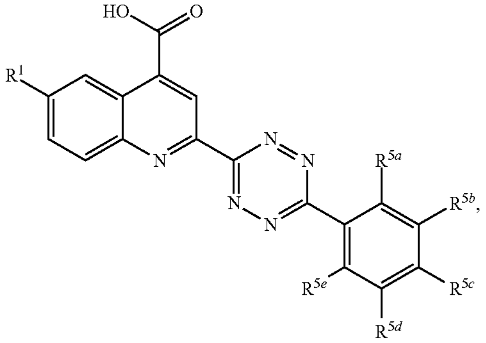
or a subgroup thereof.
Aspect 39. The compound of Aspect 1, having a structure represented by a formula:
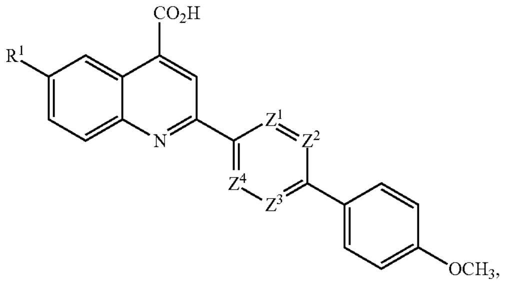
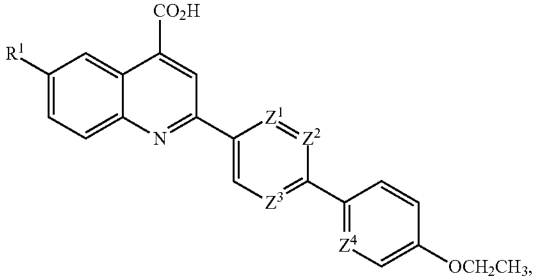
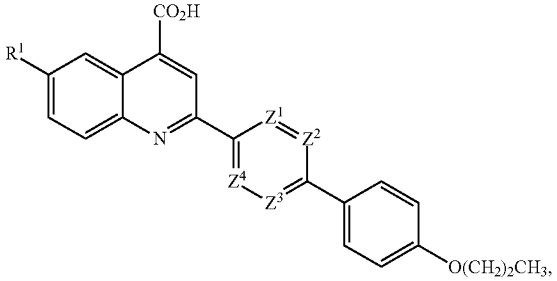

-continued
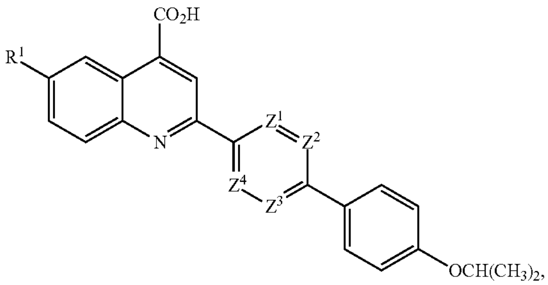
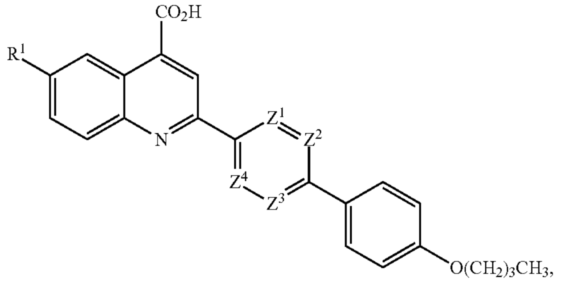
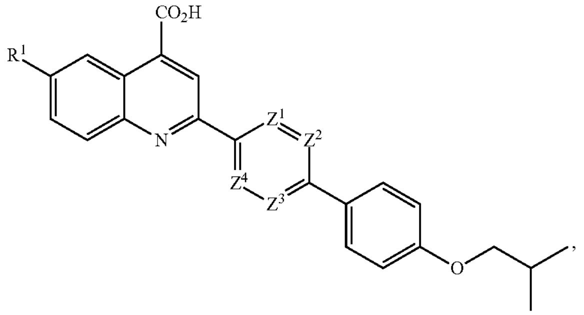
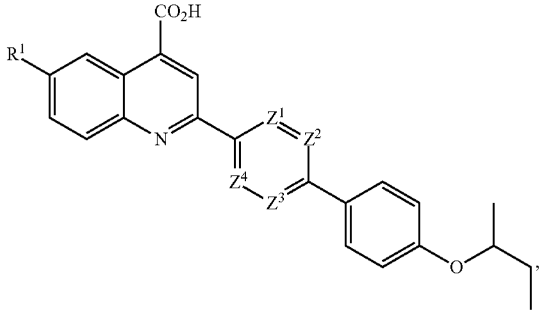
or a subgroup thereof.
Aspect 40. The compound of Aspect 1, present as:
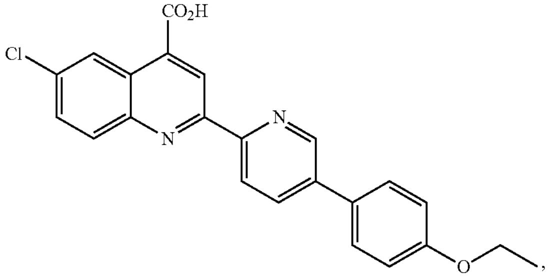
-continued
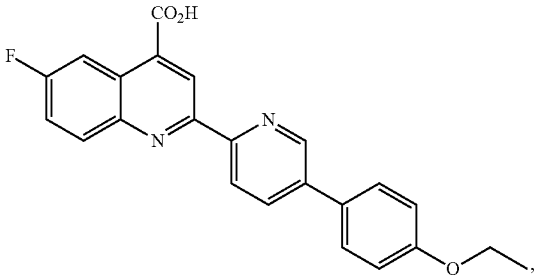
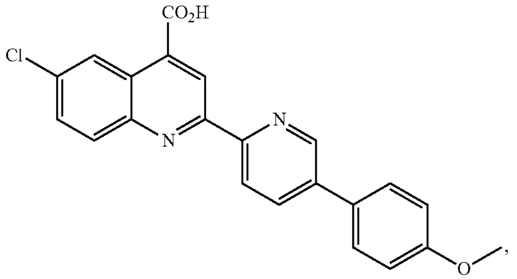
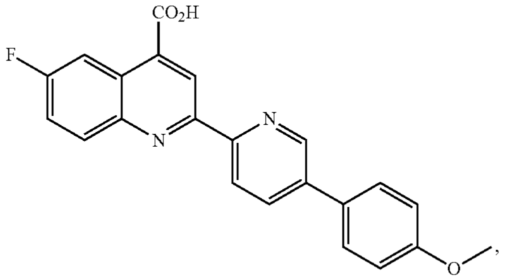
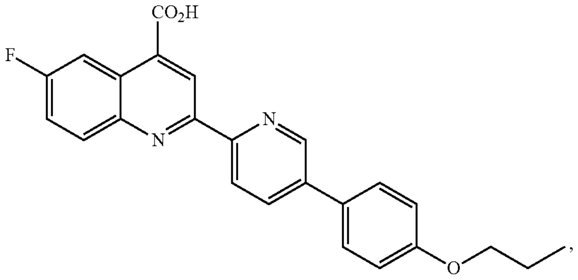
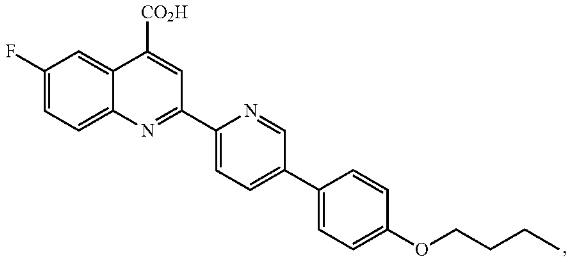
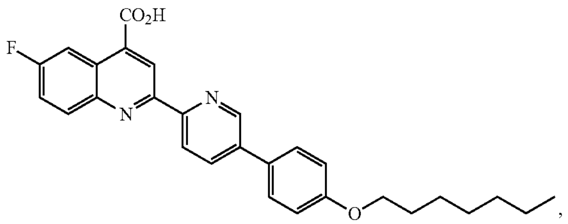

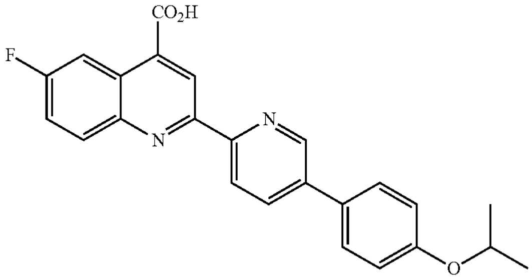
,
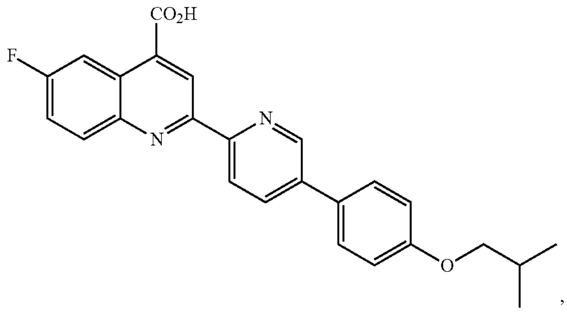
,
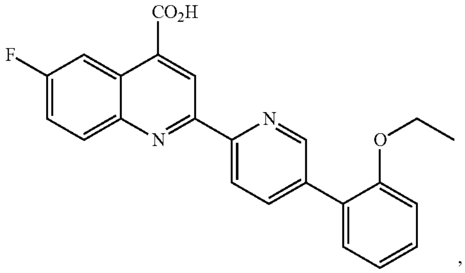
,
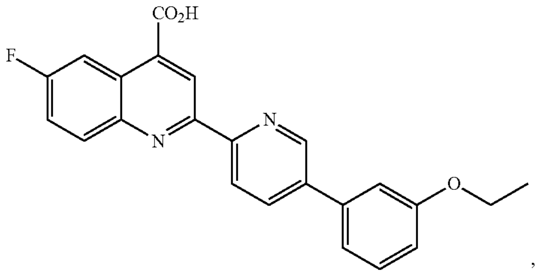
,
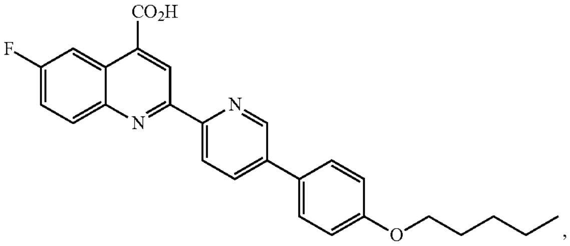
,
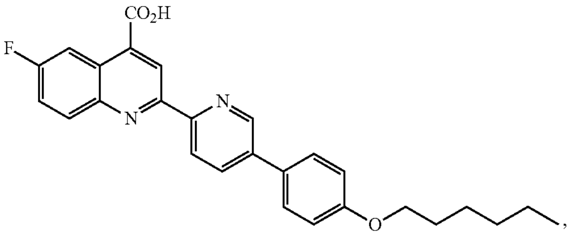
,
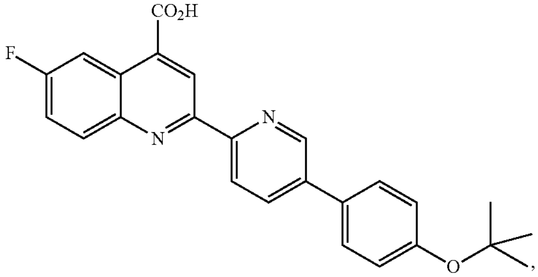
,
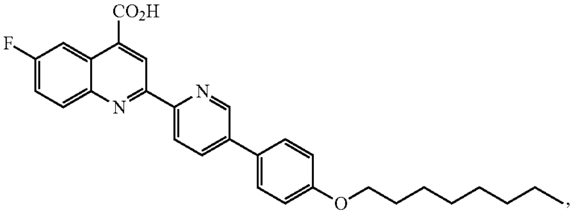
,
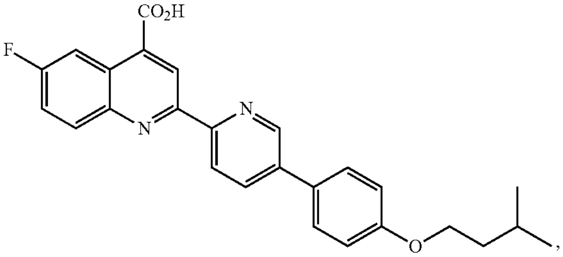
,
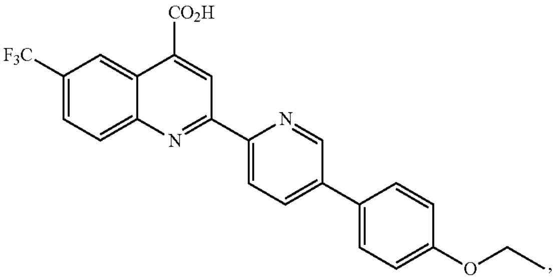
,
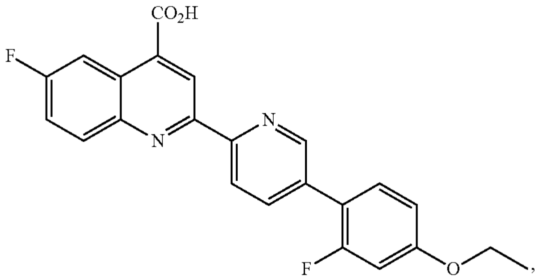
,
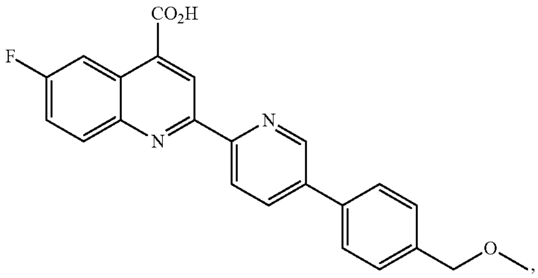
, -continued
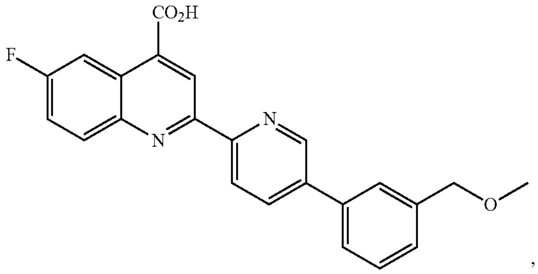
,
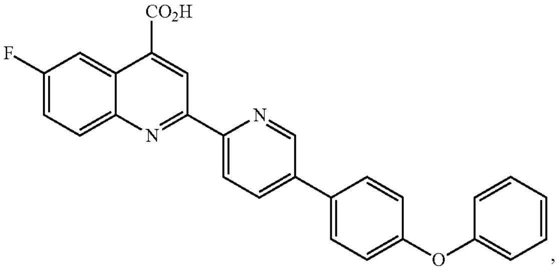
,
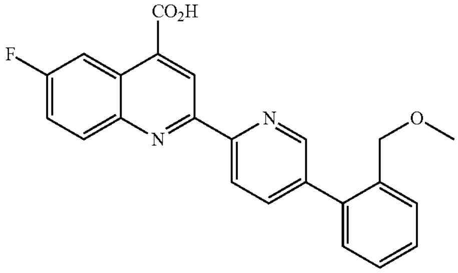
,
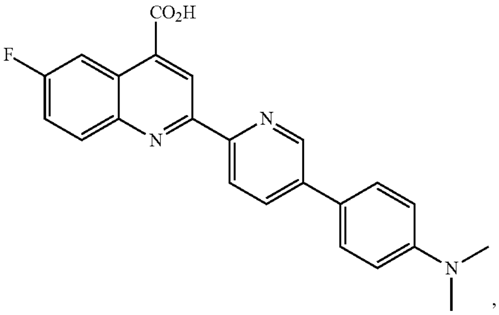
,
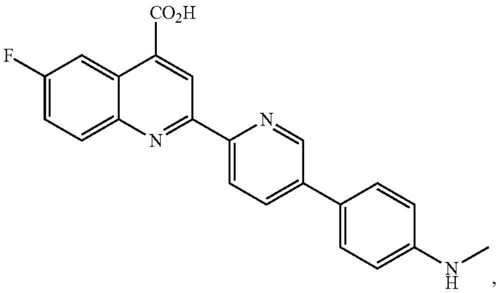
,
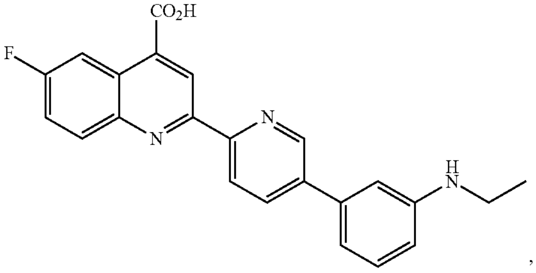
,
-continued
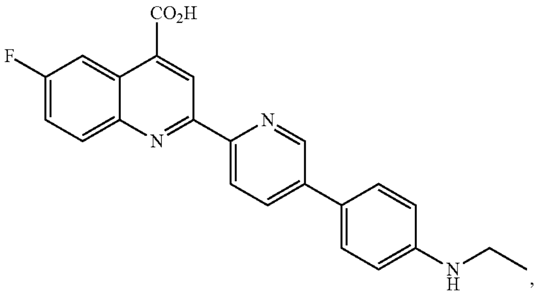
,
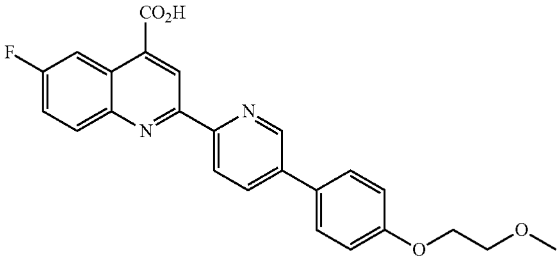
,
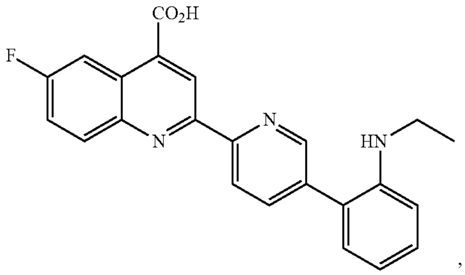
,
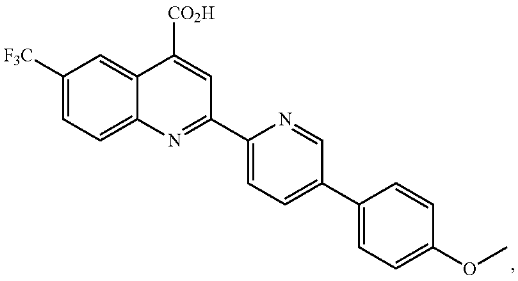
,
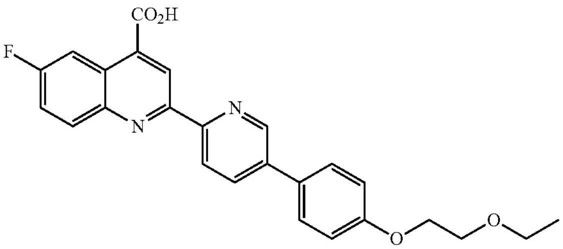
,
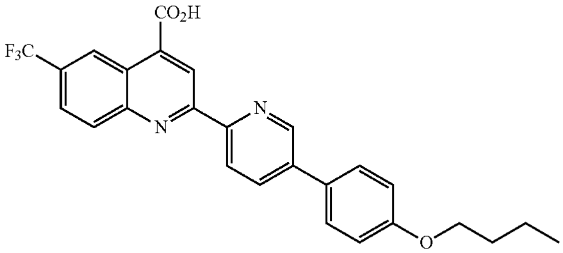
, -continued
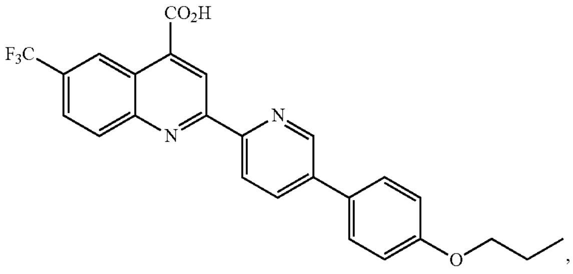
,
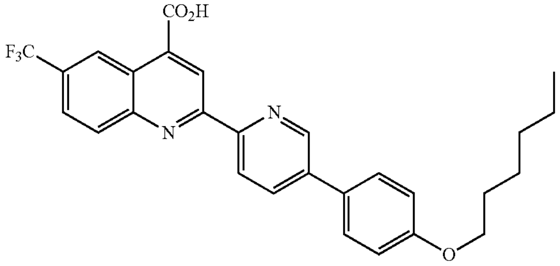
,
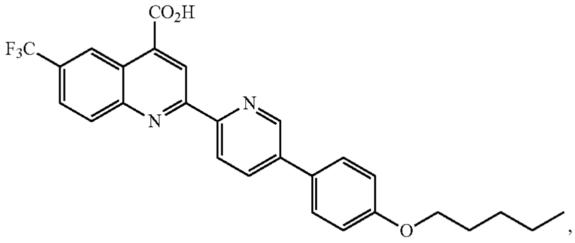
,
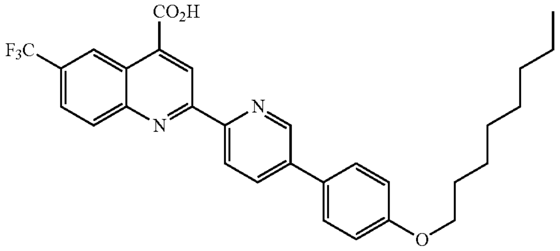
,
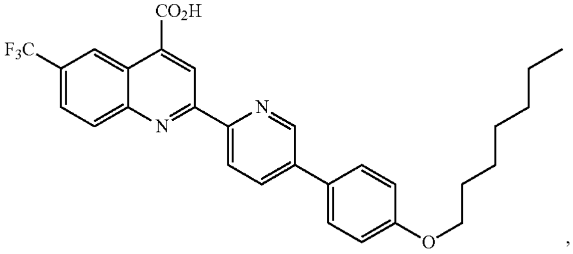
,
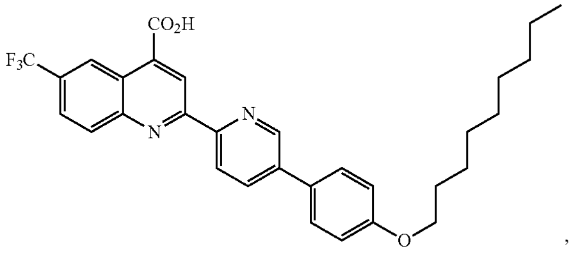
,
-continued
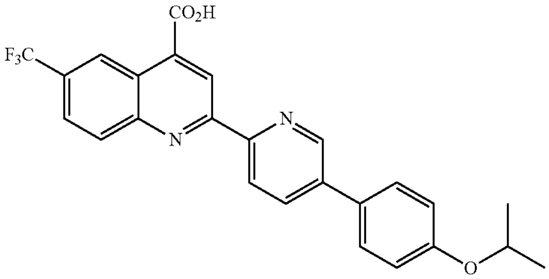
,
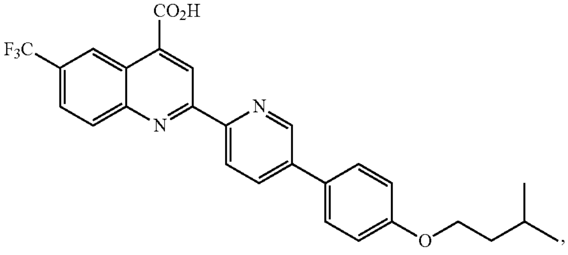
,
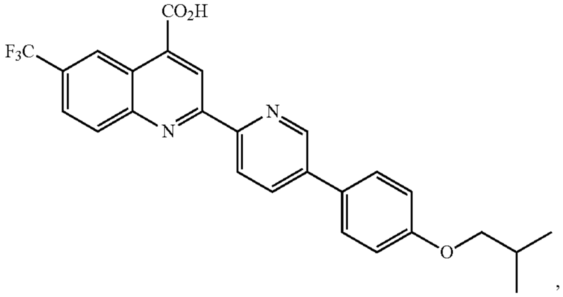
,
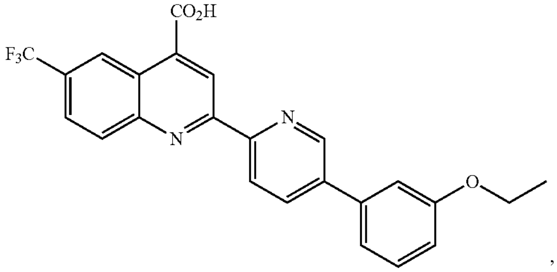
,
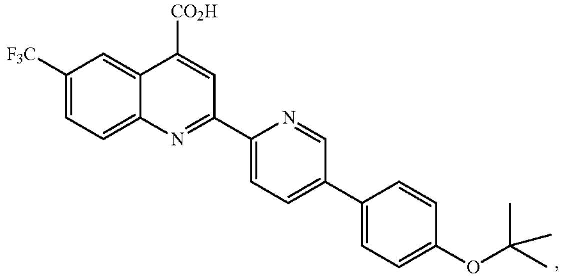
,
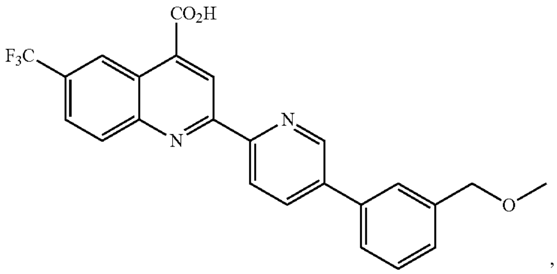
, -continued
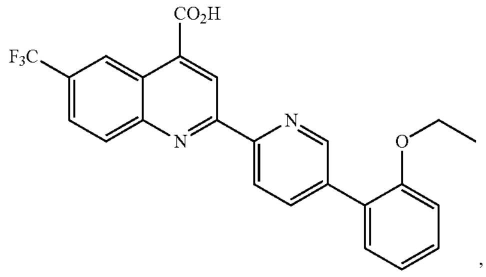
,
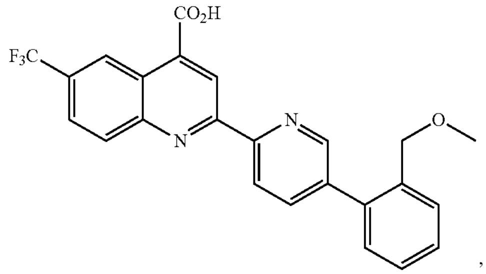
,
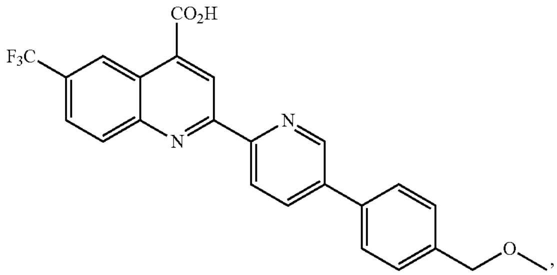
,
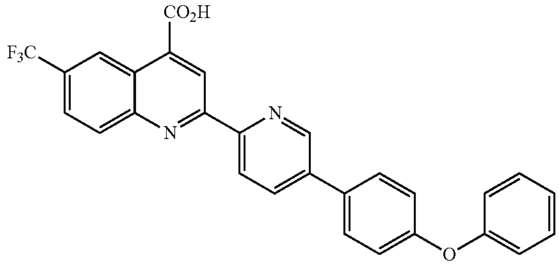
,
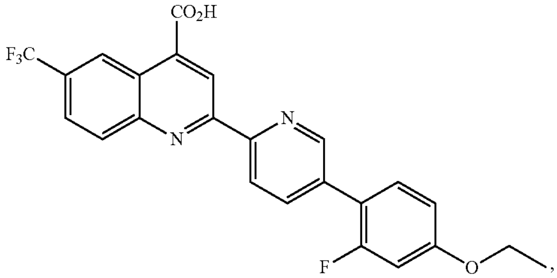
,
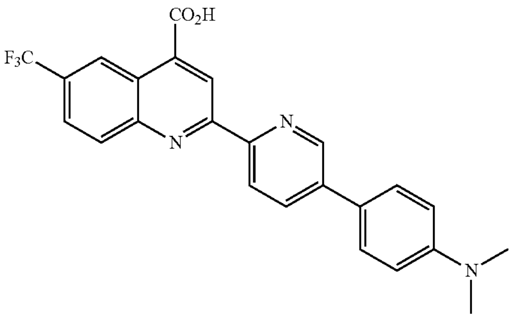
,
-continued
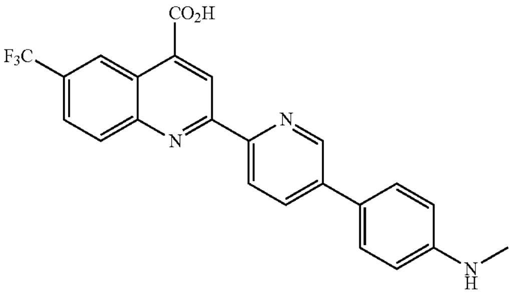
,
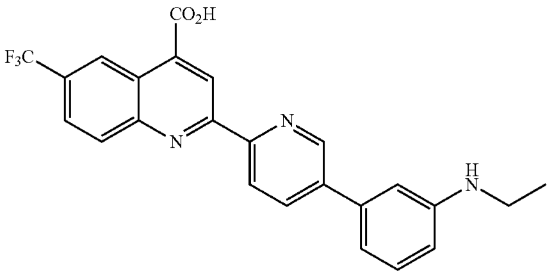
,
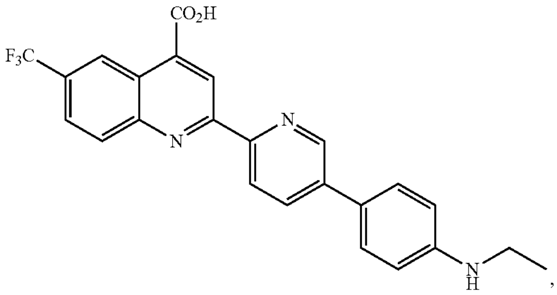
,
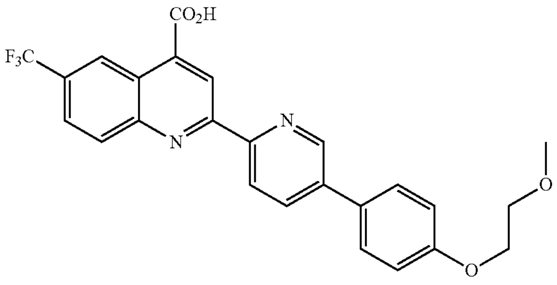
,
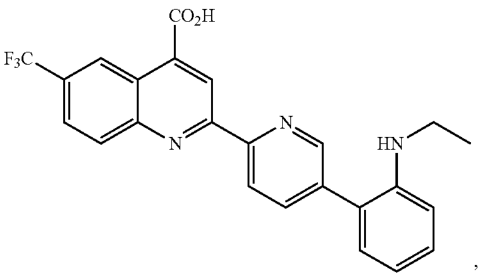
,
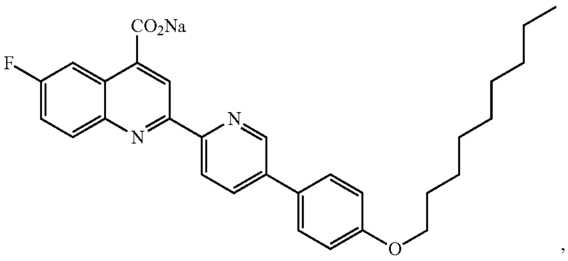
, -continued
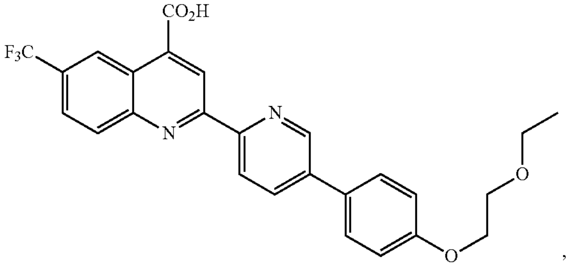
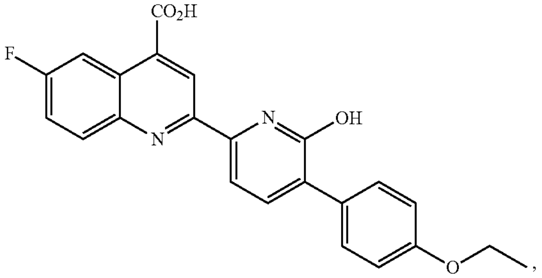
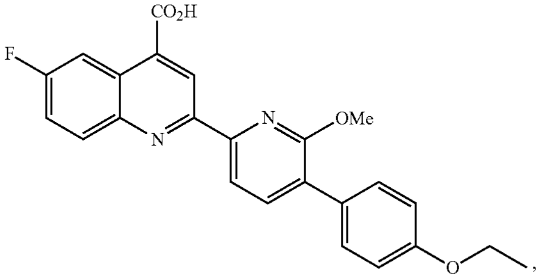
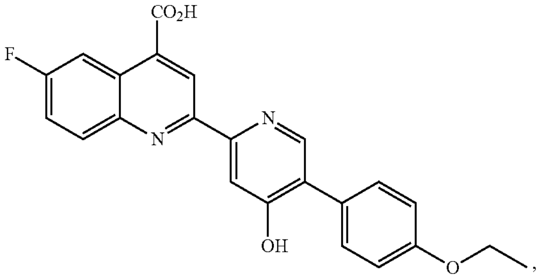
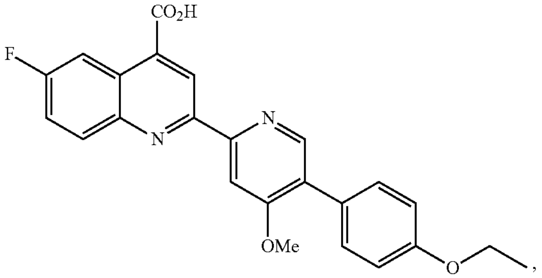
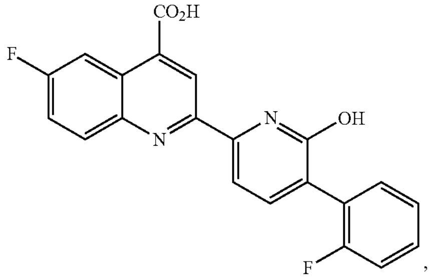
-continued
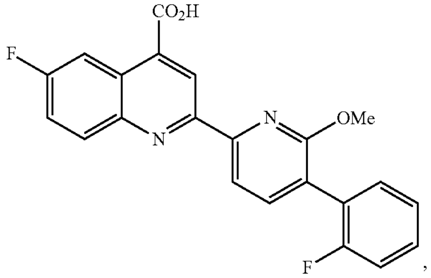
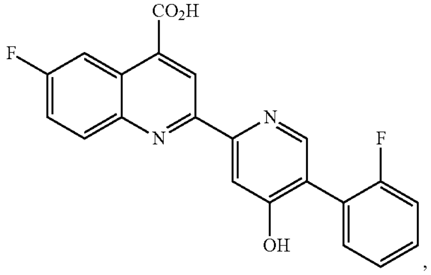
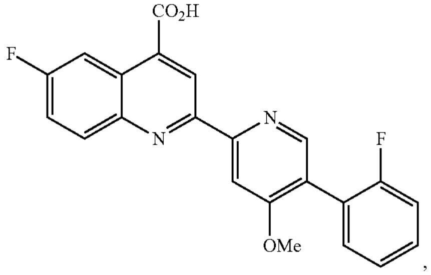
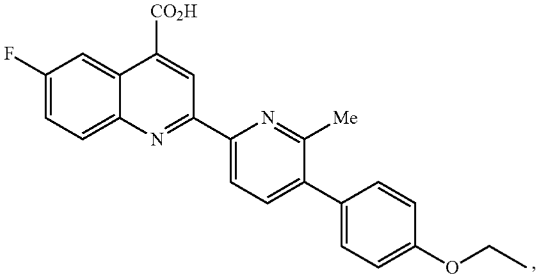
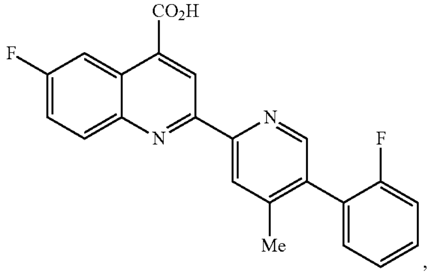
or a subgroup thereof.

Aspect 41. The compound of Aspect 1, present as:

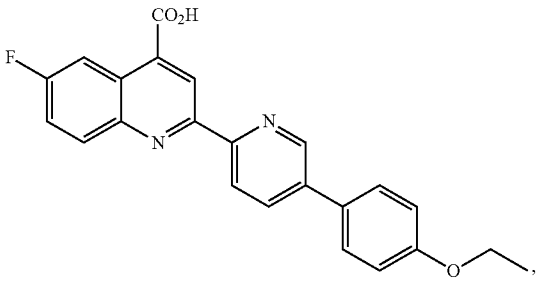
,
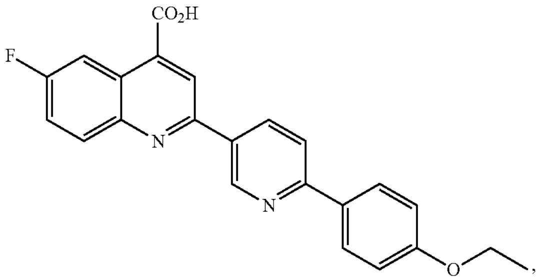
,
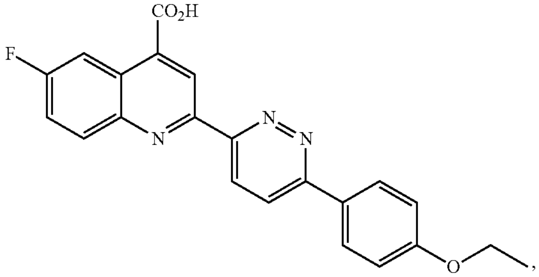
,
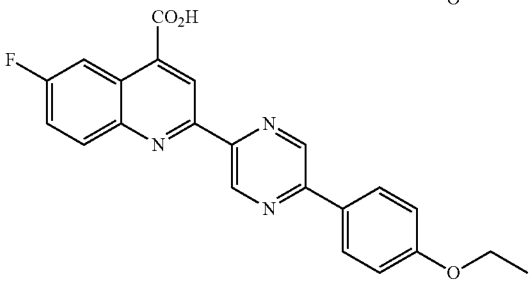
,
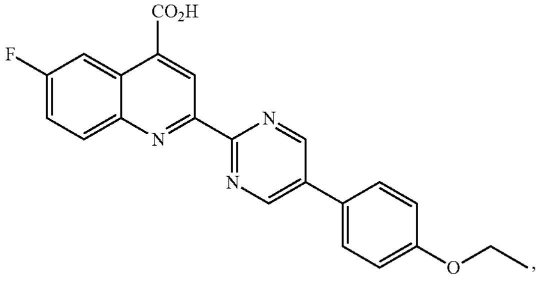
, or a subgroup thereof.

Aspect 42. The compound of any one of Aspect 1-Aspect 41, wherein the compound is a pharmaceutically acceptable salt thereof comprising the conjugate base form of the compound, and a counter ion selected from $Li^{+}$, $K^{+}$, $Na^{+}$, ammonium, tetramethylammonium, tetraethylammonium, $Fe^{+2}$, $Cu^{+2}$, $Zn^{+2}$, $Mg^{+2}$, $Ca^{+2}$, $Al^{+3}$, $Fe^{+3}$, and combinations thereof.

Aspect 43. The compound of Aspect 42, wherein the counter ion is Na+.

Aspect 44. A pharmaceutical composition comprising a therapeutically effective amount of a compound of any of Aspect 1-Aspect 43, or a pharmaceutically acceptable salt thereof, and a pharmaceutically acceptable carrier.

Aspect 45. The pharmaceutical composition of Aspect 44, further comprising at least one agent known to treat a cancer.

Aspect 46. The pharmaceutical composition of Aspect 45, wherein the at least one agent is a DNA methyltransferase inhibitor, an HDAC-inhibitor, a glucocorticoid, an mTOR inhibitor, a cytotoxic agent, or combinations thereof.

Aspect 47. The pharmaceutical composition of Aspect 46, wherein the DNA methyltransferase inhibitor is 5-aza-2'-deoxycytidine, 5-azacytidine, zebularin, epigallocatechin-3-gallate, procaine, or combinations thereof.

Aspect 48. The pharmaceutical composition of Aspect 46, wherein the HDAC-inhibitor is vorinostat, entinostat, panbinostat, trichostatin A, mocetinostat, belinostat, dacinostat, givinostat, tubastatin A, pracinostat, droxinostat, quisinostat, romidepsin, valproic acid, AR-42 (OSU-HDAC42), tacedinaline, rocilinostat, apicidin, or combinations thereof.

Aspect 49. The pharmaceutical composition of Aspect 46, wherein the glucocorticoid is dexamethasone, prednisolone, methylprednisolone, betamethasone, triamicinolone, fludrocortisone, beclomethasone, or combinations thereof.

Aspect 50. The pharmaceutical composition of Aspect 46, wherein the mTor inhibitor is BEZ235, everolimus, temsirolimus, rapamycin, AZD8055, or combinations thereof.

Aspect 51. The pharmaceutical composition of Aspect 46, wherein the cytotoxic agent is an alkylating agent, an antimetabolite agent, an antineoplastic antibiotic agent, a mitotic inhibitor agent, a mTor inhibitor agent or other chemotherapeutic agent.

Aspect 52. The pharmaceutical composition of Aspect 51, wherein the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

Aspect 53. The pharmaceutical composition of Aspect 51, wherein the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

Aspect 54. The pharmaceutical composition of Aspect 51, wherein the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

Aspect 55. The pharmaceutical composition of Aspect 51, wherein the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

Aspect 56. The pharmaceutical composition of Aspect 51, wherein the mTor inhibitor is everolimus, sirolimus, temsirolimus, or combinations thereof.

Aspect 57. The pharmaceutical composition of Aspect 51, wherein the other chemotherapeutic agent is an anthracycline, cytarabine, a purine analog, sorafenib, gemtuzumab ozogamicin, rituximab, or combinations thereof.

Aspect 58. The pharmaceutical composition of Aspect 57, wherein the anthracycline is daunorubicin, idarubicin, or combinations thereof.

Aspect 59. The pharmaceutical composition of Aspect 57, wherein the purine analog is cladribine, fludarabine, clofarabine, or combinations thereof.

Aspect 60. The pharmaceutical composition of Aspect 44, further comprising at least one agent known to treat GVHD.

Aspect 61. The pharmaceutical composition of Aspect 60, wherein the least one agent known to treat GVHD is a steroid, an mTor inhibitor, a tyrosine kinase inhibitor, or other agent known to treat GVHD.

Aspect 62. The pharmaceutical composition of Aspect 61, wherein the steroid is dexamethasone, prednisolone, methylprednisolone, betamethasone, triamicinolone, fludrocortisone, beclomethasone, or combinations thereof.

Aspect 63. The pharmaceutical composition of Aspect 61, wherein tyrosine kinase inhibitor is imatinib, ruxolitinib, or a combination thereof.

Aspect 64. The pharmaceutical composition of Aspect 61, wherein the mTor inhibitor is everolimus, sirolimus, temsirolimus, or combinations thereof.

Aspect 65. The pharmaceutical composition of Aspect 61, wherein the other agent known to treat GVHD is tacrolimus, clofazimine, psoralen, cyclosporine, alemtuzumab, infliximab, rituximab, etanercept, antithymocyte globulin, thalidomide, mycophenolate mofetil, pentostatin, methotrexate, halofuginone, hydroxychloroquine, or combinations thereof.

Aspect 66. The pharmaceutical composition of Aspect 44, further comprising the step of administering a therapeutically effective amount of at least one agent known to treat an autoimmune disorder or disease.

Aspect 67. The pharmaceutical composition of Aspect 66, wherein the at least one agent known to treat an autoimmune disorder or disease is selected from the group consisting of: (a) disease modifying antirheumatic drugs; (b) nonsteroidal antiinflammatory drugs; (c) COX-2 selective inhibitors; (d) COX-1 inhibitors; (e) immunosuppressive drugs, including p70S6 kinase inhibitors; and inosine monophosphate dehydrogenase inhibitors; (f) steroids; (g) biological response modifiers; and (h) other agents useful for the treatment of autoimmune disorders.

Aspect 68. The pharmaceutical composition of Aspect 67, wherein the disease modifying antirheumatic drug is selected from methotrexate, gold salts, D-penicillamine, hydroxychloroquine, auranofin, sulfasalazine, and combinations thereof.

Aspect 69. The pharmaceutical composition of Aspect 67, wherein the nonsteroidal antiinflammatory drug is selected from indomethacin, naproxen, diclofenac, ibuprofen, aspirin and aspirin analogs, acetaminophen, and combinations thereof.

Aspect 70. The pharmaceutical composition of Aspect 67, wherein the COX-2 selective inhibitor is selected from celecoxib, rofecoxib, etoricoxib, valdecoxib, lumiracoxib, and combinations thereof.

Aspect 71. The pharmaceutical composition of Aspect 67, wherein the immunosuppressive drug is selected from a calcineurin inhibitor such as cyclosporin and FK506; a p70S6 kinase inhibitor such as sirolimus and rapamycin; an inosine monophosphate dehydrogenase inhibitor such as mycophenolate; leflunomide, cyclophosphamide, azathioprine, and combinations thereof.

Aspect 72. The pharmaceutical composition of Aspect 67, wherein the steroid is selected from prednisone, betamethasone, budesonide and dexamethasone, and combinations thereof.

Aspect 73. The pharmaceutical composition of Aspect 67, wherein the biological response modifier is selected from TNFα antagonists such as infliximab, adalimmab and etanercept; IL-1 receptor antagonists such as anakinra; humanized or chimeric antibodies or fusion proteins such as alefacept, efalizumab, daclizumab; anti-chemokine antibodies; anti-interleukin antibodies; and combinations thereof.

Aspect 74. The pharmaceutical composition of Aspect 67, wherein the other agent useful for the treatment of autoimmune disorder is selected from hemokine receptor antagonists or modulators, cannabinoid receptor antagonists or modulators, inhibitors of matrix metalloproteinases, TNFα-converting enzymes, nitric oxide synthetases or phosphodiesterase IV, such as roflumilast or cilomilast; inhibitors of p38 MAP-kinase, the NF-kappas, pathway or IL-1 receptor associated kinase or inhibitors of interactions involving adhesion molecules such as LFA-1, VLA-4, ICAM-1, VCAM-1, α4β7, MAdCAM-1, and αvβ3; and combinations thereof.

Aspect 75. A method for the treatment of a disease or disorder in a mammal comprising the step of administering to the mammal a therapeutically effective amount of at least one compound of any of Aspect 1-Aspect 43, or a pharmaceutically acceptable salt thereof, or the pharmaceutical composition of any of Aspect 44-Aspect 74.

Aspect 76. The method of Aspect 75, wherein the mammal is a human.

Aspect 77. The method of Aspect 75, wherein the mammal has been diagnosed with a need for treatment of the disorder prior to the administering step.

Aspect 78. The method of Aspect 77, wherein the disorder or disease is associated with abnormal, increased, or aberrant dihydroorotate dehydrogenase (DHODH) activity.

Aspect 79. The method of Aspect 78, wherein the disorder or disease can be treated by inhibition of dihydroorotate dehydrogenase (DHODH) activity.

Aspect 80. The method of any one of Aspect 75-Aspect 79, further comprising the step of identifying a mammal in need of treatment of the disorder or disease.

Aspect 81. The method of Aspect 80, wherein the disorder or disease is associated with abnormal, increased, or aberrant dihydroorotate dehydrogenase (DHODH) activity.

Aspect 82. The method of Aspect 81, wherein the disorder or disease can be treated by inhibition of dihydroorotate dehydrogenase (DHODH) activity.

Aspect 83. The method of any one of Aspect 75-Aspect 82, wherein the disorder is a cancer.

Aspect 84. The method of Aspect 83, wherein the cancer is selected from breast cancer, renal cancer, gastric cancer, colorectal cancer, ovarian cancer, prostate cancer, pancreatic cancer, brain cancer, genitourinary tract cancer, lymphatic system cancer, stomach cancer, larynx cancer, lung cancer, pancreatic cancer, breast cancer, and malignant melanoma.

Aspect 85. The method of Aspect 83, wherein the cancer is a hematological cancer.

Aspect 86. The method of Aspect 85, wherein the hematological cancer is leukemia, lymphoma, myeloma, myelodysplastic syndrome, or myeloproliferative neoplasm.

Aspect 87. The method of Aspect 86, wherein the hematological cancer is chronic myeloid leukemia (CML), acute myeloid leukemia (AML), chronic lymphoid leukemia (CLL), acute lymphoid leukemia (ALL), hairy cell leukemia, chronic myelomonocytic leukemia (CMML), juvenile myelomonocyte leukemia (JMML), large granular lymphocytic leukemia (LGL), acute lymphocytic leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, Hodgkin lymphoma, and non-Hodgkin lymphoma.

Aspect 88. The method of Aspect 87, wherein the hematological cancer is chronic myeloid leukemia (CML) or acute myeloid leukemia (AML).

Aspect 89. The method of any one of Aspect 75-Aspect 88, further comprising the step of administering a therapeutically effective amount of at least one agent known to treat a cancer.

Aspect 90. The method of Aspect 89, wherein the at least one agent is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, and vasostatin.

Aspect 91. The method of Aspect 89, wherein the at least one agent is a DNA methyltransferase inhibitor, an HDAC-inhibitor, a glucocorticoid, an mTOR inhibitor, a cytotoxic agent, or combinations thereof.

Aspect 92. The method of Aspect 91, wherein the DNA methyltransferase inhibitor is 5-aza-2'-deoxycytidine, 5-azacytidine, zebularin, epigallocatechin-3-gallate, procaine, or combinations thereof.

Aspect 93. The method of Aspect 91, wherein the HDAC-inhibitor is vorinostat, entinostat, panbinostat, trichostatin A, mocetinostat, belinostat, dacinostat, givinostat, tubastatin A, pracinostat, droxinostat, quisinostat, romidepsin, valproic acid, AR-42 (OSU-HDAC42), tacedinaline, rocilinostat, apicidin, or combinations thereof.

Aspect 94. The method of Aspect 91, wherein the glucocorticoid is dexamethasone, prednisolone, methylprednisolone, betamethasone, triamicinolone, fludrocortisone, beclomethasone, or combinations thereof.

Aspect 95. The method of Aspect 91, wherein the mTor inhibitor is BEZ235, everolimus, temsirolimus, rapamycin, AZD8055, or combinations thereof.

Aspect 96. The method of Aspect 91, wherein the cytotoxic agent is an alkylating agent, an antimetabolite agent, an antineoplastic antibiotic agent, a mitotic inhibitor agent, a mTor inhibitor agent or other chemotherapeutic agent.

Aspect 97. The method of 95, wherein the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

Aspect 98. The method of 95, wherein the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

Aspect 99. The method of 95, wherein the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

Aspect 100. The method of 95, wherein the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

Aspect 101. The method of 95, wherein the mTor inhibitor is everolimus, sirolimus, temsirolimus, or combinations thereof.

Aspect 102. The method of 95, wherein the other chemotherapeutic agent is an anthracycline, cytarabine, a purine analog, sorafenib, gemtuzumab ozogamicin, rituximab, or combinations thereof.

Aspect 103. The method of Aspect 102, wherein the anthracycline is daunorubicin, idarubicin, or combinations thereof.

Aspect 104. The method of Aspect 102, wherein the purine analog is cladribine, fludarabine, clofarabine, or combinations thereof.

Aspect 105. The method of any one of Aspect 89-Aspect 104, wherein the at least one compound and the at least one agent are administered sequentially.

Aspect 106. The method of any one of Aspect 89-Aspect 104, wherein the at least one compound and the at least one agent are administered simultaneously.

Aspect 107. The method of any one of Aspect 89-Aspect 104, wherein the at least one compound and the at least one agent are co-formulated.

Aspect 108. The method of any one of Aspect 89-Aspect 104, wherein the at least one compound and the at least one agent are co-packaged.

Aspect 109. The method of any one of Aspect 75-Aspect 80, wherein the disorder is mediated by T-cell proliferation.

Aspect 110. The method of Aspect 109, wherein the disorder is psoriasis.

Aspect 111. The method of Aspect 109, wherein the disorder is graft-versus-host disease (GVHD).

Aspect 112. The method of Aspect 111, wherein the GVHD is associated with an organ transplant, an allograft, a xenograft, or a hematopoietic stem cell transplantation.

Aspect 113. The method of Aspect 111 or Aspect 112, wherein the GVHD is acute GVHD.

Aspect 114. The method of Aspect 111 or Aspect 112, wherein the GVHD is chronic GVHD.

Aspect 115. The method of any one of Aspect 111-Aspect 114, further comprising the step of administering a therapeutically effective amount of at least one agent known to treat GVHD.

Aspect 116. The method of Aspect 115, wherein the least one agent known to treat GVHD is a steroid, an mTor inhibitor, a tyrosine kinase inhibitor, or other agent known to treat GVHD.

Aspect 117. The method of Aspect 116, wherein the steroid is dexamethasone, prednisolone, methylprednisolone, betamethasone, triamicinolone, fludrocortisone, beclomethasone, or combinations thereof.

Aspect 118. The method of Aspect 116, wherein tyrosine kinase inhibitor is imatinib, ruxolitinib, or a combination thereof.

Aspect 119. The method of Aspect 116, wherein the mTor inhibitor is everolimus, sirolimus, temsirolimus, or combinations thereof.

Aspect 120. The method of Aspect 116, wherein the other agent known to treat GVHD is tacrolimus, clofazimine, psoralen, cyclosporine, alemtuzumab, infliximab, rituximab, etanercept, antithymocyte globulin, thalidomide, mycophenolate mofetil, pentostatin, methotrexate, halofuginone, hydroxychloroquine, or combinations thereof.

Aspect 121. The method of any one of Aspect 75-Aspect 80, wherein the disorder is associated with T-cell proliferation.

Aspect 122. The method of any one of Aspect 75-Aspect 80, wherein the disorder is an autoimmune disorder or disease.

Aspect 123. The method of Aspect 122, wherein the autoimmune disorder or disease is selected from lupus, rheumatoid arthritis, ankylosing spondylitis, glomerulonephritis, minimal change disease, ulcerative colitis, crohns disease, addison's disease, adult Still's disease, alopecia areata, autoimmune hepatitis, autoimmune angioedema, Bechet's disease, pemphigoid and variants, celiac disease, chronic inflammatory demyelinating polyneuropathy, churg-Straus syndrome, Crest syndrome, dermatomyositis, neuromyelitis optica, discoid lupus, fibromyalgia, giant cell arteritis, giant cell myocarditis, Goodpasteur's disease, evan's syndrome, autoimmune hemolytic anemia, immune thrombocytopenia, Henoch-Schonlein purpura, IgA nephropathy, IgG4 related sclerosing disease, juvenile arthritis, juvenile diabetes, Kawasaki disease, Leukocytoclastic vasculitis, mixed connective disease, multiple sclerosis, multifocal motor neuropathy, myasthenia gravis, autoimmune neutropenia, optic neuritis, peripheral neuropathy, POEMS syndrome, polymyositis, primary biliary cirrhosis, non-alcoholic hepatosteotosis and associated cirrhosis, psoriasis, scleroderma, sarcoidosis, temporal arteritis, vasculitis, and uveitis.

Aspect 124. The method of Aspect 122 or Aspect 123, further comprising the step of administering a therapeutically effective amount of at least one agent known to treat an autoimmune disorder or disease.

Aspect 125. The method of Aspect 124, wherein the at least one agent known to treat an autoimmune disorder or disease is selected from the group consisting of: (a) disease modifying antirheumatic drugs; (b) nonsteroidal antiinflammatory drugs; (c) COX-2 selective inhibitors; (d) COX-1 inhibitors; (e) immunosuppressive drugs, including p70S6 kinase inhibitors; and inosine monophosphate dehydrogenase inhibitors; (f) steroids; (g) biological response modifiers; and (h) other agents useful for the treatment of autoimmune disorders.

Aspect 126. The method of Aspect 125, wherein the disease modifying antirheumatic drug is selected from methotrexate, gold salts, D-penicillamine, hydroxychloroquine, auranofin, sulfasalazine, and combinations thereof.

Aspect 127. The method of Aspect 125, wherein the nonsteroidal antiinflammatory drug is selected from indomethacin, naproxen, diclofenac, ibuprofen, aspirin and aspirin analogs, acetaminophen, and combinations thereof.

Aspect 128. The method of Aspect 125, wherein the COX-2 selective inhibitor is selected from celecoxib, rofecoxib, etoricoxib, valdecoxib, lumiracoxib, and combinations thereof.

Aspect 129. The method of Aspect 125, wherein the immunosuppressive drug is selected from a calcineurin inhibitor such as cyclosporin and FK506; a p70S6 kinase inhibitor such as sirolimus and rapamycin; an inosine monophosphate dehydrogenase inhibitor such as mycophenolate; leflunomide, cyclophosphamide, azathioprine, and combinations thereof.

Aspect 130. The method of Aspect 125, wherein the steroid is selected from prednisone, betamethasone, budesonide and dexamethasone, and combinations thereof.

Aspect 131. The method of Aspect 125, wherein the biological response modifier is selected from TNFα antagonists such as infliximab, adalimmab and etanercept; IL-1 receptor antagonists such as anakinra; humanized or chimeric antibodies or fusion proteins such as alefacept, efalizumab, daclizumab; anti-chemokine antibodies; anti-interleukin antibodies; and combinations thereof.

Aspect 132. The method of Aspect 125, wherein the other agent useful for the treatment of autoimmune disorder is selected from hemokine receptor antagonists or modulators, cannabinoid receptor antagonists or modulators, inhibitors of matrix metalloproteinases, TNFα-converting enzymes, nitric oxide synthetases or phosphodiesterase IV, such as roflumilast or cilomilast; inhibitors of p38 MAP-kinase, the NF-kappaβ, pathway or IL-1 receptor associated kinase or inhibitors of interactions involving adhesion molecules such as LFA-1, VLA-4, ICAM-1, VCAM-1, α4β7, MAdCAM-1, and αvβ3; and combinations thereof.

Aspect 133. A method for inhibiting dihydroorotate dehydrogenase activity in at least one cell, comprising the step of contacting the at least one cell with an effective amount of at least one compound of any of Aspect 1-Aspect 43, or a pharmaceutically acceptable salt thereof, or the pharmaceutical composition of any of Aspect 44-Aspect 74.

Aspect 134. The method of Aspect 133, wherein the cell is mammalian.

Aspect 135. The method of Aspect 134, wherein the cell is human.

Aspect 136. The method of any one of Aspect 133-Aspect 135, wherein the cell has been isolated from a mammal prior to the contacting step.

Aspect 137. The method of any one of Aspect 133-Aspect 135, wherein contacting is via administration to a mammal.

Aspect 138. The method of Aspect 137, wherein the mammal has been diagnosed with a need for inhibiting dihydroorotate dehydrogenase activity prior to the administering step.

Aspect 139. The method of Aspect 138, wherein the mammal has been diagnosed with a need for treatment of a disorder related to dihydroorotate dehydrogenase activity prior to the administering step.

Aspect 140. The method of any one of Aspect 133-Aspect 139, wherein the compound exhibits inhibition of dihydroorotate dehydrogenase with an $IC_{50}$ of less than about 1,000 nM using a cell-free enzymatic assay.

Aspect 141. The method of Aspect 140, exhibits inhibition of dihydroorotate dehydrogenase with an $IC_{50}$ of less than about 500 nM.

Aspect 142. The method of Aspect 140, exhibits inhibition of dihydroorotate dehydrogenase with an $IC_{50}$ of less than about 250 nM.

Aspect 143. The method of Aspect 140, exhibits inhibition of dihydroorotate dehydrogenase with an $IC_{50}$ of less than about 100 nM.

Aspect 144. The method of Aspect 140, exhibits inhibition of dihydroorotate dehydrogenase with an $IC_{50}$ of less than about 50 nM.

Aspect 145. A kit comprising a therapeutically effective amount of at least one compound of any of Aspect 1-Aspect 43, or a pharmaceutically acceptable salt thereof, or the pharmaceutical composition of any of Aspect 44-Aspect 74; and: (a) at least one agent known to treat a cancer, a host-versus-graft-disease, and/or a disorder associated with T-cell proliferation; and (b) instructions for treating a cancer, a host-versus-graft-disease, and/or a disorder associated with T-cell proliferation.

Aspect 146. The kit of Aspect 145, wherein the at least one compound or the pharmaceutical composition and the at least one agent are co-formulated.

Aspect 147. The kit of Aspect 145, wherein the at least one compound or the pharmaceutical composition and the at least one agent are co-packaged.

Aspect 148. The kit of Aspect 145, further comprising instructions to provide the compound in connection with surgery.

Aspect 149. The kit of Aspect 148, wherein the instructions provide that surgery is performed prior to the administering of at least one compound.

Aspect 150. The kit of Aspect 148, wherein the instructions provide that surgery is performed after the administering of at least one compound.

Aspect 151. The kit of Aspect 148, wherein the instructions provide that the administering of at least one compound is to effect presurgical debulking of a tumor.

Aspect 152. The kit of Aspect 148, wherein the instructions provide that surgery is performed at about the same time as the administering of at least one compound.

Aspect 153. The kit of Aspect 145, further comprising instructions to provide the at least one compound or the pharmaceutical composition in connection with radiotherapy.

Aspect 154. The kit of Aspect 153, wherein the instructions provide that radiotherapy is performed prior to the administering of at least one compound.

Aspect 155. The kit of Aspect 153, wherein the instructions provide that radiotherapy is performed after the step of the administering of at least one compound.

Aspect 156. The kit of Aspect 153, wherein the instructions provide that radiotherapy is performed at about the same time as the step of the administering of at least one compound.

Aspect 157. The kit of Aspect 145, further comprising a plurality of dosage forms, the plurality comprising one or more doses; wherein each dose comprises a therapeutically effective amount of the at least one compound or the pharmaceutical composition and the at least one agent.

Aspect 158. The kit of Aspect 157, wherein each dose of the at least one compound or the pharmaceutical composition and the at least one agent are co-formulated.

Aspect 159. The kit of Aspect 157, wherein each dose of the at least one compound or the pharmaceutical composition and the at least one agent are co-packaged.

Aspect 160. The kit of Aspect 157, wherein the dosage forms are formulated for oral administration and/or intravenous administration.

Aspect 161. The kit of Aspect 157, wherein the dosage forms are formulated for oral administration.

Aspect 162. The kit of Aspect 157, wherein the dosage forms are formulated for intravenous administration.

Aspect 163. The kit of Aspect 157, wherein the dosage form for the at least one compound or the pharmaceutical composition is formulated for oral administration and the dosage form for the at least one agent is formulated for intravenous administration.

Aspect 164. The kit of Aspect 157, wherein the dosage form for the at least one compound or the pharmaceutical composition is formulated for intravenous administration and the dosage form for the at least one agent is formulated for oral administration.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Synthesis of Representative Disclosed Compounds

Synthesis of 2-(6-(4-ethoxyphenyl)pyridin-3-yl)-6-fluoroquinoline-4-carboxylic acid (Cpd1)

Following the synthetic procedure described below, the target compound, 2-(6-(4-ethoxyphenyl)pyridin-3-yl)-6-fluoroquinoline-4-carboxylic acid (Cpd1) was prepared.

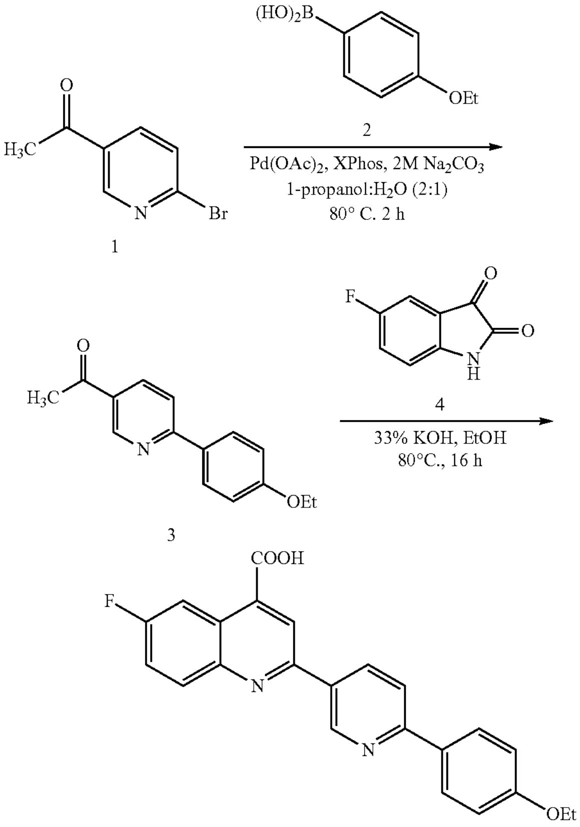

Cpd1

Step 1—Suzuki coupling. To a solution of 1-(6-bromopyridin-3-yl)ethan-1-one 1 (0.30 g, 1.50 mmol), 4-ethoxyphenylboronic acid 2 (0.274 g, 1.65 mmol) in 1-propanol (3.5 mL), palladium acetate (1.6 mg, 0.007 mmol), XPhos (9.7 mg, 0.020 mmol), aqueous sodium carbonate (2M, 1.58 mL), and then water (0.17 mL) were added. The reaction mixture was stirred at 80° C. for 2 h, (monitored by TLC) cooled to room temperature, diluted with EtOAc (40 mL) and water (30 mL), organic layer separated, washed with brine (30 mL). Organic layer dried over anhydrous $Na_2SO_4$, filtered and concentrated under reduced pressure to obtain crude material. Obtained crude material was purified using flash column chromatography using methylene chloride/hexanes to afford 1-(6-(4-ethoxyphenyl)pyridin-3-yl)ethan-1-one (3) as an off white solid (205 mg, 57% yield).

Step 2—Pfitzinger Reaction. The mixture of 5-fluoroisatin 4 (0.124 g, 0.75 mmol) and aqueous potassium hydroxide solution (33%, 3.4 mL, 0.22 M) was stirred and heated 100° C. for 10 min until clear yellow solution formed. To this solution, the slurry of 1-(6-(4-ethoxyphenyl)pyridin-3-yl)ethan-1-one 3 (0.200 g, 0.83 mmol) in ethanol (5 mL, 0.15M) was added. The reaction mixture was heated up to reflux with stirring for 16 hours (reaction progress was monitored by TLC) at 80° C., then cooled down to room temperature, ethanol was evaporated, and aqueous layer was acidified with aq. HCl (2M) to pH 2. The reaction was then subjected to workup and purification as discussed herein below using either workup/purification procedure I or workup/purification procedure II.

Workup/purification procedure I: The acidified mixture was extracted with EtOAc (3x30 mL). The combined organic layer was washed with brine (40 mL), dried over anhydrous $Na_2SO_4$ and concentrated in vacuo to afford crude material which was purified using flash column chromatography using methanol/dichloromethane to obtain 2-(6-(4-ethoxyphenyl)pyridin-3-yl)-6-fluoroquinoline-4-carboxylic acid (Cpd1) as a light yellow solid (125 mg, 43% yield).

Workup/purification procedure II: An alternative workup procedure for the Pfitzinger reaction is as follows. The acidified mixture with the resulting product that crashed out was stirred at room temperature for 2 h to get a free flowing solid that was then filtered. The solid was washed with a small amount of methanol to remove trapped water and dried under vacuum. The resulting powder was triturated with dichloromethane, ethyl acetate, and/or methanol, filtered, and dried under vacuum to obtain the desired product.

Synthesis of 2-(5-(4-ethoxyphenyl)pyridin-2-yl)-6-fluoroquinoline-4-carboxylic acid (Cpd2)

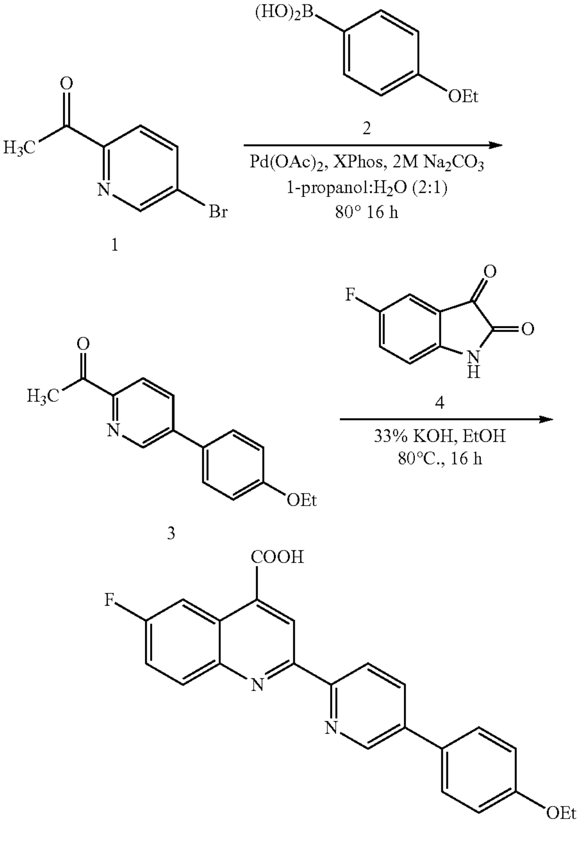

Cpd2

Following synthetic procedures similar to those described for the preparation of Cpd1, the target compound 2-(5-(4-ethoxyphenyl)pyridin-2-yl)-6-fluoroquinoline-4-carboxylic acid (Cpd2) was prepared as follows. Step 1 was conducted on 300 mg of 1-(5-bromopyridin-2-yl)ethan-1-one and 274 mg of (4-ethoxyphenyl)boronic acid to afford 1-(5-(4-ethoxyphenyl)pyridin-2-yl)ethan-1-one as white solid (320 mg, 88% yield). Step 2 (workup/purification I) was conducted on 187 mg of 5-fluoroisatin and 300 mg of 1-(5-(4-ethoxyphenyl)pyridin-2-yl)ethan-1-one to afford 2-(5-(4-ethoxyphenyl)pyridin-2-yl)-6-fluoroquinoline-4-carboxylic acid (Cpd2) as off white solid (124 mg, 28% yield).

Synthesis of 2-(5-(4-ethoxyphenyl)pyrimidin-2-yl)-6-fluoroquinoline-4-carboxylic acid (Cpd3)

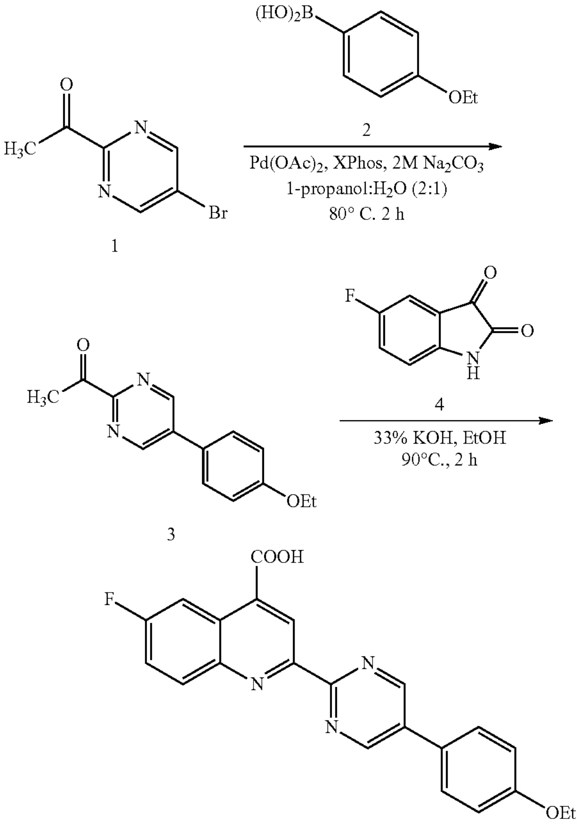

1

3

Cpd3

Following synthetic procedures similar to those described for the preparation of Cpd1, the target compound 2-(5-(4-ethoxyphenyl)pyrimidin-2-yl)-6-fluoroquinoline-4-carboxylic acid (Cpd3) was prepared as follows. Step 1 was conducted on 300 mg of 1-(5-bromopyrimidin-2-yl)ethan-1-one and 272 mg of (4-ethoxyphenyl)boronic acid to afford 1-(5-(4-ethoxyphenyl)pyrimidin-2-yl)ethan-1-one as brown solid (273 mg, 76%). Step 2 (workup/purification I) was conducted on 124 mg of 5-fluoroisatin and 200 mg of 1-(5-(4-ethoxyphenyl)pyridin-2-yl)ethan-1-one to afford 2-(5-(4-ethoxyphenyl)pyrimidin-2-yl)-6-fluoroquinoline-4-carboxylic acid (Cpd3) as a light yellow solid (28 mg, 10% yield).

Synthesis of 2-(5-(4-ethoxyphenyl)pyrazin-2-yl)-6-fluoroquinoline-4-carboxylic acid (Cpd4)

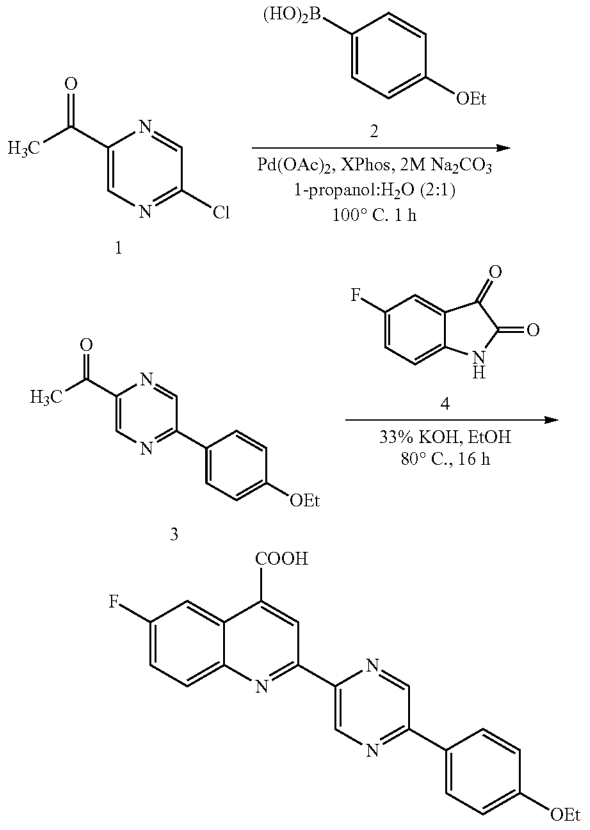

1

3

Cpd4

Following synthetic procedures similar to those described for the preparation of Cpd1, the target compound 2-(5-(4-ethoxyphenyl)pyrazin-2-yl)-6-fluoroquinoline-4-carboxylic acid (Cpd4) was prepared as follows. Step 1 was conducted on 300 mg of 1-(5-chloropyrazin-2-yl)ethan-1-one and 350 mg of (4-ethoxyphenyl)boronic acid to afford 1-(5-(4-ethoxyphenyl)pyrazin-2-yl)ethan-1-one as a white solid (53 mg, 11% yield). Step 2 (workup/purification I) was conducted on 34 mg of 5-fluoroisatin and 50 mg of 1-(5-(4-ethoxyphenyl)pyrazin-2-yl)ethan-1-one to afford 2-(5-(4-ethoxyphenyl)pyrazin-2-yl)-6-fluoroquinoline-4-carboxylic acid (Cpd4) as a light yellow solid (9 mg, 11%).

Synthesis of 2-(6-(4-ethoxyphenyl)pyridazin-3-yl)-6-fluoroquinoline-4-carboxylic acid (Cpd5)

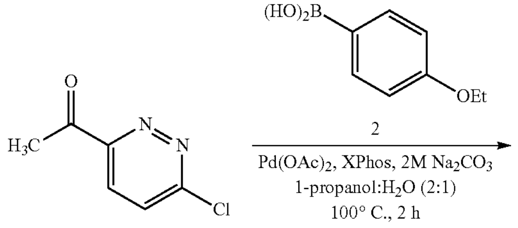

1

-continued

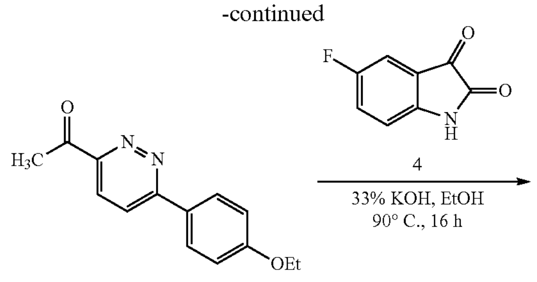

3

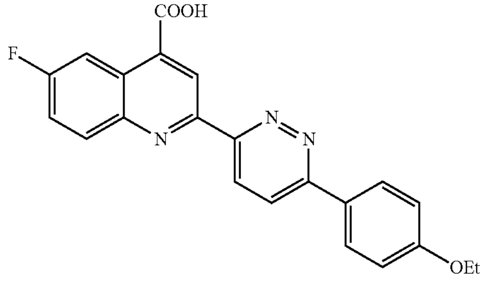

Cpd5

Following synthetic procedures similar to those described for the preparation of Cpd1, the target compound 2-(6-(4-ethoxyphenyl)pyridazin-3-yl)-6-fluoroquinoline-4-carboxylic acid (Cpd5) was prepared as follows. Step 1 was conducted on 100 mg of 1-(6-chloropyridazin-3-yl)ethan-1-one and 127 mg of (4-ethoxyphenyl)boronic acid to afford 1-(6-(4-ethoxyphenyl)pyridazin-3-yl)ethan-1-one as an off white solid (110 mg, 71%). Step 2 (workup/purification II) was conducted on 124 mg of 5-fluoroisatin and 200 mg of 1-(6-(4-ethoxyphenyl)pyridazin-3-yl)ethan-1-one to afford 2-(6-(4-ethoxyphenyl)pyridazin-3-yl)-6-fluoroquinoline-4-carboxylic acid (Cpd5) as a light brown solid (120 mg, 41%).

Synthesis of 2-(5-(3-ethoxyphenyl)pyrimidin-2-yl)-6-fluoroquinoline-4-carboxylic acid as Light Yellow Solid (Cpd6

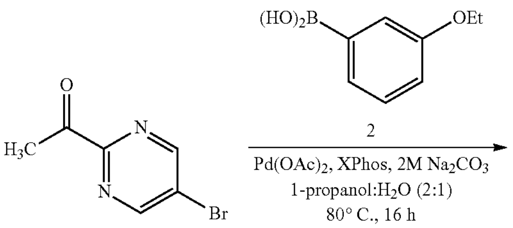

1

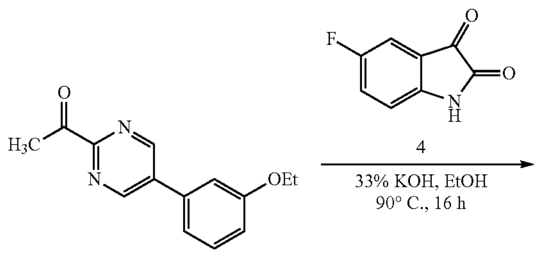

3

-continued

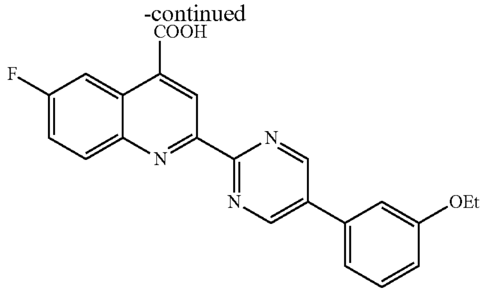

Cpd6

Following synthetic procedures similar to those described for the preparation of Cpd1, the target compound 2-(5-(3-ethoxyphenyl)pyrimidin-2-yl)-6-fluoroquinoline-4-carboxylic acid (Cpd6) was prepared as follows. Step 1 was conducted on 300 mg of 1-(5-bromopyrimidin-2-yl)ethan-1-one and 272 mg of (3-ethoxyphenyl)boronic acid to afford 1-(5-(3-ethoxyphenyl)pyrimidin-2-yl)ethan-1-one as a brown solid (198 mg, 54% yield). Step 2 (workup/purification I) was conducted on 116 mg of 5-fluoroisatin and 188 mg of 1-(5-(3-ethoxyphenyl)pyridin-2-yl)ethan-1-one to afford 2-(5-(3-ethoxyphenyl)pyrimidin-2-yl)-6-fluoroquinoline-4-carboxylic acid (Cpd6) as a light yellow solid (82 mg, 30% yield).

Synthesis of 2-(6-(3-ethoxyphenyl)pyridazin-3-yl)-6-fluoroquinoline-4-carboxylic acid (Cpd7)

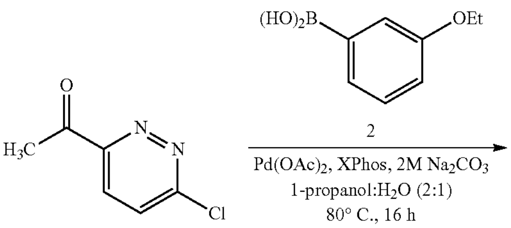

1

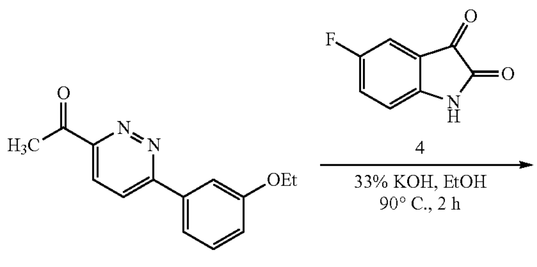

3

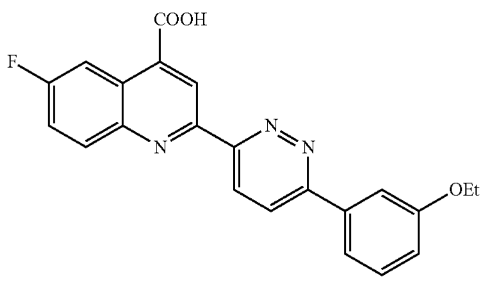

Cpd7

Following synthetic procedures similar to those described for the preparation of Cpd1, the target compound 2-(6-(3-ethoxyphenyl)pyridazin-3-yl)-6-fluoroquinoline-4-carboxylic acid (Cpd7) was prepared as follows. Step 1 was conducted on 300 mg of 1-(6-chloropyridazin-3-yl)ethan-1-one and 334 mg of (3-ethoxyphenyl)boronic acid to afford 1-(6-(3-ethoxyphenyl)pyridazin-3-yl)ethan-1-one as brown solid (335 mg, 72% yield). Step 2 (workup/purification I) was conducted on 124 mg of 5-fluoroisatin and 200 mg of 1-(6-(3-ethoxyphenyl)pyridazin-3-yl)ethan-1-one to afford 2-(6-(3-ethoxyphenyl)pyridazin-3-yl)-6-fluoroquinoline-4-carboxylic acid (Cpd7) as an off-white solid (41 mg, 13% yield, ~90% purity by $^1$H NMR).

The compounds disclosed above were assessed by mass spectrometry and the data are given below in Table 1.

TABLE 1

Mass Analysis Data.

| Name | Mass Calculated for Formula | Calculated Mass | Observed Mass |
|---|---|---|---|
| Cpd1 | $C_{23}H_{18}FN_2O_3$ | 389.1296 | 389.1292 |
| Cpd2 | $C_{23}H_{18}FN_2O_3$ | 389.1296 | 389.1291 |
| Cpd3 | $C_{22}H_{16}FN_3O_3$ | 390.1248 | 390.1247 |
| Cpd4 | $C_{22}H_{16}FN_3O_3$ | 390.1248 | 390.1247 |
| Cpd5 | $C_{22}H_{16}FN_3O_3$ | 390.1248 | 390.1248 |
| Cpd6 | $C_{22}H_{15}FN_3O_3$ | 388.1098 | 388.1 |
| Cpd7 | $C_{22}H_{15}FN_3O_3$ | 388.1098 | 388.1 |

2. Example 2: Biological Activity of Representative Disclosed Compounds

DHODH Enzymatic Assay: DHODH activity was determined at 25° C. following the reduction of 2,6-dichloroindophenol sodium salt (DCIP) at 600 nm (ε=18 800 $M^{-1}$ $cm^{-1}$) on a spectrophotometer. The reaction medium used contained 50 mM Tris-HCl, pH 8.0, 0.1% Triton X-100, 0.1 mM LDHO, 0.025 mM CoQ1, and 0.06 mM DCIP. The reaction was started by addition of the enzyme. The inhibitory potency of the compounds was evaluated by measuring the initial velocity of the reaction either in the absence or in the presence of the compounds at the indicated concentrations. The DHODH enzyme used was the recombinant human enzyme prepared as previously described (Hëlène Munier-Lehmann, et al., J. Med. Chem. 2015, 58:860-877).

MTS assay for cell growth/viability: Mitochondrial activity was measured to determine cell proliferation using an MTS assay (tetrazolium dye 3'[4,5-dimethylthiazol-2-yl]-2, 5-diphenyl-tetrazolium bromide). Metabolically active cells convert MTS tetrazolium salt into a purple formazan product that is soluble in tissue culture medium. The amount of formazan measured at 490 nm absorbance is proportional to the number of proliferating cells. MTS assays in AML cell lines were carried out with 20K cells plated per well in 96-well plates with Cpd3 or brequinar in a dose series ranging from 0.0001 to 10 μM. Triplicate wells were set up for each condition. At 96 hours, the MTS reagent was added and after approximately 4 hours the plates were read in a spectrophotometer.

Biological Activity. Cell proliferation assays were carried out using the MTS assay described herein using two AML cell lines (i.e., MOLM13 and OCI-AML3) with varied genetic backgrounds. The assays were carried out in a blinded fashion. Data for eight of the representative compounds are shown in Table 2, and the data show growth arrest in AML cell lines at submicromolar to micromolar concentrations ($IC_{50}$ ranges from 0.58-5.87 μM). Studies with one of the representative compounds, HOSU-78, demonstrated the ability to induce growth arrest at low micromolar concentrations ($IC_{50}$ ranges from 0.58-0.71 μM) similar to treatment with a reference compound, brequinar (BQR).

TABLE 2

Biological Activity Data.

| Name | h-DHODH $IC_{50}$ (nM) | $IC_{50}$ (μM) OCI-AML3 | $IC_{50}$ (μM) MOLM13 |
|---|---|---|---|
| Cpd1 | 628 | 4319 | 5.349 |
| Cpd2 | 317 | 709 | 0.571 |
| Cpd3 | Not tested | 3641 | n.d. |
| Cpd4 | 500 | 2099 | n.d. |
| Cpd5 | 4747 | >10,000 | n.d. |
| Cpd6 | 1818 | >10,000 | n.d. |
| Cpd7 | 605 | >10,000 | n.d. |

*"n.d." means that the compound was not tested in the indicated assay

FIG. 1 shows representative data and analysis for the effect of representative disclosed compounds p53 expression. Data were obtained for the effect of a comparator compound, RefCpd3, along with controls for vehicle treatment, and treatment with a reference compound, brequinar (indicated as "BQR" in the figures) using methods as described herein above. Briefly, AML cell lines were treated with vehicle, 50 nM test compound (designated by HOSU and a number), 50 nM RefCpd3 or 50 nM BQR for 24 hours. Lysates were prepared and immunoblots were performed for p53, with GAPDH used as a loading control. The structure for RefCpd3 is as follows, and was prepared as described in Intl. Pat. Appl. No. PCT/US19/38622, which is incorporated herein by reference:

RefCpd3

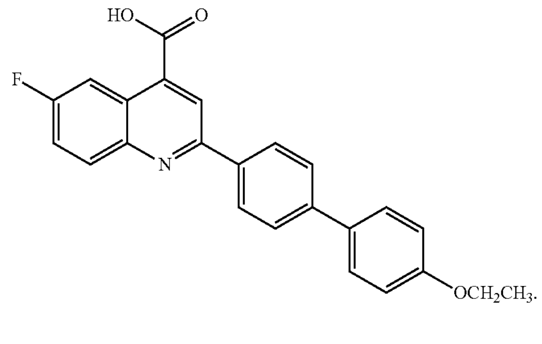

It will be apparent to those skilled in the art that various modifications and variations can be made in the present disclosure without departing from the scope or spirit of the disclosure. Other embodiments and aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A compound having a formula represented by a structure:

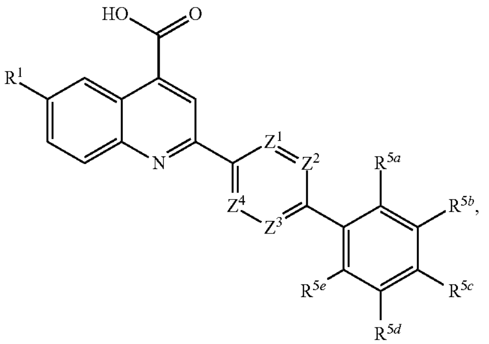

wherein each of $Z^1$, $Z^2$, $Z^3$, and $Z^4$ is independently selected from CH and N; wherein at least one $Z^1$, $Z^2$, $Z^3$, or $Z^4$ is N;

wherein $R^1$ is selected from hydrogen, halogen, —$SF_5$, —CN, —$N_3$, —OH, —$NH_2$, —$CF_3$, and —$CF_2CF_3$;

wherein one of $R^{5a}$, $R^{5b}$, $R^{5c}$, $R^{5d}$, and $R^{5e}$ is selected from a group having formula represented by a structure:

—$R^{20}$, —$R^{30}$-$A^1$-$R^{40}$, -$A^1$-$R^{40}$, -$A^1$-$R^{30}$-$A^2$-$R^{40}$, or -$A^1$-$R^{30}$-$A^2$-$R^{31}$-$A^3$-$R^{40}$, wherein $A^1$ is selected from —O— and —$NR^{50}$—;

wherein $R^{50}$ is selected from hydrogen, —C1-C10 alkyl, —C1-C10 aminoalkyl, and —C1-C10 hydroxyalkyl;

wherein $A^2$ is selected from —O— and —$NR^{60}$—;

wherein $R^{60}$ is selected from hydrogen, —C1-C10 alkyl, —C1-C10 aminoalkyl, and —C1-C10 hydroxyalkyl;

wherein $A^3$ is selected from —O— and —$NR^{70}$—;

wherein $R^{70}$ is selected from hydrogen, —C1-C10 alkyl, —C1-C10 aminoalkyl, and —C1-C10 hydroxyalkyl;

wherein $R^{20}$ is selected from halogen, —C1-C10 alkyl, —C1-C10 haloalkyl, —C1-C10 hydroxyalkyl, —C1-C10 alkylamino, and —C1-C10 alkoxy;

wherein each of $R^{30}$ and $R^{31}$ is independently selected from —C1-C10 alkanediyl, —C1-C10 haloalkanediyl, —C1-C10 aminoalkanediyl, and —C1-C10 hydroxyalkanediyl; and wherein $R^{40}$ is selected from —C1-C10 alkyl, —C1-C10 haloalkyl, —C1-C10 aminoalkyl, —C1-C10 hydroxyalkyl, and —$(CH_2)_n Ar^1$;

wherein n is an integer selected from 1, 2, and 3; and wherein $Ar^1$ is a phenyl group substituted with 0, 1, 2, 3, 4, or 5 groups independently selected from halogen, —$SF_5$, —CN, —$N_3$, —OH, —$NH_2$, —$C_1$-$C_4$ alkyl, —$C_1$-$C_4$ alkoxy, —$C_1$-$C_4$ haloalkyl, —$C_1$-$C_4$ aminoalkyl, —$C_1$-$C_4$ alkylamino, —$C_1$-$C_4$ haloalkylamino, —C1-C4 hydroxyalkyl, —$C_1$-$C_4$ halohydroxyalkyl, cycloalkyl, and heterocycloalkyl;

and wherein four of $R^{5a}$, $R^{5b}$, $R^{5c}$, $R^{5d}$, and $R^{5e}$ are independently selected from hydrogen, halogen, —$SF_5$, —CN, —$N_3$, —OH, —$NH_2$, —$CF_3$, and —$CF_2CF_3$;

or a pharmaceutically acceptable salt thereof.

2. The compound of claim 1, wherein $R^1$ is selected from halogen, —$SF_5$, —$CF_3$, and —$CF_2CF_3$.

3. The compound of claim 2, wherein $R^1$ is halogen.

4. The compound of claim 3, wherein $R^1$ is F.

5. The compound of claim 1, wherein $R^{5c}$ is halogen, C1-C7 haloalkyl, or —O(C1-C7 haloalkyl).

6. The compound of claim 5, wherein $R^{5c}$ is halogen.

7. The compound of claim 6, wherein $R^{5c}$ is F.

8. The compound of claim 5, wherein $R^{5c}$ is —$OCF_3$, —$OCH_2CF_3$, or —$OCF_2CF_3$.

9. The compound of claim 1, wherein $R^{50}$ is —OH, —O(C1-C7 alkyl), —C1-C7 hydroxyalkyl, —O—(C1-C7 hydroxyalkyl), —$CH_2$O(C1-C7 alkyl), or —$(CH_2)_2$O(C1-C7 alkyl).

10. The compound of claim 1, wherein $R^{5a}$ is selected from a group having formula represented by a structure:

—$R^{20}$, —$R^{30}$-$A^1$-$R^{40}$, -$A^1$-$R^{40}$, -$A^1$-$R^{30}$-$A^2$-$R^{40}$, or -$A^1$-$R^{30}$-$A^2$-$R^{31}$-$A^3$-$R^{41}$; and wherein each of $R^{5b}$, $R^{5c}$, $R^{5d}$, and $R^{5e}$ is independently selected from hydrogen, halogen, —$SF_5$, —CN, —$N_3$, —OH, —$NH_2$, —$CF_3$, and —$CF_2CF_3$.

11. The compound claim 10, wherein $R^{20}$ is selected from —C2-C7 alkylamino and —C2-C7 alkoxy.

12. The compound of claim 1, wherein $R^{5b}$ is selected from a group having formula represented by a structure:

—$R^{20}$, —$R^{30}$-$A^1$-$R^{40}$, -$A^1$-$R^{40}$, -$A^1$-$R^{30}$-$A^2$-$R^{40}$, or -$A^1$-$R^{30}$-$A^2$-$R^{31}$-$A^3$-$R^{41}$;

and wherein each of $R^{5a}$, $R^{5c}$, $R^{5d}$, and $R^{5e}$ is independently selected from hydrogen, halogen, —$SF_5$, —CN, —$N_3$, —OH, —$NH_2$, —$CF_3$, and —$CF_2CF_3$.

13. The compound of claim 12, wherein $R^{20}$ is selected from —C2-C7 alkylamino and —C2-C7 alkoxy.

14. The compound of claim 1, wherein $R^{5c}$ is selected from a group having formula represented by a structure:

—$R^{20}$, —$R^{30}$-$A^1$-$R^{40}$, -$A^1$-$R^{40}$, -$A^1$-$R^{30}$-$A^2R^{40}$, or -$A^1$-$R^{30}$-$A^2$-$R^{31}$-$A^3$-$R^{41}$;

and wherein each of $R^{5a}$, $R^{5b}$, $R^{5d}$, and $R^{5e}$ is independently selected from hydrogen, halogen, —$SF_5$, —CN, —$N_3$, —OH, —$NH_2$, —$CF_3$, and —$CF_2CF_3$.

15. The compound of claim 14, wherein $R^{20}$ is selected from —C2-C7 alkylamino and —C2-C7 alkoxy.

16. The compound of claim 1, having a structure represented by a formula:

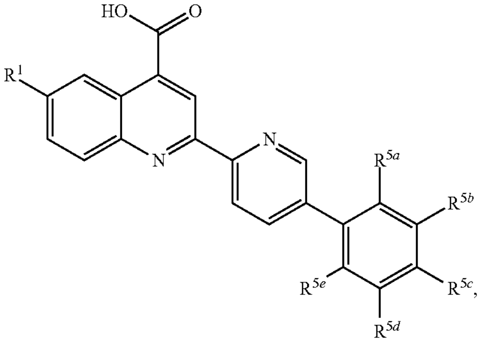

-continued
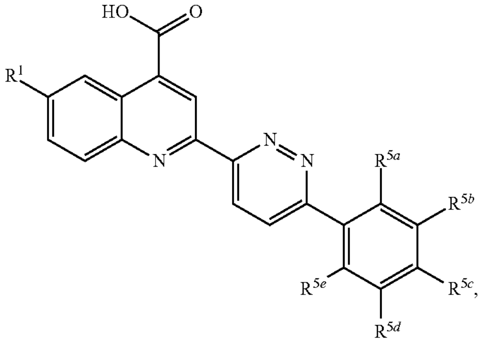
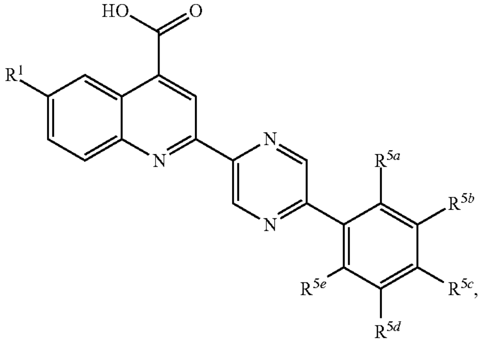
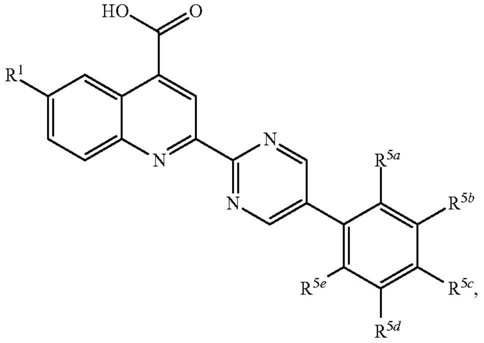
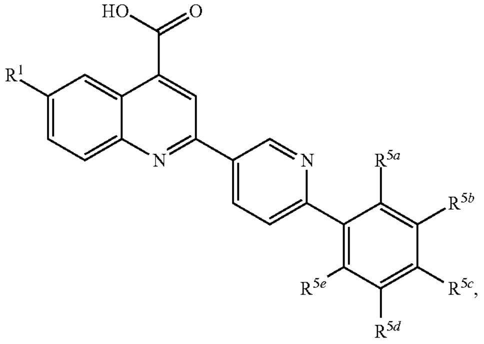
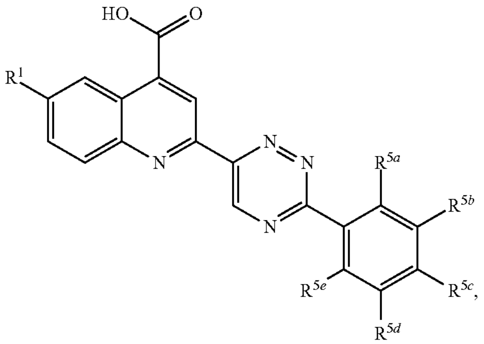
-continued
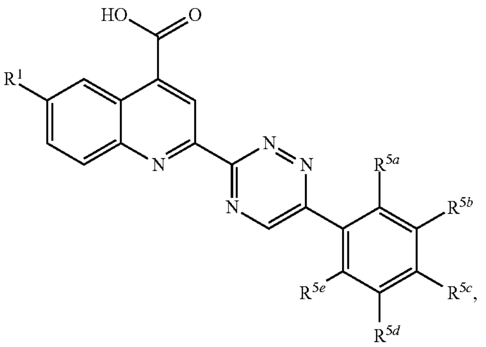
or
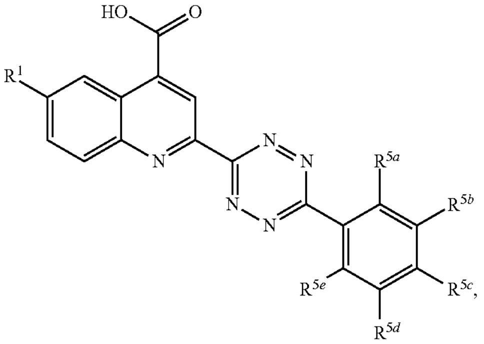
17. The compound of claim 1, present as:
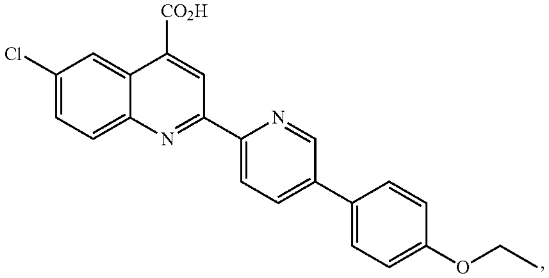
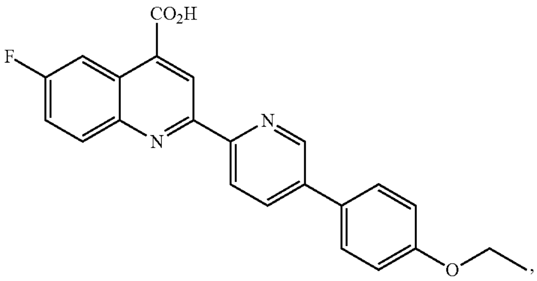
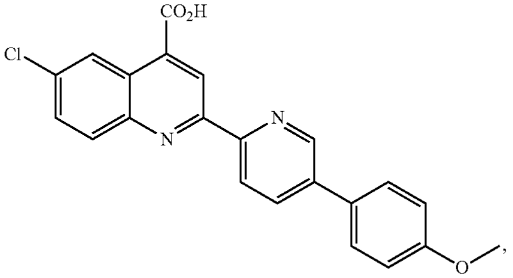

-continued
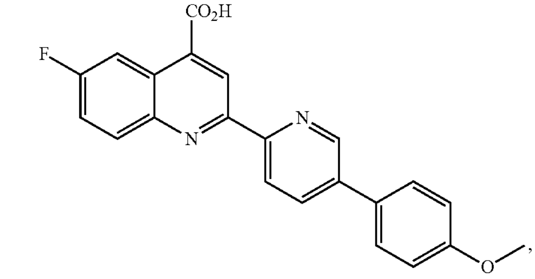
,
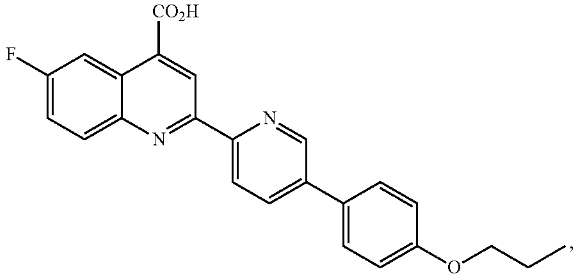
,
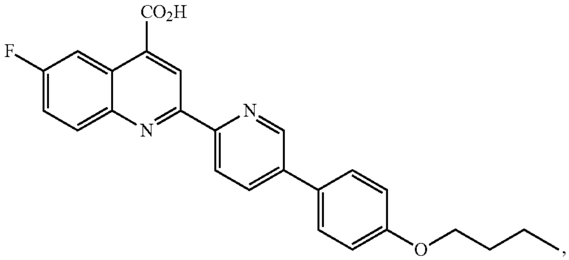
,
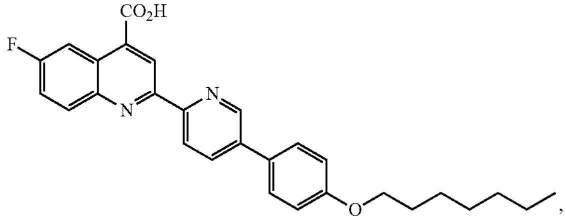
,
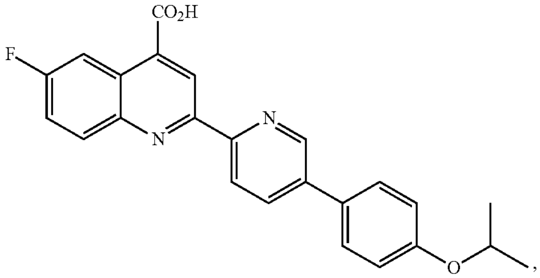
,
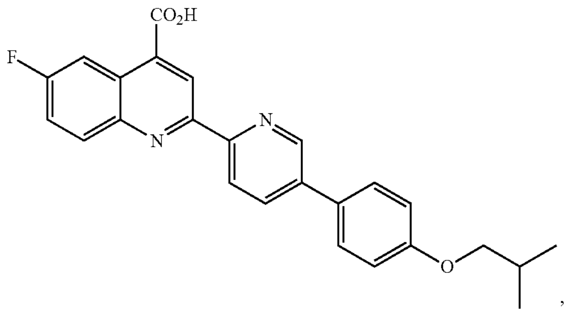
,
-continued
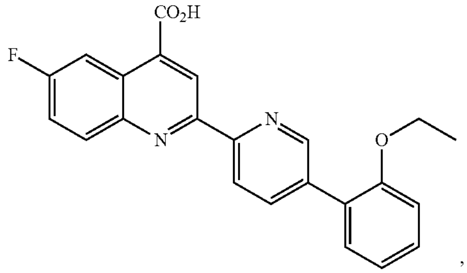
,
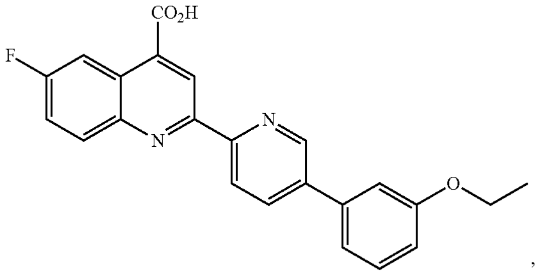
,
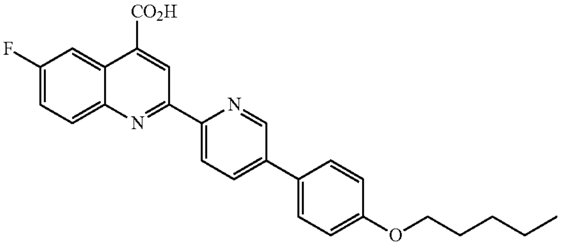
,
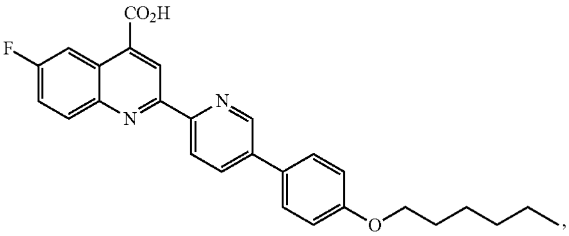
,
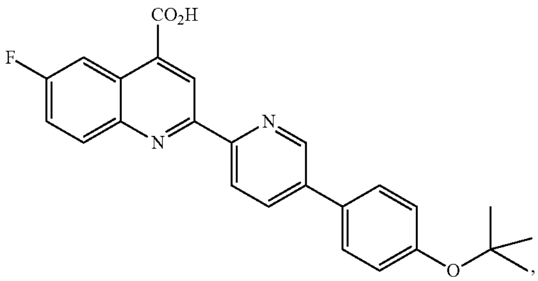
,
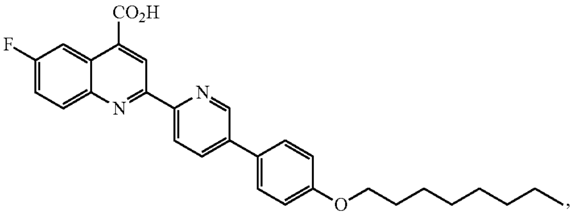
, -continued
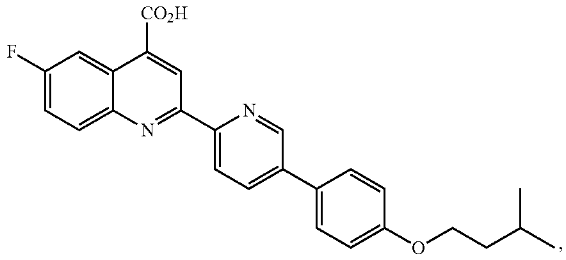
,
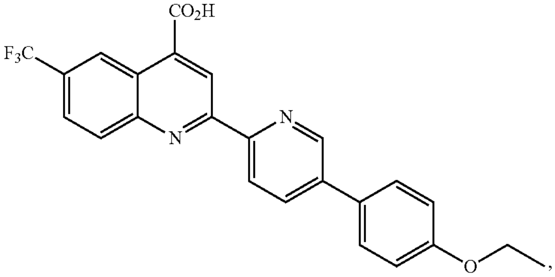
,
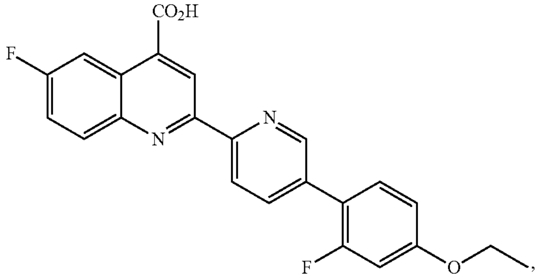
,
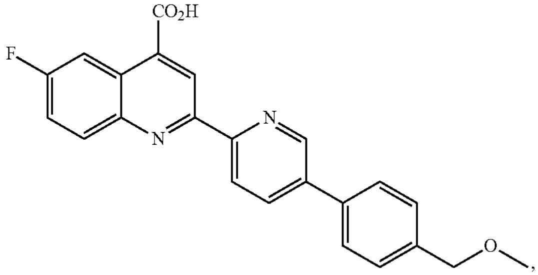
,
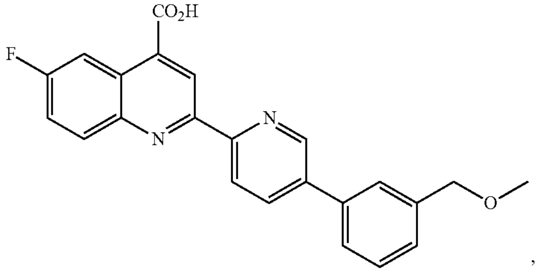
,
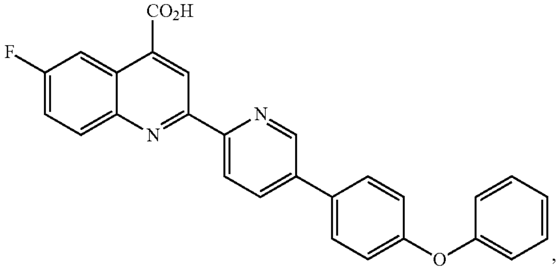
,
-continued
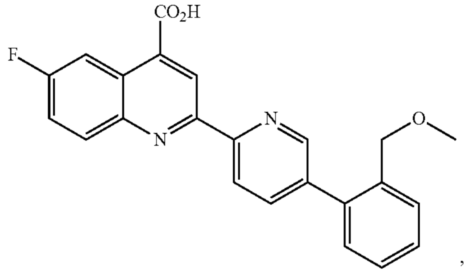
,
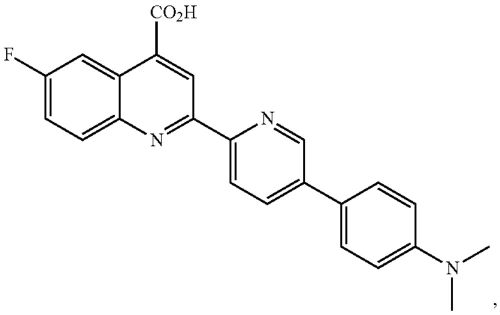
,
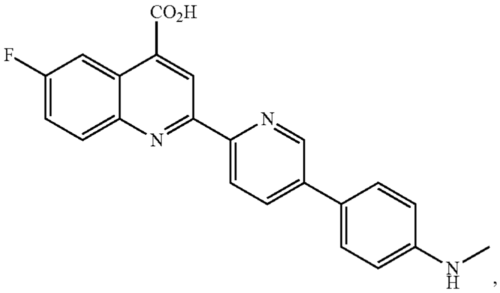
,
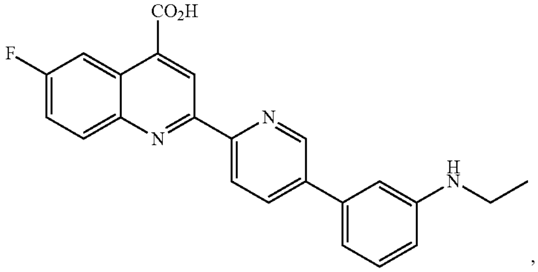
,
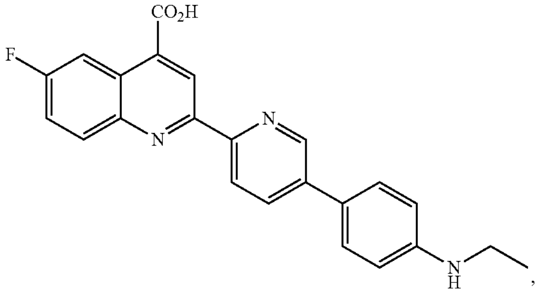
,
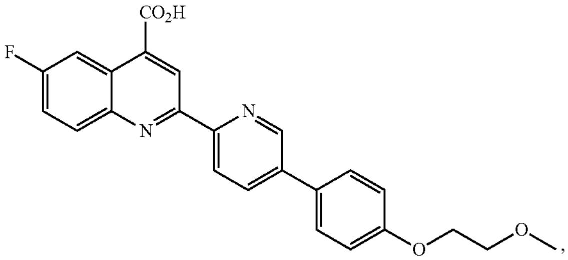
, -continued
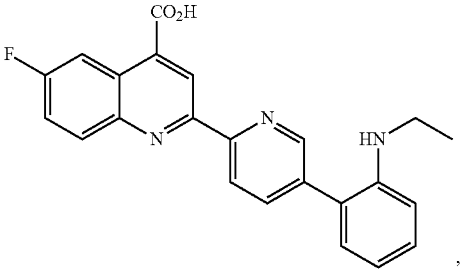
,
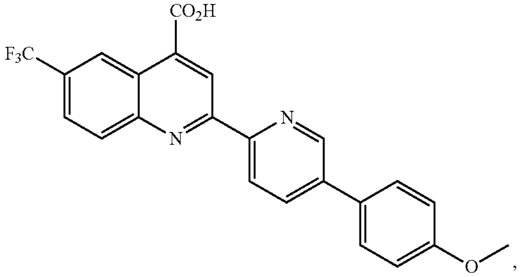
,
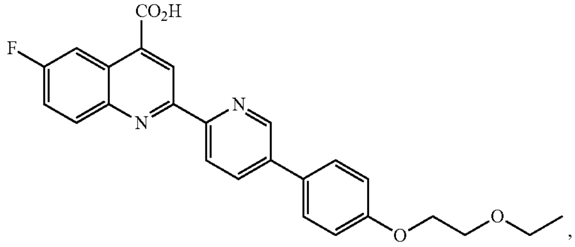
,
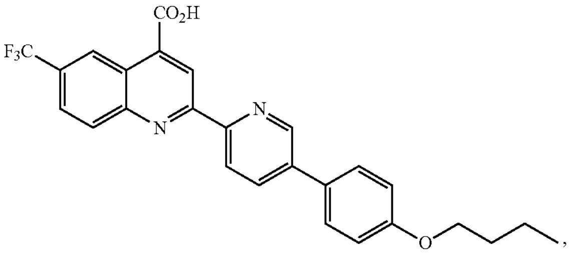
,
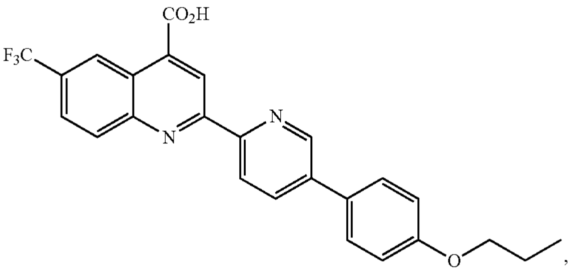
,
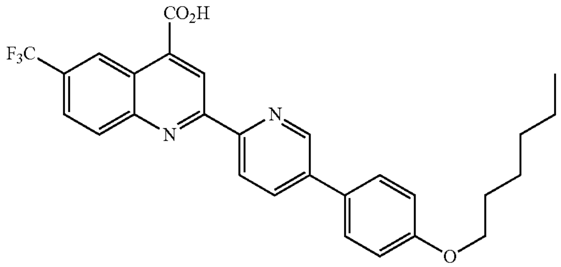
,
-continued
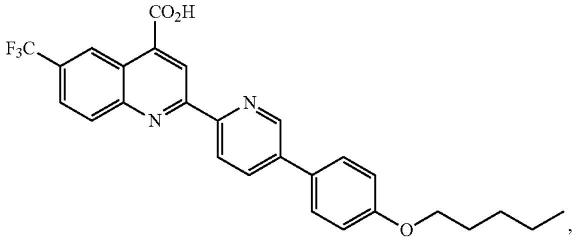
,
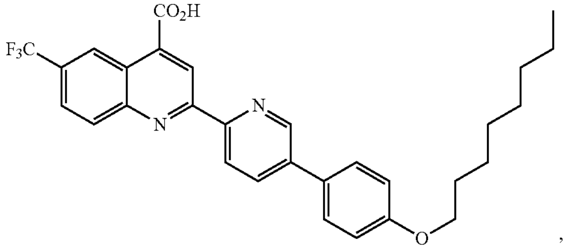
,
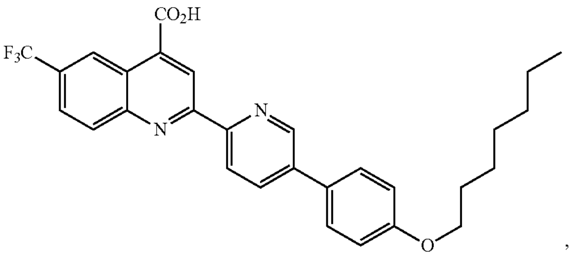
,
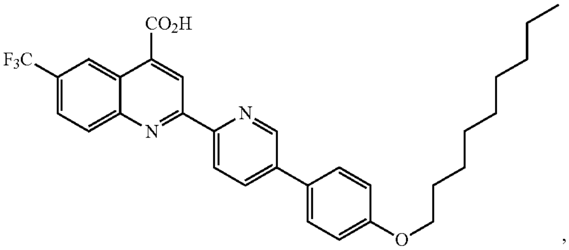
,
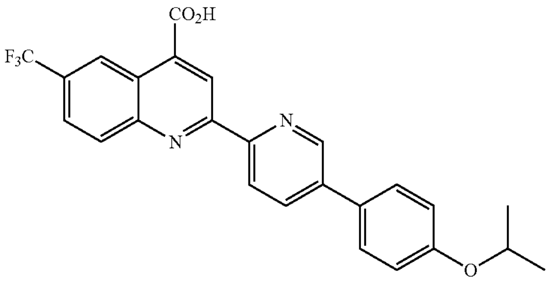
,
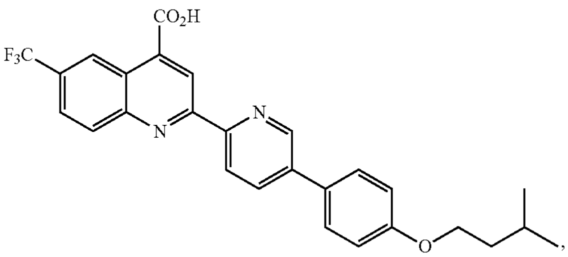
,

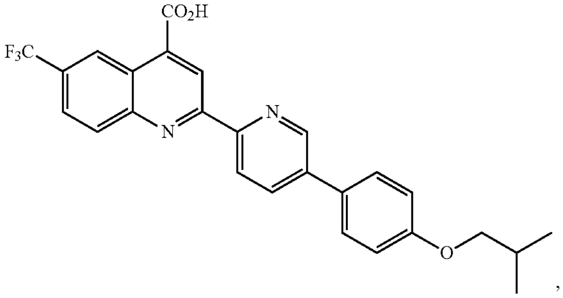
,
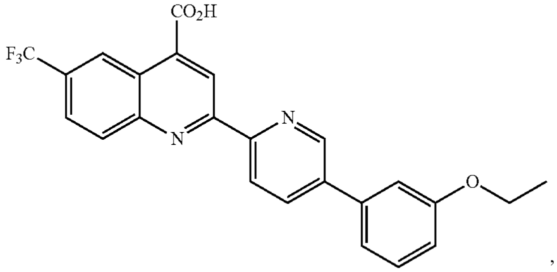
,
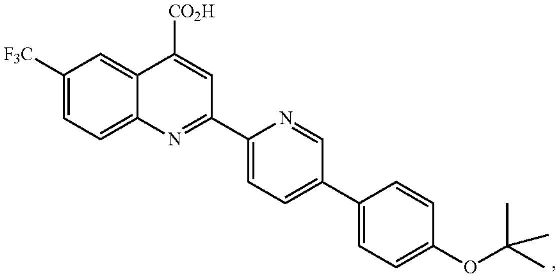
,
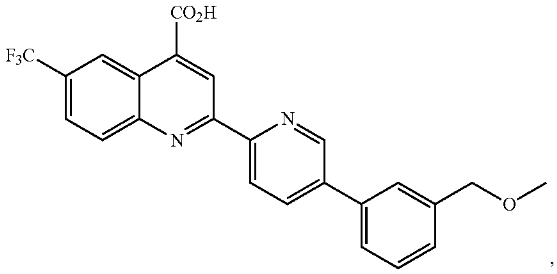
,
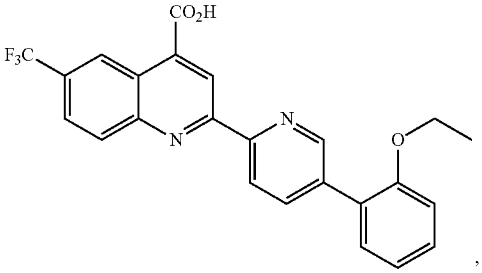
,
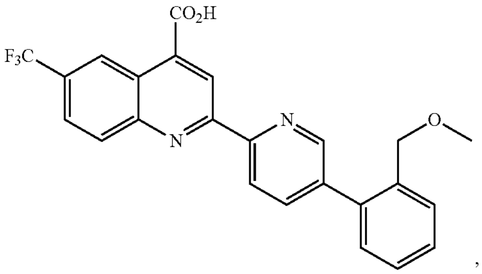
,
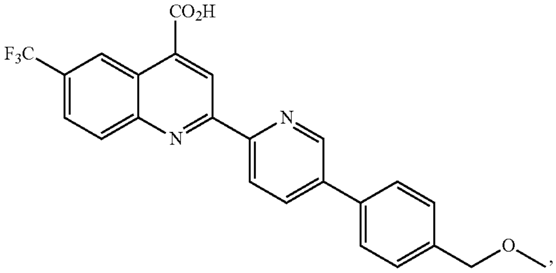
,
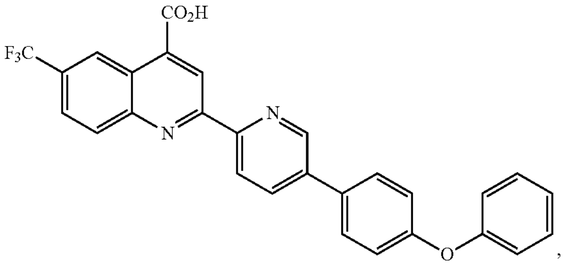
,
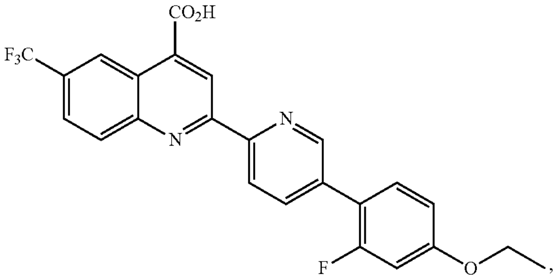
,
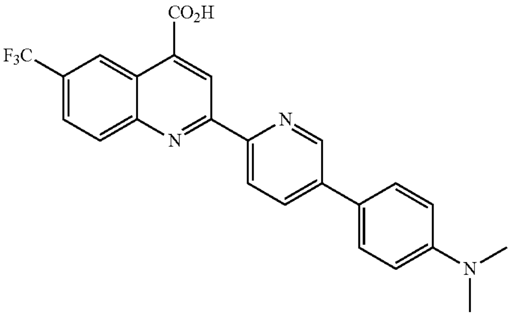
,
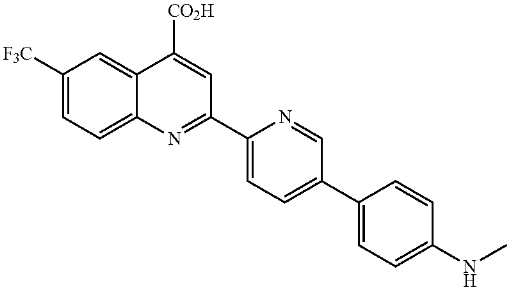
,
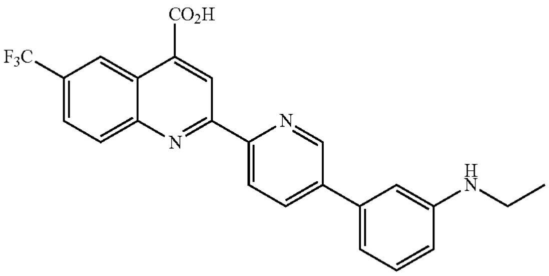
, -continued
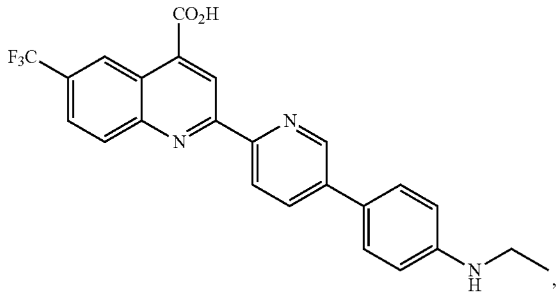
,
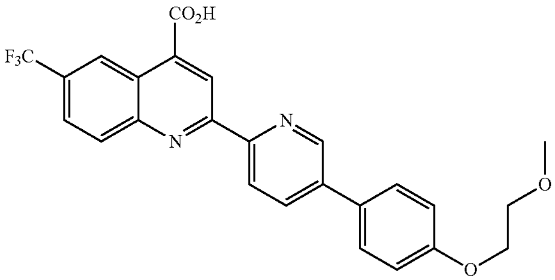
,
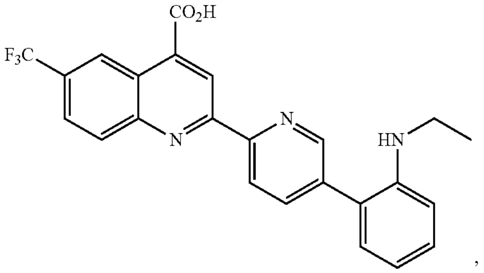
,
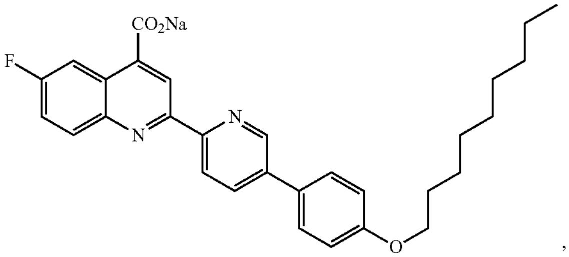
,
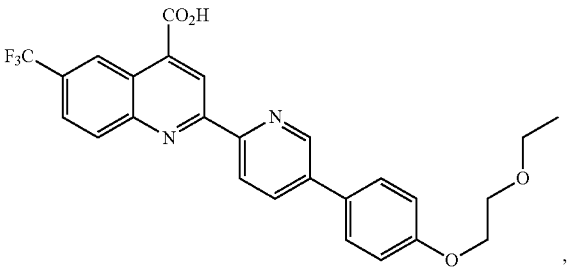
,
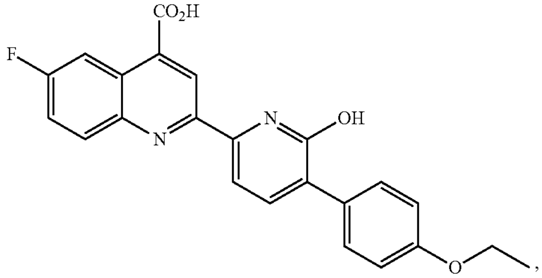
,
-continued
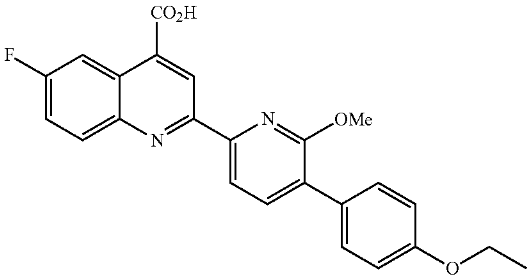
,
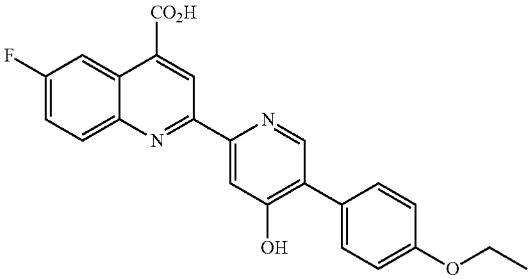
,
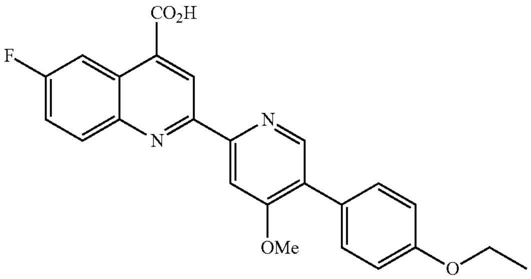
,
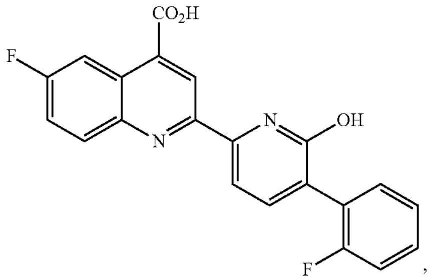
,
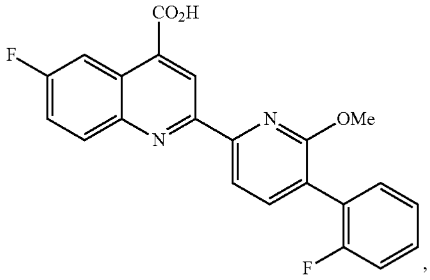
,
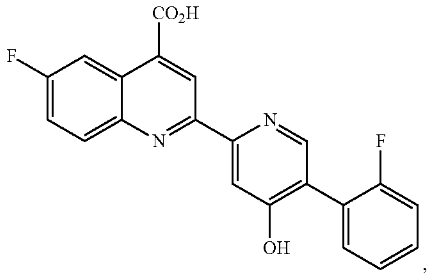
, -continued

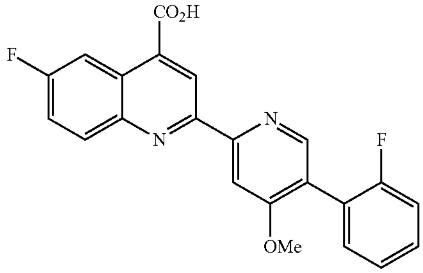

,

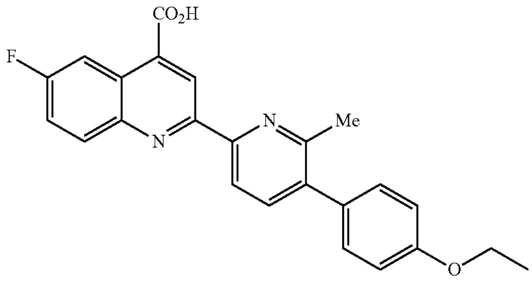

, or

-continued

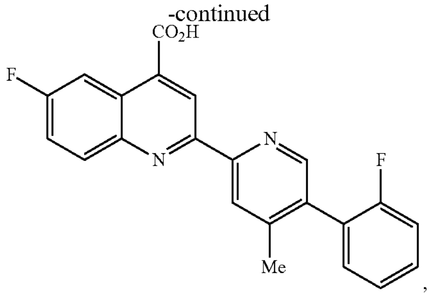

,

18. A pharmaceutical composition comprising a therapeutically effective amount of a compound of claim 1, or a pharmaceutically acceptable salt thereof, and a pharmaceutically acceptable carrier.

19. A method for the treatment of a disease or disorder in a mammal comprising the step of administering to the mammal a therapeutically effective amount of at least one compound of claim 1, or a pharmaceutically acceptable salt thereof.

20. The method of claim 19, wherein the disorder is a cancer.

* * * * *